US007659246B2

(12) United States Patent
Shiels et al.

(10) Patent No.: US 7,659,246 B2
(45) Date of Patent: Feb. 9, 2010

(54) TREATMENT OF OSTEOARTHRITIS

(75) Inventors: Ian Alexander Shiels, Muirlea (AU); David Fairlie, Springwood (AU)

(73) Assignee: Promics Pty Limited, New South Wales (AU)

( * ) Notice: Subject to any disclaimer, the term of this patent is extended or adjusted under 35 U.S.C. 154(b) by 0 days.

(21) Appl. No.: 10/531,560

(22) PCT Filed: Oct. 15, 2003

(86) PCT No.: PCT/AU03/01373

§ 371 (c)(1),
(2), (4) Date: Jan. 27, 2006

(87) PCT Pub. No.: WO2004/035079

PCT Pub. Date: Apr. 29, 2004

(65) Prior Publication Data

US 2006/0234921 A1    Oct. 19, 2006

(30) Foreign Application Priority Data

Oct. 16, 2002    (AU)    ............................... 2002952086

(51) Int. Cl.
*A61K 38/12*    (2006.01)
(52) U.S. Cl. ........................................................ 514/11
(58) Field of Classification Search .................... None
See application file for complete search history.

(56) References Cited

U.S. PATENT DOCUMENTS 7,410,945 B2 * 8/2008 Woodruff et al. ............... 514/9

FOREIGN PATENT DOCUMENTS

WO    WO 99/00406    * 1/1999

OTHER PUBLICATIONS

Finch A. M. et al., "Low-Molecular-Weight Peptidic and Cyclic Antagonists of the Receptor for the Complement Factor C5a", 1999, J. Med. Chem. vol. 42:1965-1974.*
Woodruff et al. "Antiarthritic Activity of an Orally Active C5a Receptor Antagonist Against Antigen-Induced Monarticular Arthritis in the Rat", Sep. 27, 2002, Arthritis & Rheumatism, vol. 46. pp. 2476-2485.*
Strachan et al. "A New Small Molecule C5a Receptor Antagonist Inhibits the Reverse-Passive Arthus Reaction and Endotoxic Shock in Rats", 2000, The Journal of Immunology, vol. 164. pp. 6560-6565.*
Kivitz et al. "Randomized placebo-controlled trial comparing efficacy and safety of valdecoxib with naproxen in patients with osteoarthritis" J. Fam. Prac., 2002, 51, 530-7.*

* cited by examiner

*Primary Examiner*—Cecilia Tsang
*Assistant Examiner*—Christina Bradley
(74) *Attorney, Agent, or Firm*—Mark D. Moore; Haynes and Boone, LLP

(57) ABSTRACT

This invention relates to methods of treatment of osteoarthritis, and especially to treatment of this condition with cyclic peptidic and peptidomimetic compounds which have the ability to modulate the activity of G protein-coupled receptors. The compounds preferably act as antagonists of the C5a receptor, and are active against C5a receptors on polymorphonuclear leukocytes and macrophages. Particularly preferred compounds for use in the invention are disclosed.

19 Claims, 6 Drawing Sheets

3D53-TREATED (0.3 MG/KG/DAY S.C.) KNEE JOINTS. DRUG TREATED SPECIMENS SHOW REDUCED THICKENING OF SYNOVIAL MEMBRANE WITH LESS INFLAMMATORY CELL INFILTRATE, AS WELL AS REDUCED ACCUMULATION OF FIBROUS TISSUE

TREATMENT OF OSTEOARTHRITIS

FIELD OF THE INVENTION

This invention relates to the treatment of osteoarthritis, and especially to treatment of this condition with novel cyclic peptidic and peptidomimetic compounds which have the ability to modulate the activity of G protein-coupled receptors. The compounds preferably act as antagonists of the C5a receptor, and are active against C5a receptors on polymorphonuclear leukocytes and macrophages.

BACKGROUND OF THE INVENTION

All references, including any patents or patent applications, cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents forms part of the common general knowledge in the art, in Australia or in any other country.

G protein-coupled receptors are prevalent throughout the human body, comprising approximately 60% of known cellular receptor types, and mediate signal transduction across the cell membrane for a very wide range of endogenous ligands. They participate in a diverse array of physiological and pathophysiological processes, including, but not limited to, those associated with cardiovascular, central and peripheral nervous system, reproductive, metabolic, digestive, immunological, inflammatory, and growth disorders, as well as other cell-regulatory and proliferative disorders. Agents which selectively modulate functions of G protein-coupled receptors have important therapeutic applications. These receptors are becoming increasingly recognised as important drug targets, due to their crucial roles in signal transduction (G protein-coupled Receptors, IBC Biomedical Library Series, 1996).

One of the most intensively studied G protein-coupled receptors is the receptor for C5a. C5a is one of the most potent chemotactic agents known, and recruits neutrophils and macrophages to sites of injury, alters their morphology; induces degranulation; increases calcium mobilisation, vascular permeability (oedema) and neutrophil adhesiveness; contracts smooth muscle; stimulates release of inflammatory mediators, including histamine, TNF-α, IL-1, IL-6, IL-8, prostaglandins, and leukotrienes, and of lysosomal enzymes; promotes formation of oxygen radicals; and enhances antibody production (Gerard and Gerard, 1994). α

Agents which limit the pro-inflammatory actions of C5a have potential for inhibiting chronic inflammation, and its accompanying pain and tissue damage. For these reasons, molecules which prevent C5a from binding to its receptors are useful for treating chronic inflammatory disorders driven by complement activation.

In our previous application No. PCT/AU98/00490, we described the three-dimensional structure of some analogues of the C-terminus of human C5a, and used this information to design novel compounds which bind to the human C5a receptor (C5aR), behaving as either agonists or antagonists of C5a. It had previously been thought that a putative antagonist might require both a C-terminal arginine and a C-terminal carboxylate for receptor binding and antagonist activity (Konteatis et al, 1994). In PCT/AU98/00490 we showed that in fact a terminal carboxylate group is not generally required either for high affinity binding to C5aR or for antagonist activity. Instead we found that a hitherto unrecognised structural feature, a turn conformation, was the key recognition feature for high affinity binding to the human C5a receptor on neutrophils. As described in our international patent application No. PCT/AU02/01427, filed on 17th October 2002, we used further refinements of these findings to design more tightly constrained structural templates which enable hydrophobic groups to be assembled into a hydrophobic array for interaction with a C5a receptor. We have subsequently found that a preferred compound of this class is able to inhibit cardiac and pulmonary fibrosis, and this is described in our international patent application No. PCT/AU03/00415, filed on 7 Apr. 2003. The entire disclosures of these specifications are incorporated herein by this reference.

Osteoarthritis is a non-inflammatory, chronic degenerative joint condition, characterized by degeneration of articular cartilage; in advanced cases there is also hypertrophy of bone at the joint margins, and changes in the synovial membrane. Secondary changes in underlying bone cause pain and affect joint function.

Osteoarthritis is strongly age-related, with over 50% of people over the age of 70 being treated for this condition. It is also associated with obesity and with over-use injuries, and is common in former athletes who engaged in weight-bearing sports. It is currently estimated that in the United States 35 million people—13 percent of the population—are 65 and older, and that more than half of these people have radiological evidence of osteoarthritis in at least one joint. By 2030, 20 percent of Americans—about 70 million people—will have passed their 65th birthday and will be at risk for osteoarthritis. It is estimated that there are about 103 million osteoarthritis sufferers in the European Union.

At present, therapies available to treat osteoarthritis are limited to the use of analgesics or anti-inflammatory agents, reduction in pressure across the joint, and weight loss. Most current treatments are designed only to relieve pain and/or inflammation, and to reduce or prevent the disability caused by bone and cartilage degeneration. COX-II inhibitors such as Celebrex, Vioxx and Bextra, which target inflammation, have recently become available for the treatment of this condition. To our knowledge none of these approved or experimental agents, and in particular no small molecule agent, targets the C5a receptor.

The available drug therapies target the symptoms but not the underlying cause of this disease; none of them inhibits the degenerative structural changes which are responsible for its progression. The disease continues to progress, and total joint replacement, especially of the hip or knee, is ultimately necessary in many patients. Furthermore, clinical testing of new therapies is complicated by the fact that the disease manifests itself differently in each person.

A variety of agents, ranging from tumour necrosis factor antagonists to dietary supplements such as S-adenosyl methionine or boron compounds, are in various stages of clinical trial. However, there is a great need in the art for effective, non-toxic agents which do not require administration by injection, and which can be produced at reasonable cost.

SUMMARY OF THE INVENTION

We now show for the first time that a specific inhibitor of the C5a receptor is able to ameliorate signs of damage in a model of induced osteoarthritis in dogs. This is the first reported case of an inhibitor of the complement system being used to modulate pathology in a model of osteoarthritis.

According to a first aspect, the invention provides a method of treatment of osteoarthritis, comprising the step of administering an effective amount of an inhibitor of a G protein-coupled receptor to a subject in need of such treatment.

Preferably the inhibitor is a compound which (a) is an antagonist of a G protein-coupled receptor, (b) has substantially no agonist activity, and (c) is a cyclic peptide or peptidomimetic compound of formula I

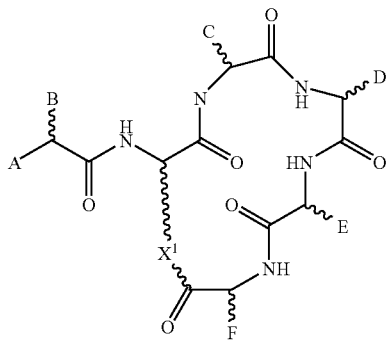

where A is H, alkyl, aryl, $NH_2$, NH-alkyl, N(alkyl)$_2$, NH-aryl, NH-acyl, NH-benzoyl, $NHSO_3$, $NHSO_2$-alkyl, $NHSO_2$-aryl, OH, O-alkyl, or O-aryl;

B is an alkyl, aryl, phenyl, benzyl, naphthyl or indole group, or the side chain of a D- or L-amino acid such as L-phenylalanine or L-phenylglycine, but is not the side chain of glycine, D-phenylalanine, L-homophenylalanine, L-tryptophan, L-homotryptophan, L-tyrosine, or L-homotyrosine;

C is a small substituent, such as the side chain of a D-, L- or homo-amino acid such as glycine, alanine, leucine, valine, proline, hydroxyproline, or thioproline, but is preferably not a bulky substituent such as isoleucine, phenylalanine, or cyclohexylalanine;

D is the side chain of a neutral D-amino acid such as D-Leucine, D-homoleucine, D-cyclohexylalanine, D-homocyclohexylalanine, D-valine, D-norleucine, D-homo-norleucine, D-phenylalanine, D-tetrahydroisoquinoline, D-glutamine, D-glutamate, or D-tyrosine, but is preferably not a small substituent such as the side chain of glycine or D-alanine, a bulky planar side chain such as D-tryptophan, or a bulky charged side chain such as D-arginine or D-Lysine;

E is a bulky substituent, such as the side chain of an amino acid selected from the group consisting of L-phenylalanine, L-tryptophan and L-homotryptophan, or is L-1-napthyl or L-3-benzothienyl alanine, but is not the side chain of D-tryptophan, L-N-methyltryptophan, L-homophenylalanine, L-2-naphthyl L-tetrahydroisoquinoline, L-cyclohexylalanine, D-leucine, L-fluorenylalanine, or L-histidine;

F is the side chain of L-arginine, L-homoarginine, L-citrulline, or L-canavanine, or a bioisostere thereof, ie. a side chain in which the terminal guanidine or urea group is retained, but the carbon backbone is replaced by a group which has different structure but is such that the side chain as a whole reacts with the target protein in the same way as the parent group; and X is —(CH$_2$)$_n$NH— or (CH$_2$)$_n$—S—, where n is an integer of from 1 to 4, preferably 2 or 3; —(CH$_2$)$_2$O—; —(CH$_2$)$_3$O—; —(CH$_2$)$_3$—; —(CH$_2$)$_4$—; —CH$_2$COCHRNH—; or —CH$_2$—CHCOCHRNH—, where R is the side chain of any common or uncommon amino acid.

In C, both the cis and trans forms of hydroxyproline and thioproline may be used.

Preferably A is an acetamide group, an aminomethyl group, or a substituted or unsubstituted sulphonamide group.

Preferably where A is a substituted sulphonamide, the substituent is an alkyl chain of 1 to 6, preferably 1 to 4 carbon atoms, or a phenyl or toluoyl group. In a particularly preferred embodiment, the compound has antagonist activity against C5aR, and has no C5a agonist activity.

The compound is preferably an antagonist of C5a receptors on human and mammalian cells including, but not limited to, human polymorphonuclear leukocytes and human macrophages. The compound preferably binds potently and selectively to C5a receptors, and more preferably has potent antagonist activity at sub-micromolar concentrations. Even more preferably the compound has a receptor affinity $IC_{50}<25$ μM, and an antagonist potency $IC_{50}<1$ μM.

Most preferably the compound is selected from the group consisting of compounds 1 to 6, 10 to 15, 17, 19, 20, 22, 25, 26, 28, 30, 31, 33 to 37, 39 to 45, 47 to 50, 52 to 58 and 60 to 70 described in PCT International Patent Application No. PCT/AU02/01427 (which gave rise to U.S. patent application Ser. No. 10/493,117, published Sep. 28, 2006 as 20060217530), including the following compounds:

1

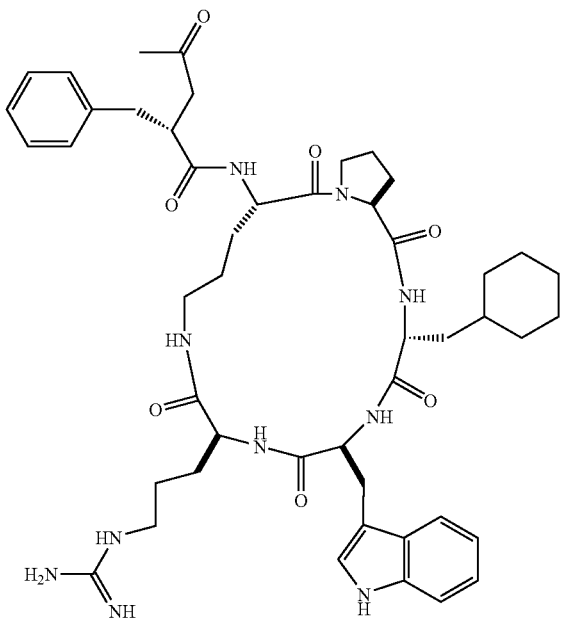

2
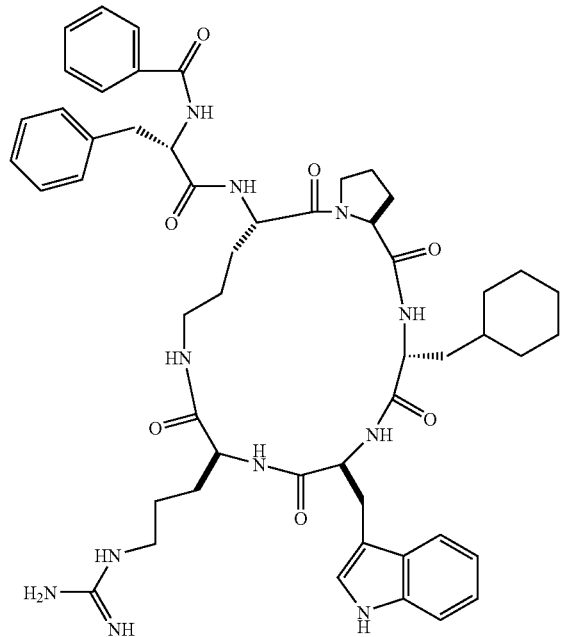
3
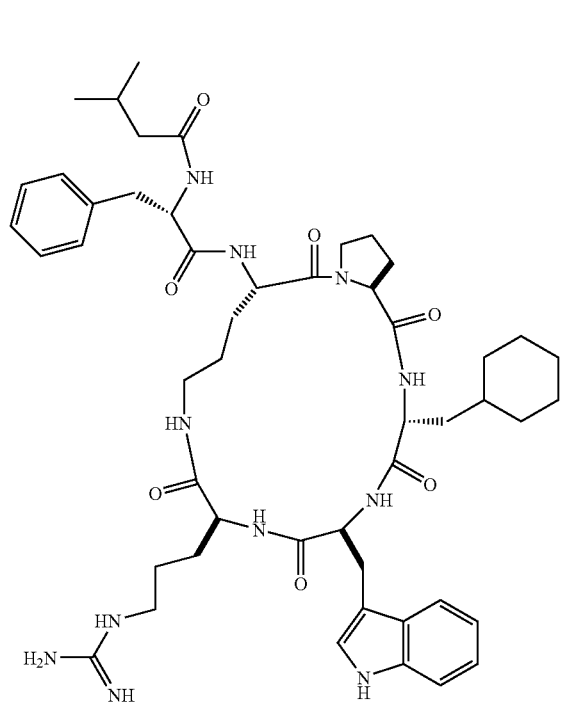
4
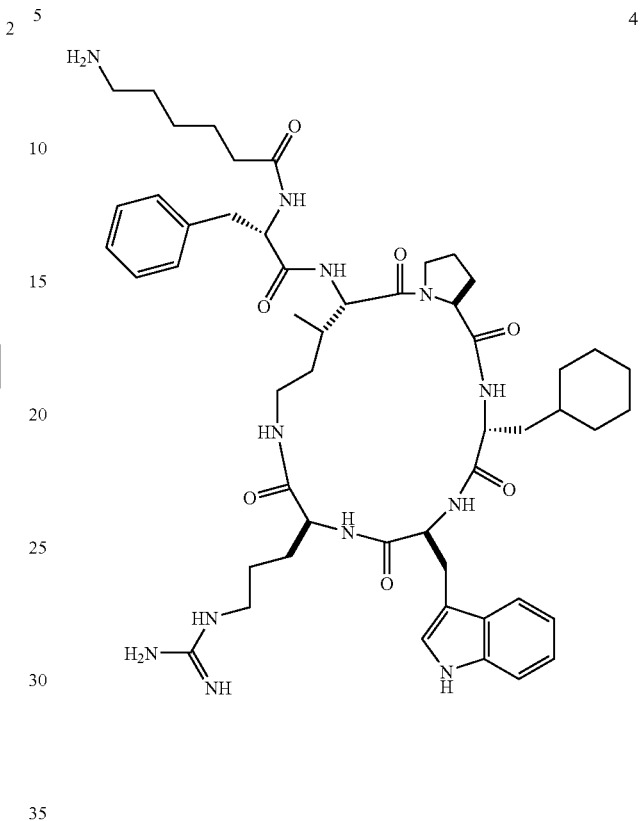
5
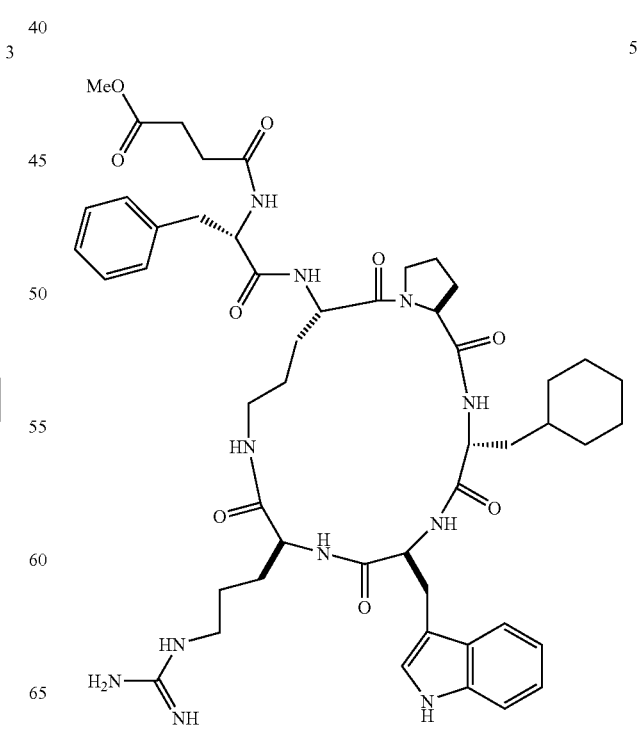

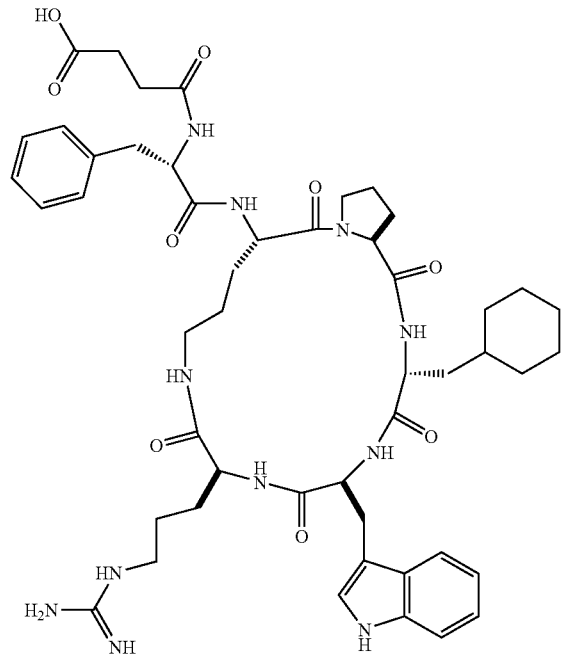
6
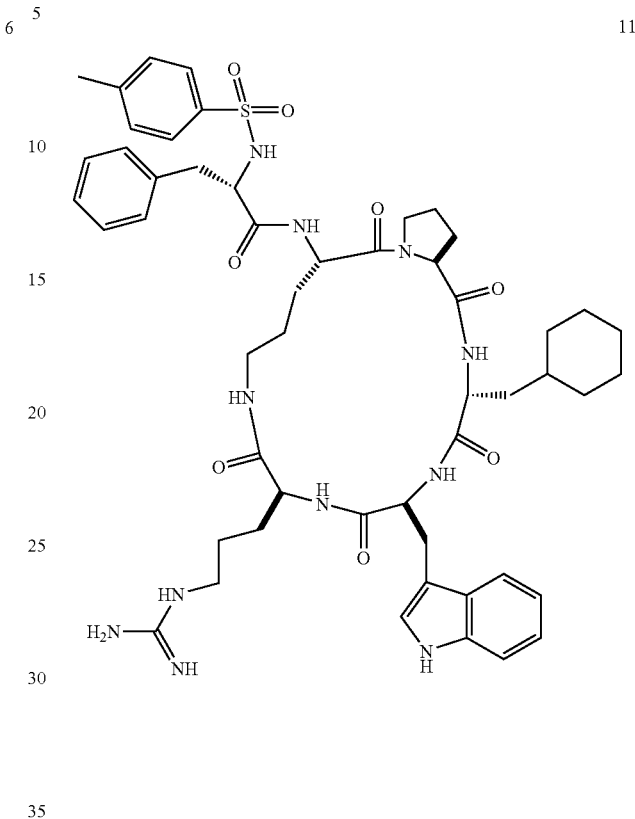
11
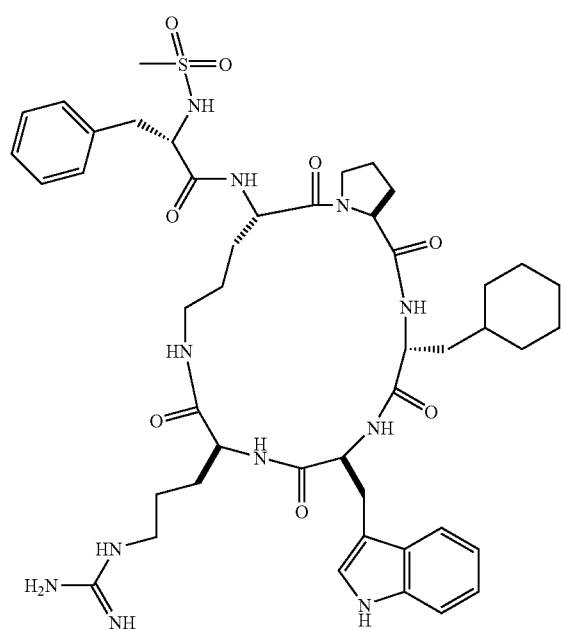
10
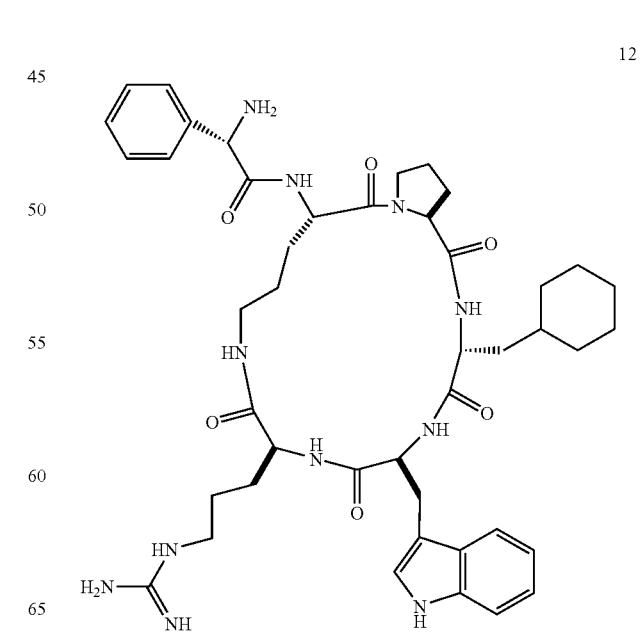
12

13
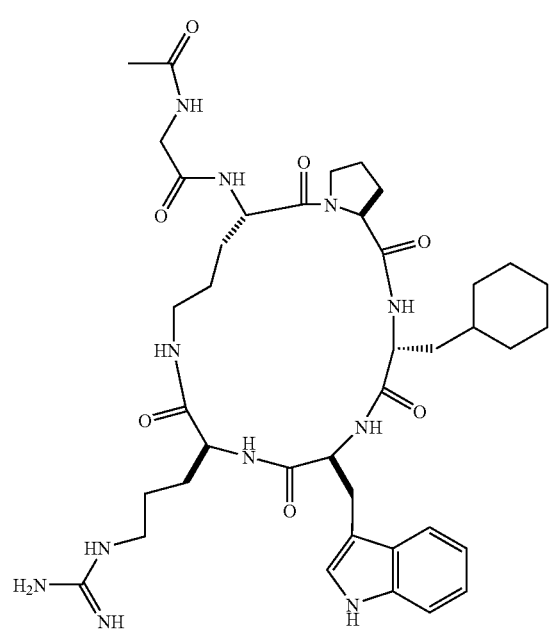
14
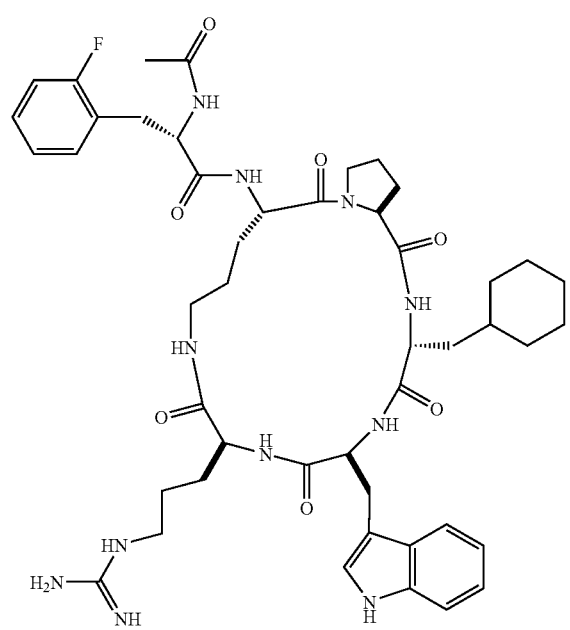
15
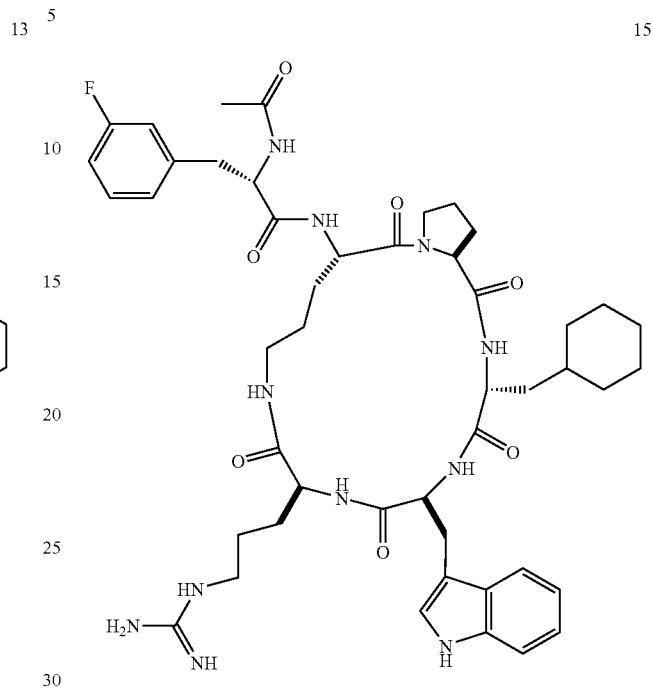
17
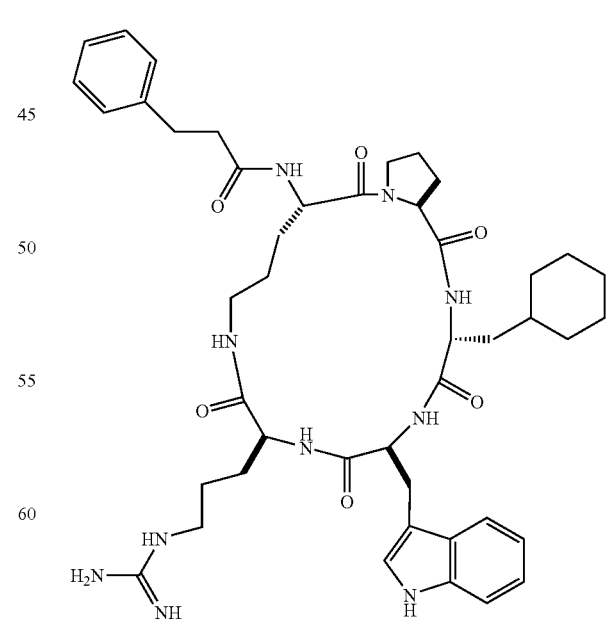

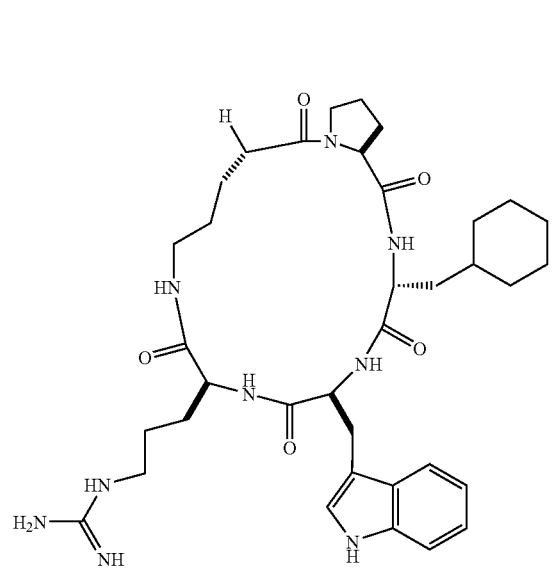
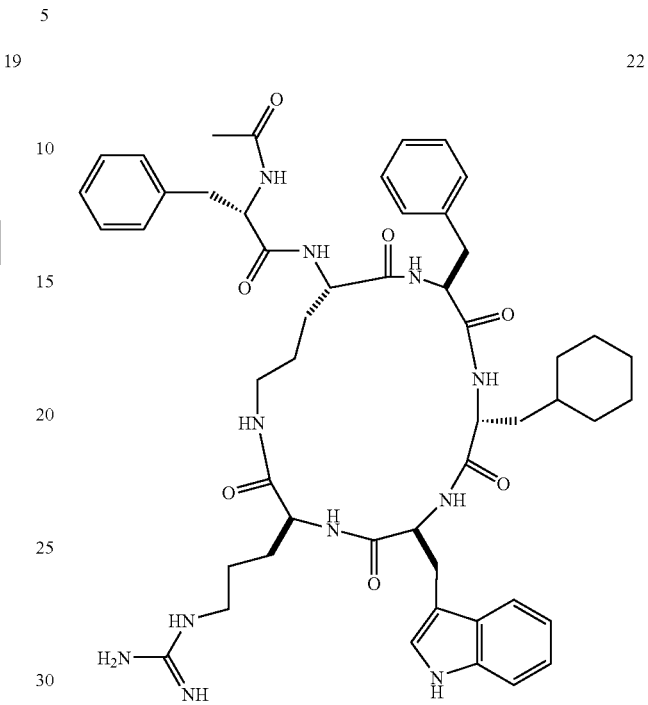
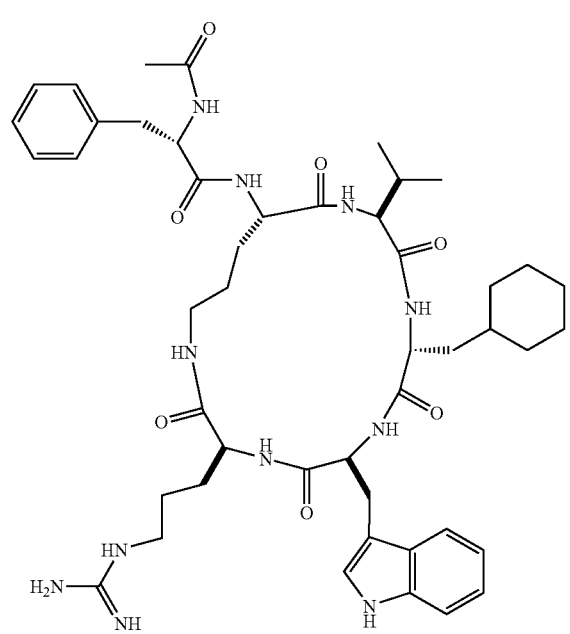
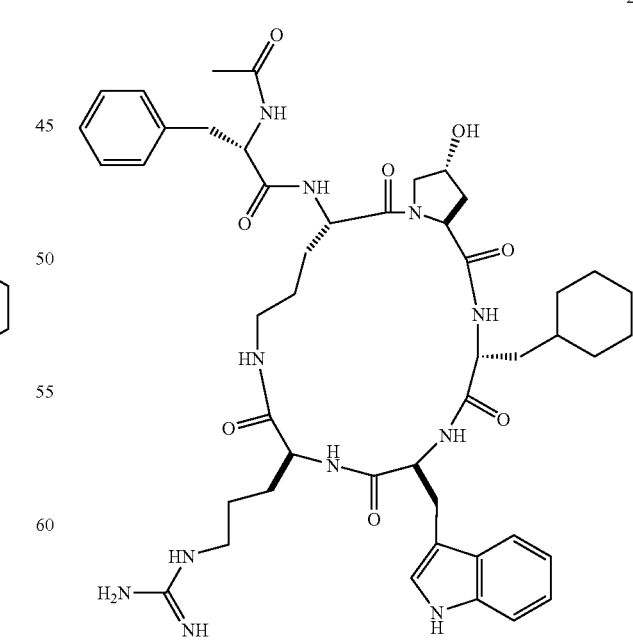

26
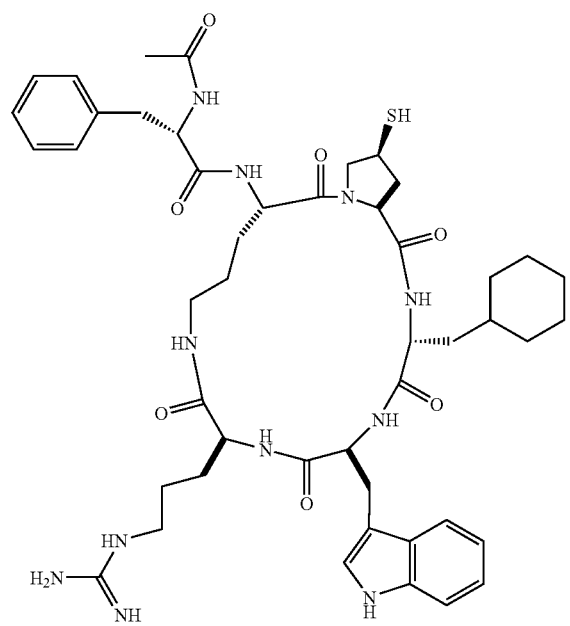
28
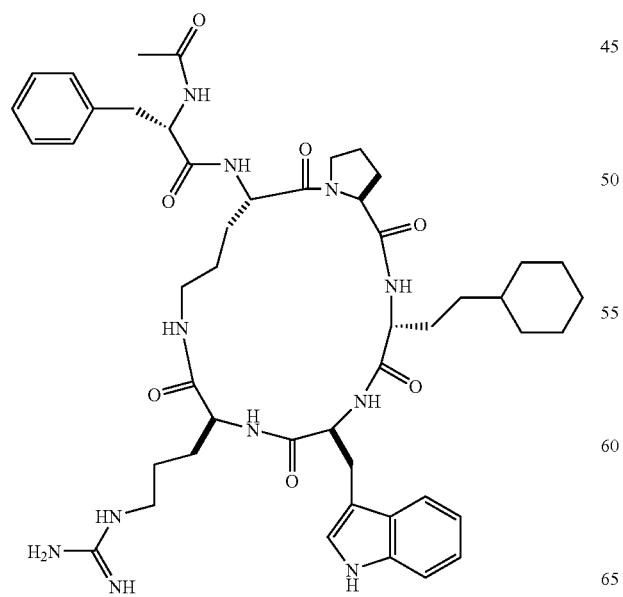
30
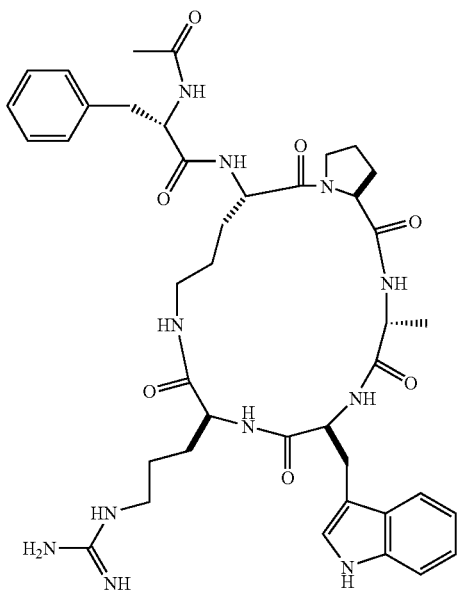
31
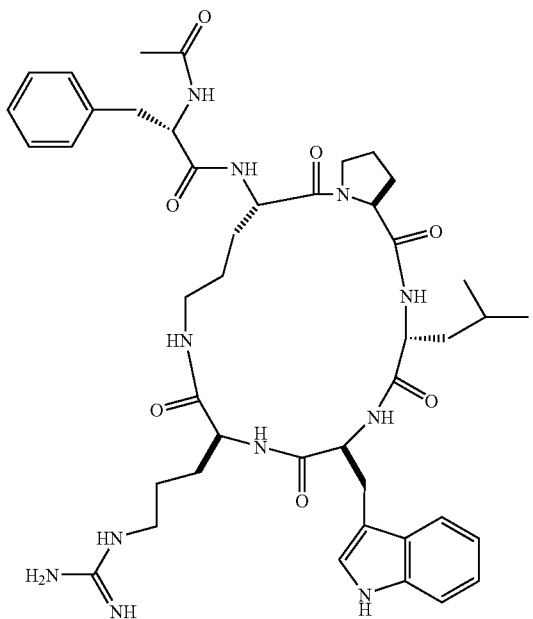

33
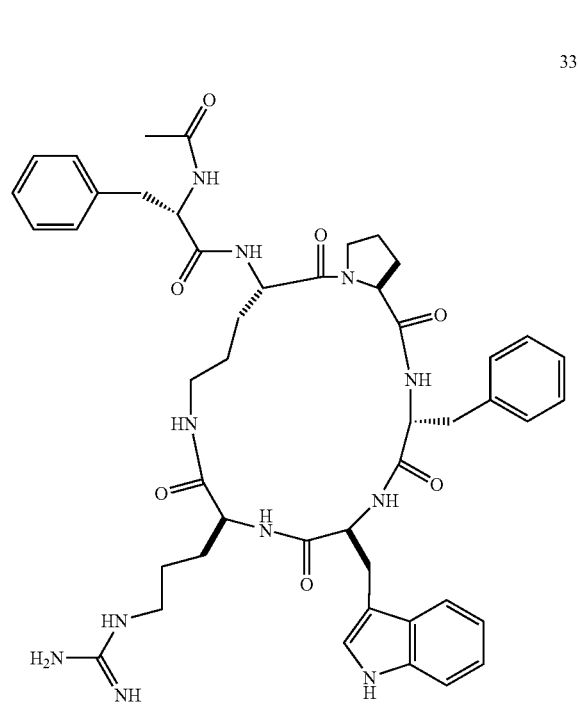
35
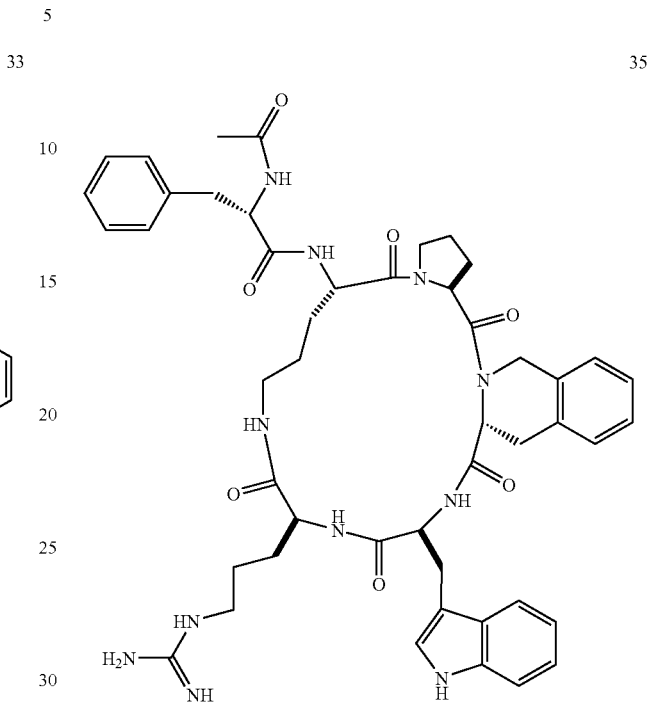
34
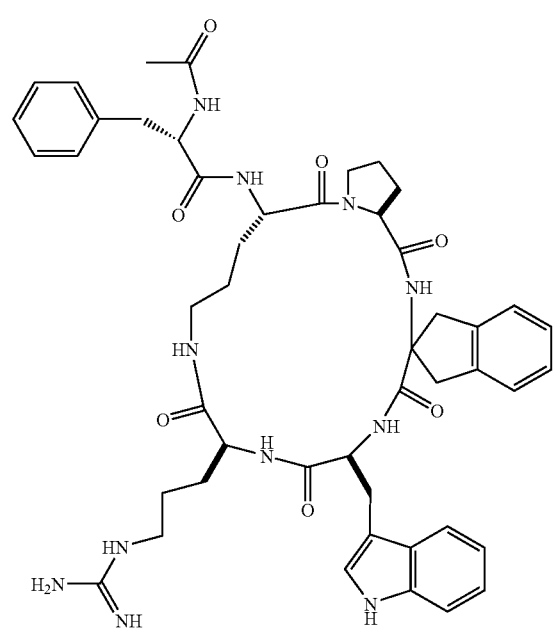
36
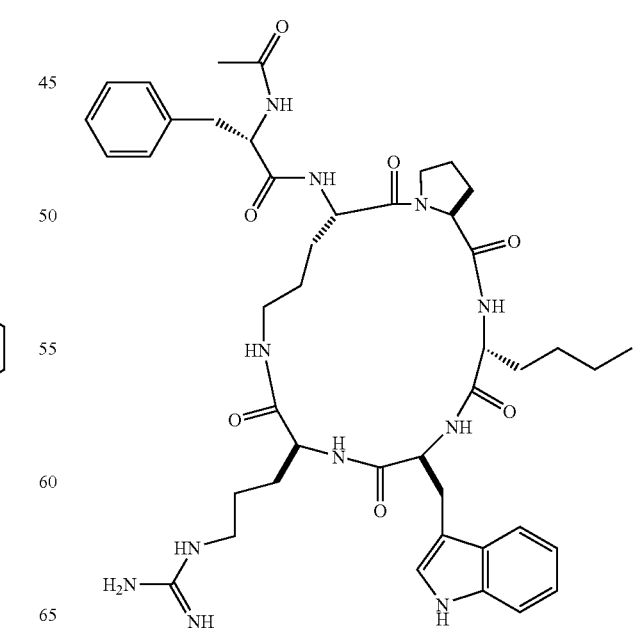

37
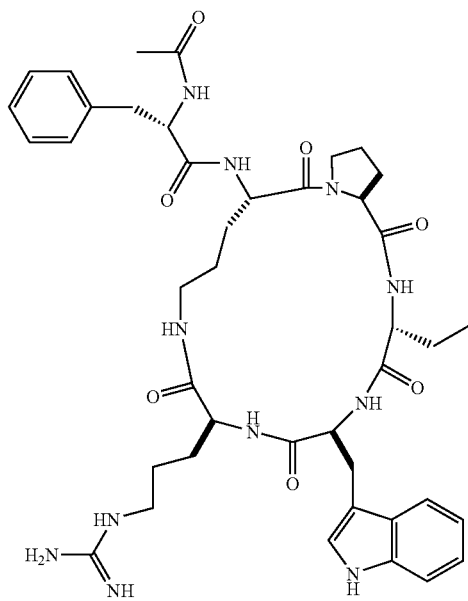
40
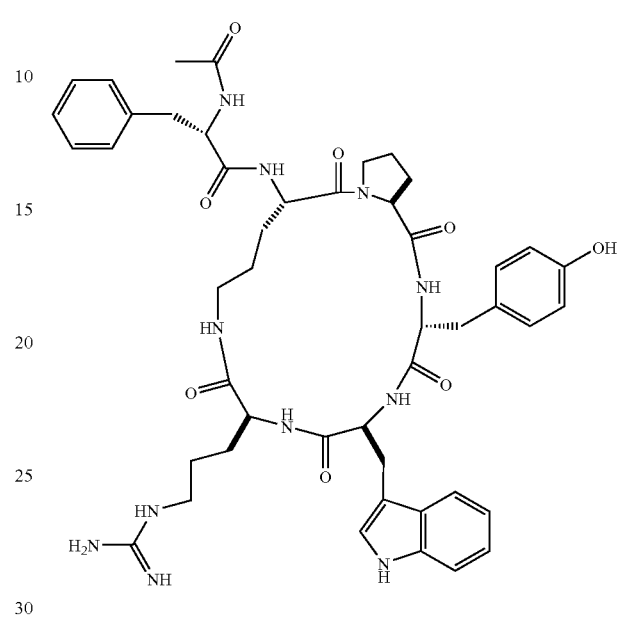
39
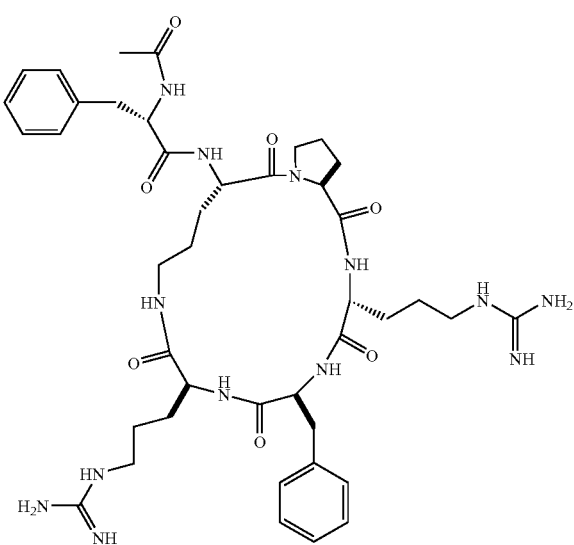
41
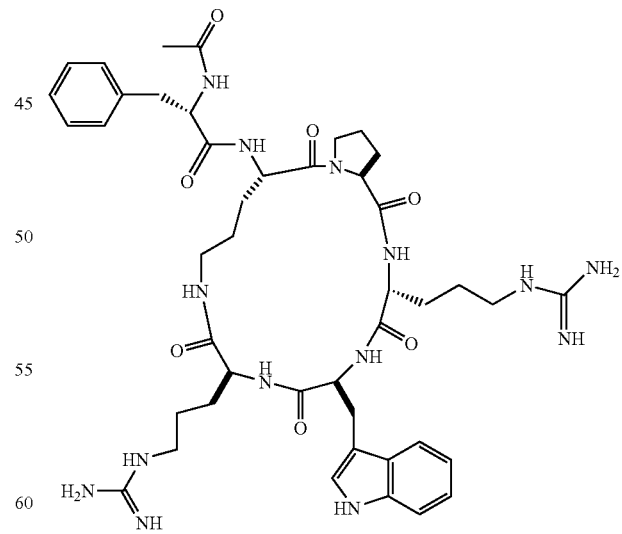

42
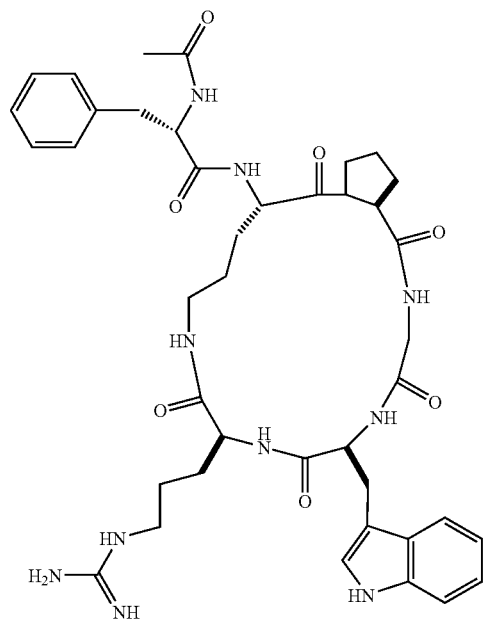
44
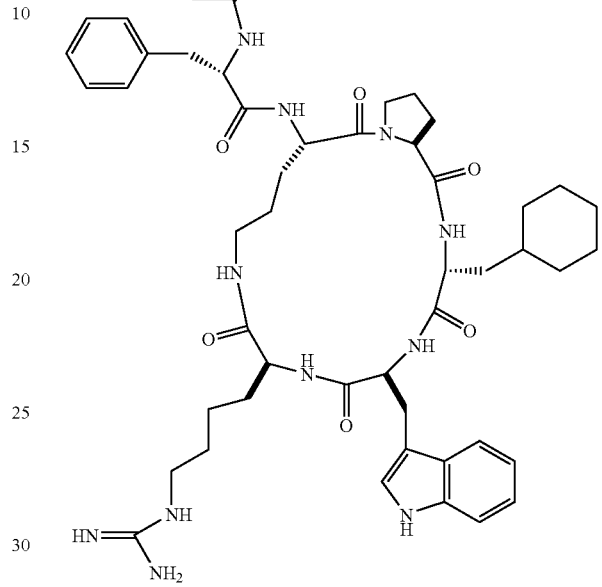
43
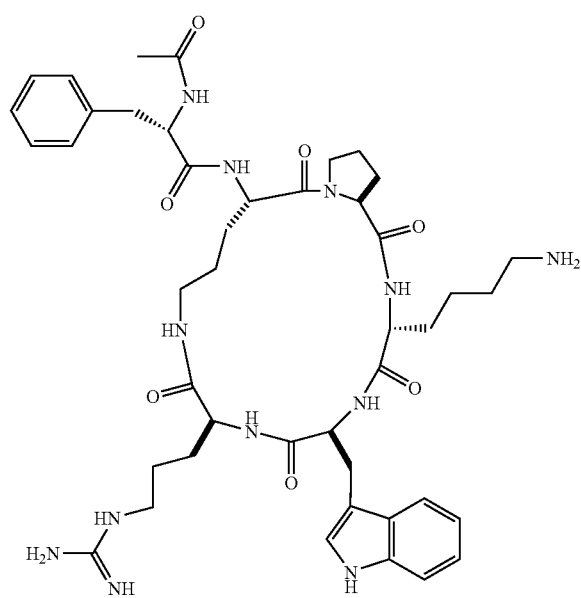
45
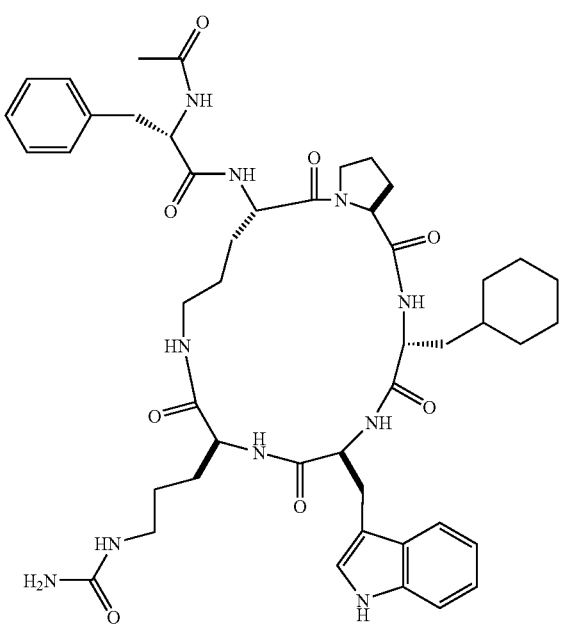

56
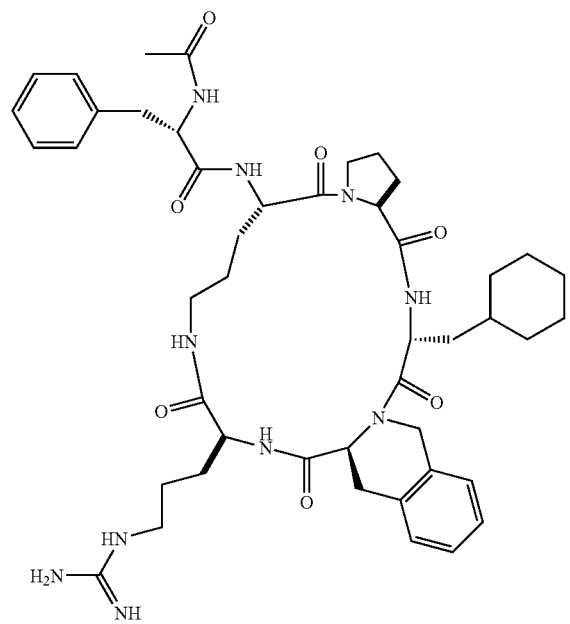
58
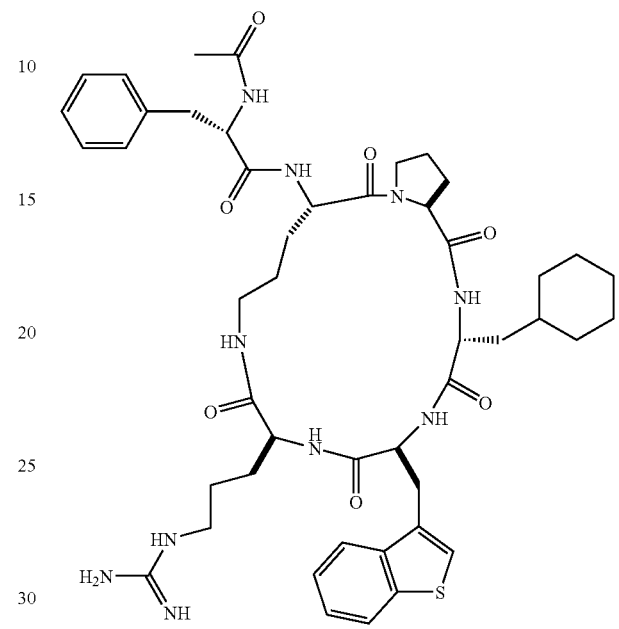
57
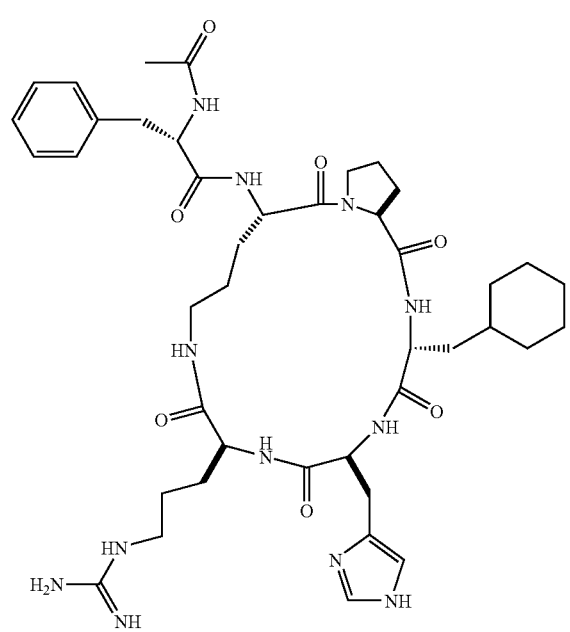
60
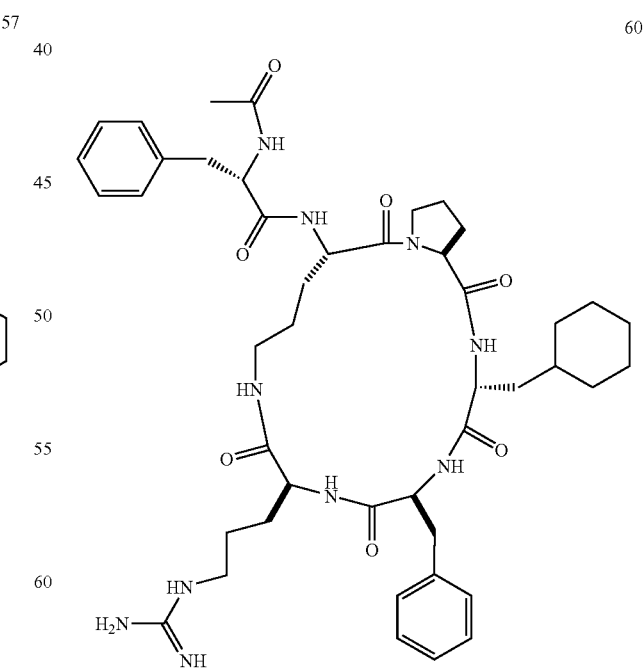

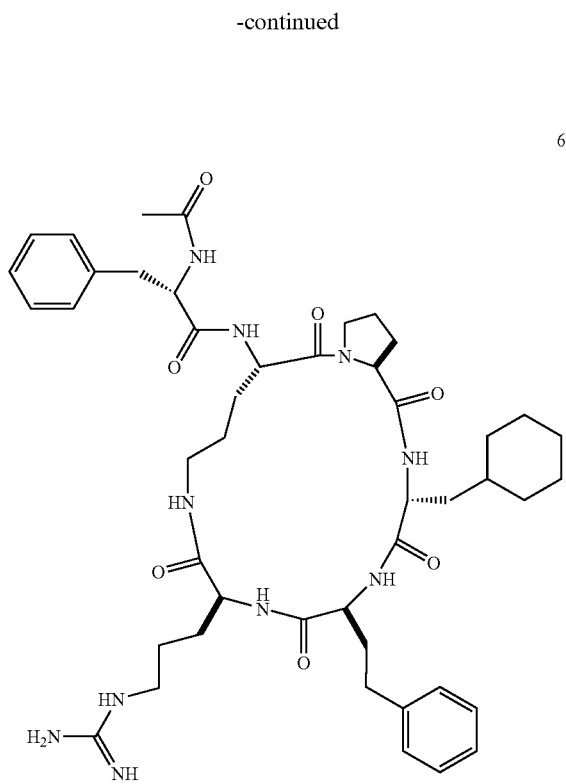

61

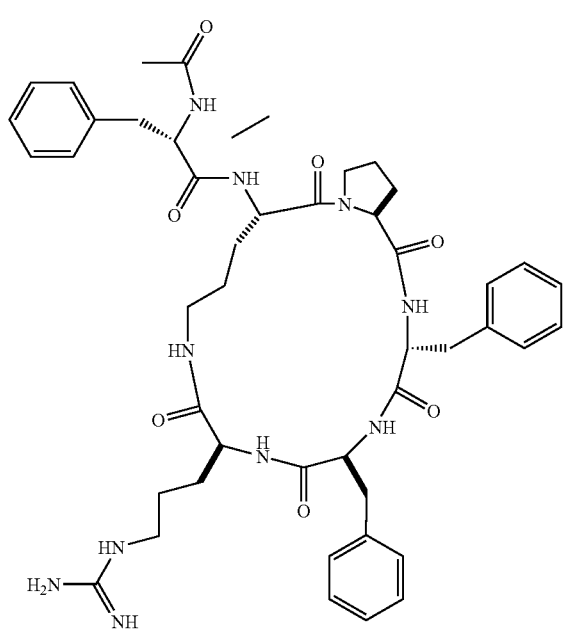

62

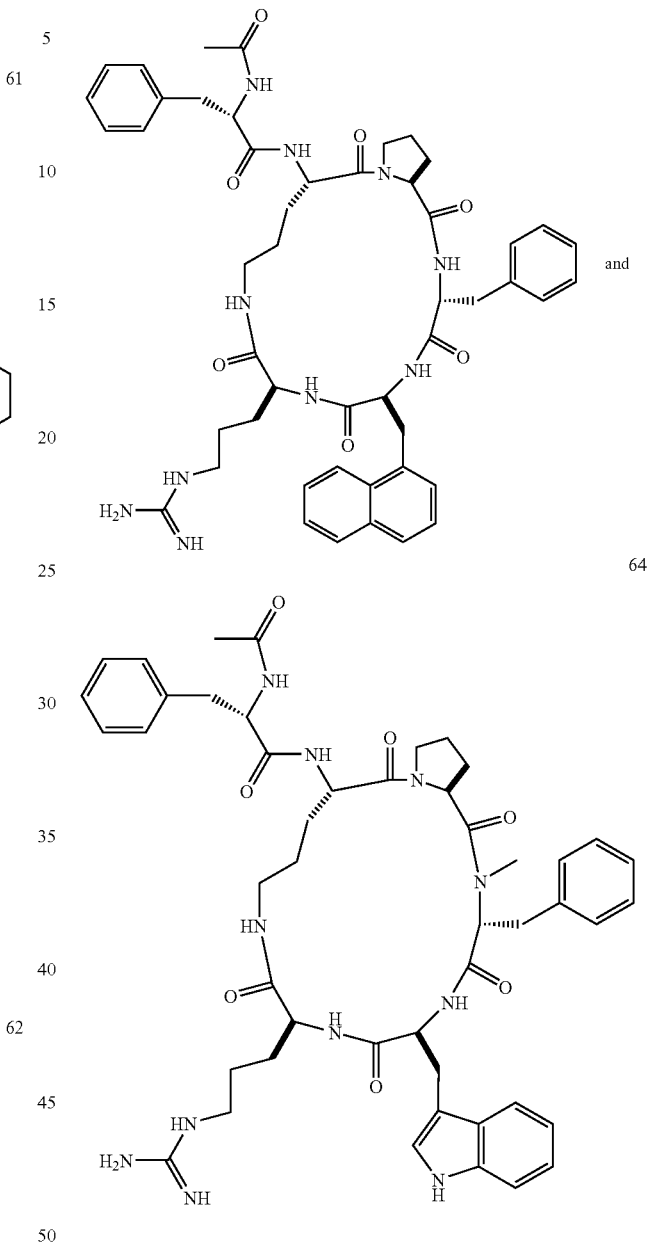

63 and

64

In a particularly preferred embodiment, the compound is PMX53 (compound 1), compound 33, compound 60 or compound 45 illustrated supra.

In a second aspect, the invention provides the use of a compound as defined above in the manufacture of a medicament for the treatment of osteoarthritis.

The inhibitor may be used in conjunction with one or more other agents for the treatment of osteoarthritis, including but not limited to analgesics such as aspirin, corticosteroids such as prednisolone, anti-inflammatory agents, including but not limited to non-steroidal anti-inflammatory agents such as diclofenac, naproxen or ketoprofen, or COX II inhibitors such as Celebrex, Vioxx, Bextra or eterocoxib, meloxicam, carprofen and the like. Other products used to treat osteoarthritis include glycosaminoglycans, pentosan polysulphate, eicosapentanoic acids, omega-3 fatty acids, chondroitin sulphate and glucosamine, and intraarticular injections of hyaluronic acid.

The compositions of the invention may be formulated for oral, parenteral, inhalational, intranasal, rectal or transdermal use, but oral, injectable or percutaneous formulations are preferred. Suitable formulations for administration by any desired route may be prepared by standard methods, for example by reference to well-known textbooks such as Remington: The Science and Practice of Pharmacy, Vol. 11, 2000 (20$^{th}$ edition), A. R. Gennaro (ed), Williams & Wilkins, Pa.

While the invention is not in any way restricted to the treatment of any particular animal or species, it is particularly contemplated that the method of the invention will be useful in medical treatment of humans, and will also be useful in veterinary treatment, particularly of companion animals such as cats, dogs and birds, livestock such as cattle, horses, poultry and sheep, and zoo animals, including non-human primates, large bovids, felids, ungulates and canids.

The compound may be administered at any suitable dose and by any suitable route. Oral, parenteral or topical administration is preferred, because of the greater convenience and acceptability of these routes. It is expected that most if not all compounds of the invention will be stable in the presence of metabolic enzymes, such as those of the gut, blood, lung or intracellular enzymes. Such stability can readily be tested by routine methods known to those skilled in the art.

The effective dose will depend on the nature of the condition to be treated, and the age, weight, and underlying state of health of the individual treatment. This will be at the discretion of the attending physician or veterinarian. Suitable dosage levels may readily be determined by trial and error experimentation, using methods which are well known in the art.

DETAILED DESCRIPTION OF THE INVENTION

Figure 1:
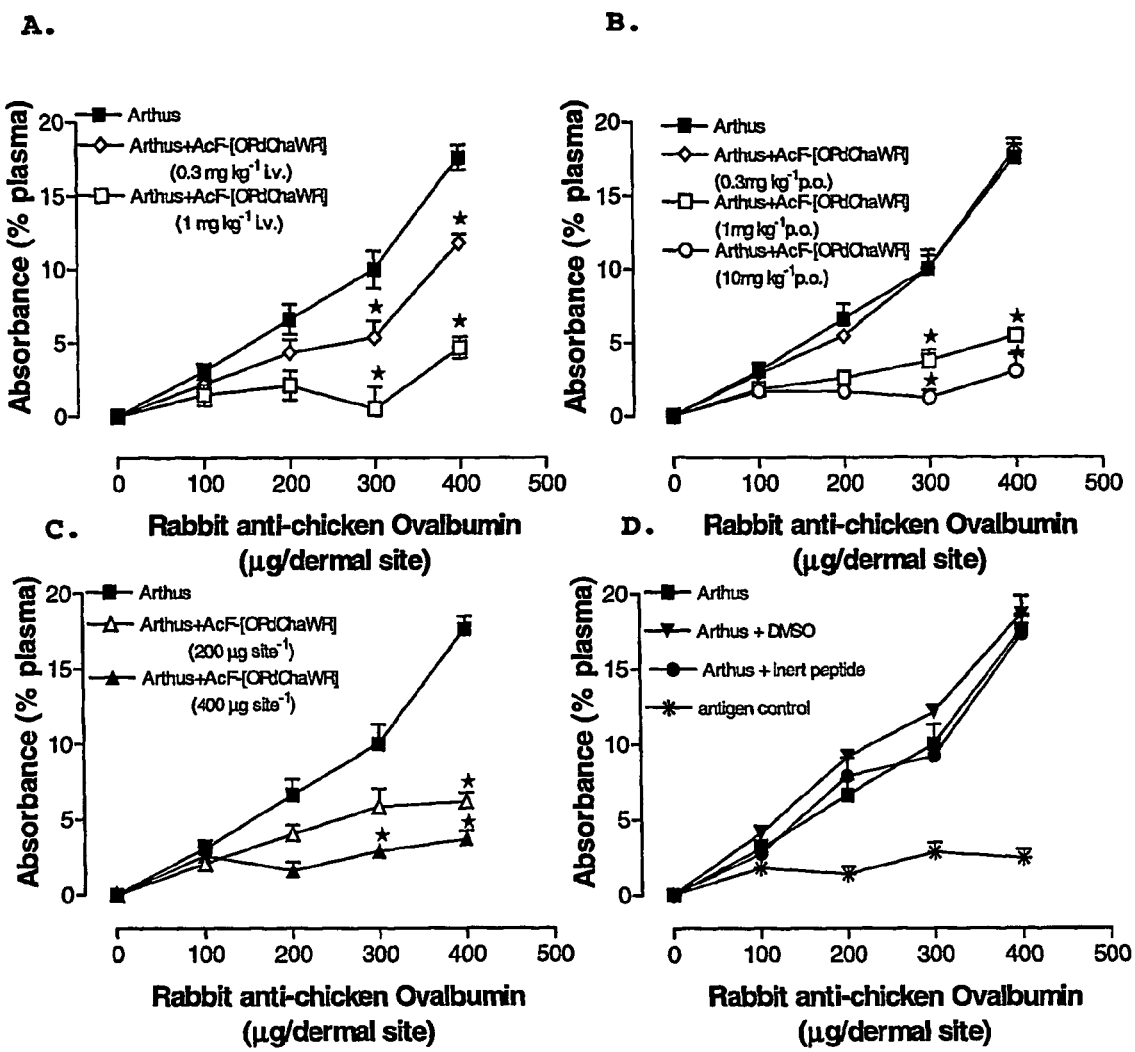
FIG. 1 shows the inhibition of the vascular leakage associated with a dermal Arthus reaction by intravenous (A), oral (B) and topical (C) AcF-[OPdChaWR], and appropriate controls (D).

It is to be clearly understood that this invention is not limited to the particular materials and methods described herein, as these may vary. It is also to be understood that the terminology used herein is for the purpose of describing particular embodiments only, and it is not intended to limit the scope of the present invention, which will be limited only by the appended claims.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

As used herein, the singular forms "a", "an", and "the" include plural reference unless the context clearly dictates otherwise. Thus, for example, a reference to "an enzyme" includes a plurality of such enzymes, and a reference to "an amino acid" is a reference to one or more amino acids. Unless defined otherwise, all technical and scientific terms used herein have the same meaning as commonly understood by one of ordinary skill in the art to which this invention belongs. Although any materials and methods similar or equivalent to those described herein can be used to practice or test the present invention, the preferred materials and methods are now described.

The terms "PMX53" and "3D53" are synonymous, and refer to the cyclic peptide AcF-[OPdChaWR].

Abbreviations used herein are as follows:

D-Cha D-cyclohexylamine

LPS lipopolysaccharide

PMN polymorphonuclear granulocyte rp-HPLC reverse phase-high performance liquid chromatography TFA trifluoroacetic acid;

Cit citrulline dCha D-cyclohexylamine

DPhe D-phenylalanine ip intraperitoneal iv intravenous

LPS lipopolysaccharide

PMN polymorphonuclear granulocyte

PMSF phenylmethylsulfonyl fluoride sc subcutaneous

Throughout the specification conventional single-letter and three-letter codes are used to represent amino acids.

For the purposes of this specification, the term "alkyl" is to be taken to mean a straight, branched, or cyclic, substituted or unsubstituted alkyl chain of 1 to 6, preferably 1 to 4 carbons. Most preferably the alkyl group is a methyl group. The term "acyl" is to be taken to mean a substituted or unsubstituted acyl of 1 to 6, preferably 1 to 4 carbon atoms. Most preferably the acyl group is acetyl. The term "aryl" is to be understood to mean a substituted or unsubstituted homocyclic or heterocyclic aryl group, in which the ring preferably has 5 or 6 members.

A "common" amino acid is a L-amino acid selected from the group consisting of glycine, leucine, isoleucine, valine, alanine, phenylalanine, tyrosine, tryptophan, aspartate, asparagine, glutamate, glutamine, cysteine, methionine, arginine, lysine, proline, serine, threonine and histidine.

An "uncommon" amino acid includes, but is not restricted to, D-amino acids, homo-amino acids, N-alkyl amino acids, dehydroamino acids, aromatic amino acids other than phenylalanine, tyrosine and tryptophan, ortho-, meta- or para-aminobenzoic acid, ornithine, citrulline, canavanine, norleucine, γ-glutamic acid, aminobutyric acid, L-fluorenylalanine, L-3-benzothienylalanine, and α,α-disubstituted amino acids.

Generally, the terms "treating", "treatment" and the like are used herein to mean affecting a subject, tissue or cell to obtain a desired pharmacological and/or physiological effect. The effect may be prophylactic in terms of completely or partially preventing a disease or sign or symptom thereof, and/or may be therapeutic in terms of a partial or complete cure of a disease.

"Treating" as used herein covers any treatment of, or prevention of disease in a vertebrate, a mammal, particularly a human, and includes: preventing the disease from occurring in a subject who may be predisposed to the disease, but has not yet been diagnosed as having it; inhibiting the disease, ie., arresting its development; or relieving or ameliorating the effects of the disease, ie., cause regression of the effects of the disease.

The invention includes the use of various pharmaceutical compositions useful for ameliorating disease. The pharmaceutical compositions according to one embodiment of the invention are prepared by bringing a compound of formula I, analogue, derivatives or salts thereof and one or more pharmaceutically-active agents or combinations of compound of formula I and one or more pharmaceutically-active agents into a form suitable for administration to a subject using carriers, excipients and additives or auxiliaries.

Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 20th ed. Williams & Wilkins (2000) and The British National Formulary 43rd ed. (British Medical Association and Royal Pharmaceutical Society of Great Britain, 2002; http://bnf.rhn.net), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed., 1985).

The pharmaceutical compositions are preferably prepared and administered in dosage units. Solid dosage units include tablets, capsules and suppositories. For treatment of a subject, depending on activity of the compound, manner of administration, nature and severity of the disorder, age and body weight of the subject, different daily doses can be used. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of the cytotoxic side effects. Various considerations are described, eg. in Langer, Science, 249: 1527, (1990). Formulations for oral use may be in the form of hard gelatin capsules, in which the active ingredient is mixed with an inert solid diluent, for example, calcium carbonate, calcium phosphate or kaolin. They may also be in the form of soft gelatin capsules, in which the active ingredient is mixed with water or an oil medium, such as peanut oil, liquid paraffin or olive oil.

Aqueous suspensions normally contain the active materials in admixture with excipients suitable for the manufacture of aqueous suspensions. Such excipients may be suspending agents such as sodium carboxymethyl cellulose, methyl cellulose, hydroxypropylmethylcellulose, sodium alginate, polyvinylpyrrolidone, gum tragacanth and gum acacia; dispersing or wetting agents, which may be (a) a naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleaginous suspension. This suspension may be formulated according to known methods using suitable dispersing or wetting agents and suspending agents such as those mentioned above. The sterile injectable preparation may also be a sterile injectable solution or suspension in a non-toxic parenterally-acceptable diluent or solvent, for example, as a solution in 1,3-butanediol. Among the acceptable vehicles and solvents which may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid may be used in the preparation of injectables.

Compounds of formula I may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Dosage levels of the compound of formula I of the present invention will usually be of the order of about 0.5 mg to about 20 mg per kilogram body weight, with a preferred dosage range between about 0.5 mg to about 10 mg per kilogram body weight per day (from about 0.5 g to about 3 g per patient per day). The amount of active ingredient which may be combined with the carrier materials to produce a single dosage will vary, depending upon the host to be treated and the particular mode of administration. For example, a formulation intended for oral administration to humans may contain about 5 mg to 1 g of an active compound with an appropriate and convenient amount of carrier material, which may vary from about 5 to 95 percent of the total composition. Dosage unit forms will generally contain between from about 5 mg to 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

In addition, some of the compounds of the invention may form solvates with water or common organic solvents. Such solvates are encompassed within the scope of the invention.

The compounds of the invention may additionally be combined with other therapeutic compounds to provide an operative combination. It is intended to include any chemically compatible combination of pharmaceutically-active agents, as long as the combination does not eliminate the activity of the compound of formula I of this invention.

In evaluation of the compounds of the invention, conventional measures of efficacy of treatment of osteoarthritis may be used. For example, commonly-used primary efficacy endpoints include the Western Ontario and McMaster's University Osteoarthritis Index (WOMAC) Pain subscale, Patient Global Assessment of Response to Therapy, Investigator Global Assessment of Disease Status, McGill pain questionnaire, Modified Stanford Health Assessment Questionnaire (MHAQ), Health Assessment Questionnaire and Kellgren-Lawrence radiographic grading.

Methods are also available for monitoring the progression of osteoarthritis using biomarkers, such as detection of collagen breakdown products (IBEX technologies, Inc, Toronto), or aggrecan fragments (U.S. Pat. No. 5,935,796 by The University of melbourne).

General Methods

Cyclic peptide compounds of formula I are prepared according to methods described in detail in our earlier applications No. PCT/AU98/00490 and PCT/AU02/01427. An alternative method of synthesis is described in our Australian provisional application No. 2003902743. The entire disclosures of these specifications are incorporated herein by this reference. While the invention is specifically illustrated with reference to the compound AcF-[OPdChaWR] (PMX53), whose corresponding linear peptide is Ac-Phe-Orn-Pro-dCha-Trp-Arg, it will be clearly understood that the invention is not limited to this compound.

Compounds 1-6, 17, 20, 28, 30, 31, 36 and 44, shown above (and also disclosed in International Patent Application No. PCT/AU98/00490) and compounds 10-12, 14, 15, 25, 33, 35, 40, 45, 48, 52, 58, 60, 66, and 68-70, also shown above and disclosed for the first time in Australian PCT International Patent Application No. PCT/AU02/01427 have appreciable antagonist potency ($IC_{50}$<1 μM) against the C5a receptor on human neutrophils. The compounds shown below, PMX53 (compound 17), also disclosed in International Patent Application No. PCT/AU98/00490 and identified as compound 1 in International Patent Application No. PCT/AU02/014271) and compounds 33, 45 and 60 herein are most preferred:

-continued

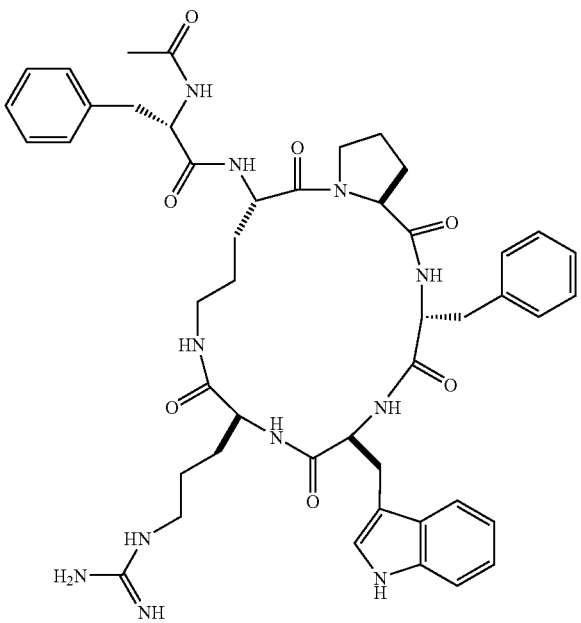

33

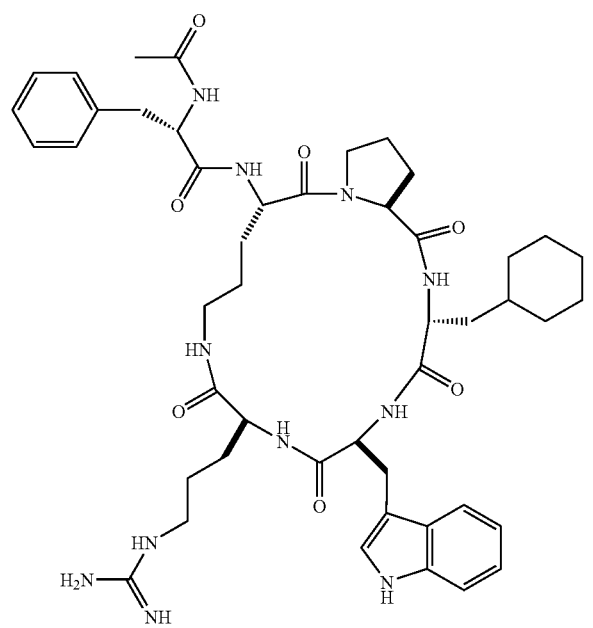

1

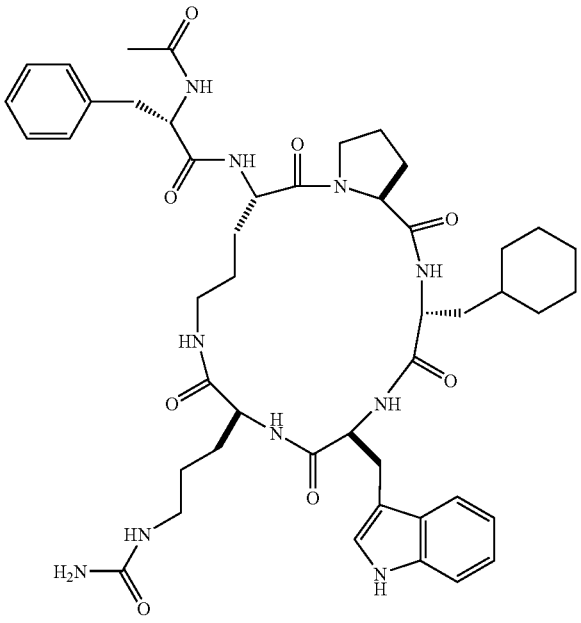

45

-continued

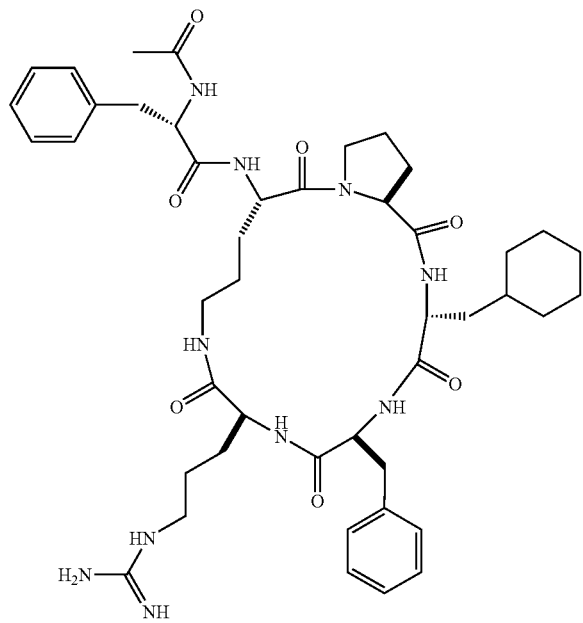

We have found that all of the compounds of formula I which have so far been tested have broadly similar pharmacological activities, although the physicochemical properties, potency, and bioavailability of the individual compounds varies somewhat, depending on the specific substituents.

The following general tests may be used for initial screening of candidate inhibitor of G protein-coupled receptors, and especially of C5a receptors.

Receptor-Binding Assay

Assays are performed with fresh human PMNs, isolated as previously described (Sanderson et al. 1995) using a buffer of 50 mM HEPES, 1 mM $CaCl_2$, 5 mM $MgCl_2$, 0.5% bovine serum albumin, 0.1% bacitracin and 100 µM phenylmethylsulfonyl fluoride (PMSF). In assays performed at 4° C., buffer, unlabelled human recombinant C5a (Sigma) or peptide, Hunter/Bolton labelled $^{125}$I-C5a (~20 pM) (New England Nuclear, Mass.) and PMNs ($0.2 \times 10^6$) are added sequentially to a Millipore Multiscreen assay plate (HV 0.45) having a final volume of 200 µL/well. After incubation for 60 min at 4° C., the samples are filtered and the plate washed once with buffer. Filters are dried, punched and counted in an LKB gamma counter. Non-specific binding is assessed by the inclusion of 1 mM peptide or 100 nM C5a, which typically results in 10-15% total binding.

Data are analysed using non-linear regression and statistics with Dunnett post-test.

Myeloperoxidase Release Assay for Antagonist Activity

Cells are isolated as previously described (Sanderson et al, 1995) and incubated with cytochalasin B (5 µg/mL, 15 min, 37° C.). Hank's Balanced Salt solution containing 0.15% gelatin and peptide is added on to a 96 well plate (total volume 100 µL/well), followed by 25 µL cells ($4 \times 10^6$/mL). To assess the capacity of each peptide to antagonize C5a, cells are incubated for 5 min at 37° C. with each peptide, followed by addition of C5a (100 nM) and further incubation for 5 min. Then 50 µL of sodium phosphate (0.1M, pH 6.8) is added to each well, the plate was cooled to room temperature, and 25 µL of a fresh mixture of equal volumes of dimethoxybenzidine (5.7 mg/mL) and $H_2O_2$ (0.51%) is added to each well. The reaction is stopped at 10 min by addition of 2% sodium azide. Absorbances are measured at 450 nm in a Bioscan 450 plate reader, corrected for control values (no peptide), and analysed by non-linear regression.

The invention will now be described by way of reference only to the following general methods and experimental examples.

Example 1

Reverse Passive Arthus Reaction in the Rat

A reverse passive peritoneal Arthus reaction was induced as previously described (Strachan et al., 2000), and a group of rats were pretreated prior to peritoneal deposition of antibody with AcF-[OPdChaWR] (1) by oral gavage (10 mg kg$^{-1}$, dissolved in 10% ethanol/90% saline solution to a final volume of 200 µl) or an appropriate oral vehicle control 30 min prior to deposition of antibody. Female Wistar rats (150-250 g) were anaesthetised with ketamine (80 mg kg$^{-1}$ i.p.) and xylazine (12 mg kg$^{-1}$ i.p.).

The lateral surfaces of the rat were carefully shaved and 5 distinct sites on each lateral surface clearly delineated. A reverse passive Arthus reaction was induced in each dermal site by injecting Evans blue (15 mg kg$^{-1}$ i.v.), chicken ovalbumin (20 mg kg$^{-1}$ i.v.) into the femoral vein 10 min prior to the injection of antibody. Rabbit anti-chicken ovalbumin (saline only, 100, 200, 300 or 400 µg antibody in a final injection volume of 30 µL) was injected in duplicate at two separate dermal sites on each lateral surface of the rat, giving a total of 10 injection sites per rat. Rats were placed on a heating pad, and anaesthetic was maintained over a 4 h-treatment period with periodic collection of blood samples. Blood was allowed to spontaneously clot on ice, and serum samples were collected and stored at −20° C. Four hours after induction of the dermal Arthus reaction, the anaesthetised rat was euthanased and a 10 mm$^2$ area of skin was collected from the site of each Arthus reaction. Skin samples were stored in 10% buffered formalin for at least 10 days before histological analysis using haematoxylin and eosin stain. Additionally, a second set of skin samples were placed in 1 mL of formamide overnight, and the absorbance of Evans blue extraction measured at 650 nm, as an indicator of serum leakage into the dermis. FIG. 1 shows the optical density of dermal punch extracts following intradermal injection of rabbit anti-chicken ovalbumin at 0-400 µg site$^{-1}$ following pretreatment with AcF-[OPdChaWR] intravenously, orally or topically. Data are shown as absorbance at 650 nm as a percentage of the plasma absorbance, as mean values SEM (n=3-6). *indicates a P value ≦0.05 when compared to Arthus control values.

Rats were pretreated with the C5aR antagonist, AcF-[OPdChaWR] (1) as the TFA salt, either intravenously (0.3-1 mg kg$^{-1}$ in 200 L saline containing 10% ethanol, 10 min prior to initiation of dermal Arthus), orally (0.3-10 mg kg$^{-1}$ in 200 µL saline containing 10% ethanol by oral gavage, 30 min prior to initiation of dermal Arthus in rats denied food access for the preceding 18 hours) or topically (200-400 µg site$^{-1}$ 10 min prior to initiation of dermal Arthus reaction), or with the appropriate vehicle control. Topical application of the antagonist involved application of 20 g of a 10-20 mg mL$^{-1}$ solution in 10% dimethyl sulphoxide (DMSO), which was then smeared directly onto the skin at each site, 10 min prior to induction of the Arthus reaction.

The saline-only injection site from rats treated with Evans blue only served as antigen controls, the saline-only injection site from rats treated with Evans blue plus topical DMSO only served as a vehicle control, the saline-only injection site from rats treated with Evans blue plus either intravenous, oral or topical antagonist only served as antagonist controls, and Evans blue plus dermal rabbit anti-chicken ovalbumin served as antibody controls. Topical application of the peptide AcF-[OPGWR] which has similar chemical composition and solubility to AcF-[OPdChaWR] (1), but with an $IC_{50}$ binding affinity of >1 mM in isolated human PMNs, served as an inactive peptide control. AcF-[OPGWR] was also dissolved in 10% DMSO and applied topically at 400 μg per site 10 min prior to initiation of the Arthus reaction.

TNFα Measurement

Figure 2:
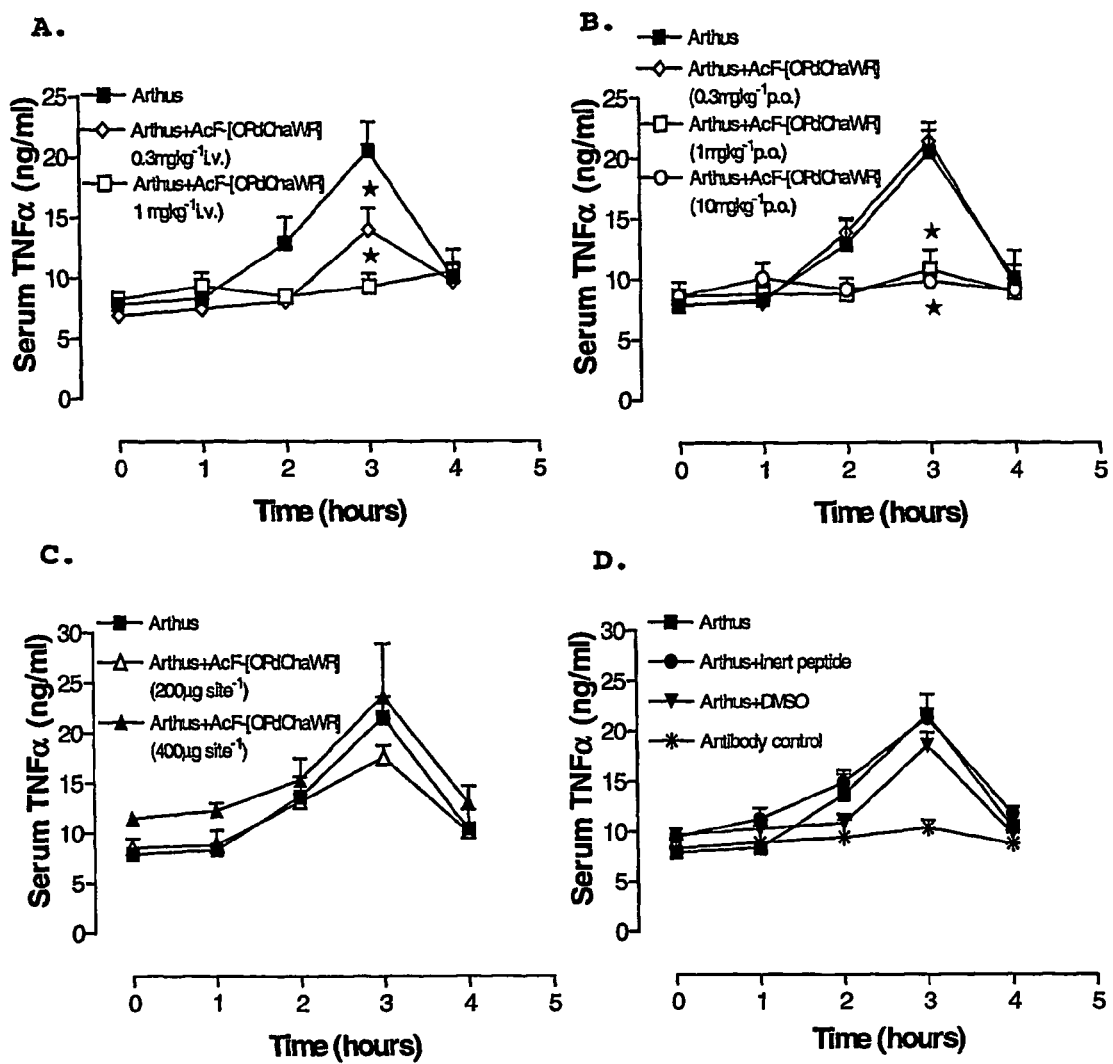
FIG. 2 shows the inhibition of the rise in circulating TNFα associated with a dermal Arthus reaction by intravenous (A), oral (B) and topical (C) AcF-[OPdChaWR], and appropriate topical controls (D).

Serum TNFα concentrations were measured using an enzyme-linked immunosorbent assay (ELISA) kit (Strachan et al., 2000). Antibody pairs used were a rabbit anti-rat TNFα antibody coupled with a biotinylated murine anti-rat TNFα antibody. FIG. 2 shows the serum TNFα concentrations at regular intervals after initiation of a dermal Arthus reaction, with group of rats pretreated with AcF-[OPdChaWR] intravenously, orally or topically. Data are shown as mean values SEM (n=3-6). *indicates a P value of ≦0.05 when compared to Arthus control values.

Interleukin-6 Measurement

An ELISA method as described previously was used to measure serum and peritoneal lavage fluid interleukin-6 (IL-6) concentrations (Strachan et al., 2000).

Pathology Assessment

Figure 3:
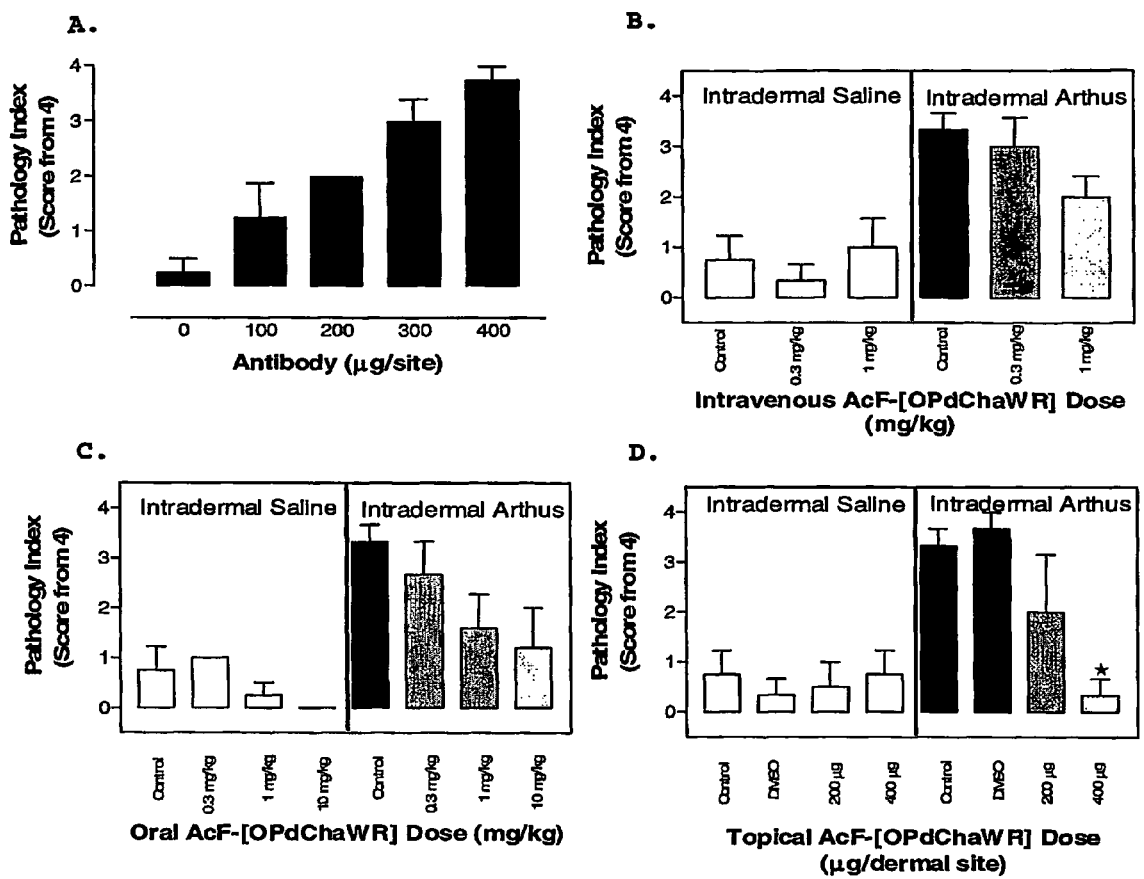
FIG. 3 shows the reduction of the pathology index associated with a dermal Arthus reaction by intravenous, oral and topical AcF-[OPdChaWR].

Rat skin samples were fixed in 10% buffered formalin for at least 10 days, and stained with haematoxylin and eosin using standard histological techniques. Dermal samples were analysed in a blind fashion for evidence of pathology, and the degree of rat PMN infiltration was scored on a scale of 0-4. Initiation of a dermal Arthus reaction resulted in an increase in interstitial neutrophils, which was quantified in the following manner. Sections were given a score of 0 if no abnormalities were detected. A score of 1 indicated the appearance of increased PMNs in blood vessels, but no migration of inflammatory cells out of the lumen. A score of 2 and 3 indicated the appearance of increasing numbers of PMNs in the interstitial tissue and more prominent accumulations of inflammatory cells around blood vessels. A maximal score of 4 indicated severe pathological abnormalities were present in dermal sections, with excessive infiltration of PMNs into the tissues and migration of these cells away from blood vessels. FIG. 3 shows the intradermal injection of increasing amounts of antibody leads to a dose-responsive increase in the pathology index scored by dermal samples (A). Data are shown for dermal samples intradermally injected with saline or 400 μg site$^{-1}$ antibody (n=5) in rats pretreated with AcF-[OPdChaWR] intravenously (B) (n=3), orally (C) (n=3) and topically (D) (n=3). Data are shown as mean values±SEM. * P≦0.05 when compared to Arthus values using a non-parametric t-test.

Example 2

Rat Monoarticular Antigen-Induced Arthritis

Female Wistar rats (150-250 g) were obtained from the Central Animal Breeding House, University of Queensland. Methylated bovine serum albumin (mBSA) (0.5 mg) was dissolved in Freund's complete adjuvant (0.5 mg) and sonicated to produce a homogenous suspension. Each rat received a subcutaneous injection of this suspension (0.5 mL) on days 1 and 7. On day 12-28, rats were separated into separate cages, and body weight and food and water intake monitored daily. Rats received either ordinary tap water or drinking water containing AcF-[OPdChaWR] (1). Body weight and water intake were monitored daily, and rats received a daily dose of 1 mg/kg/day of the C5aR antagonist AcF-[OPd-ChaWR] (1) for days 12-28 of the trial. On day 14, rats were anaesthetised and their hind limbs shaven. Each rat received an intra-articular (100 μl) injection of mBSA (0.5 mg) in the left knee, and saline in the right knee. The saline only knee from rats receiving normal drinking water served as a saline control, the saline only knee from rats receiving AcF-[OPd-ChaWR] (1) in the drinking water served as an antagonist control.

Rats were euthanased on day 28, and whole blood collected into an Eppendorf tube and allowed to spontaneously clot on ice. Blood samples were centrifuges (11,000 rpm×3 min) and serum collected and stored at −20° C. until analysis of serum cytokines using an ELISA. Each knee capsule was lavaged with 100 μL saline, and the total cell count determined using a haemocytometer. In addition, an aliquot of the knee joint lavage fluid was dropped onto a glass slide, and allowed to air dry. Once dry, cells were stained with a differential stain (Diff Quick) and a differential cell count was performed using a 40× dry lens microscope. The remaining lavage fluids from each joint were stored at −20° C. until later analysis of intra-articular cytokine levels using an ELISA. Each knee joint was severed, trimmed leaving only the area of interest and the skin was split with a scalpel blade. Knee samples were stored in 10% buffered formalin for >10 d. Knees were then rinsed with distilled water and placed in a saturated solution of EDTA solution for 21 d for decalcification before being embedded in paraffin wax.

Knee tissue samples were prepared using standard histological techniques as described in Example 1, and stained using an haematoxylin and eosin stain. Histological slides were analysed in a blind fashion. Tissue sections were scored from 0-4, with a score of 0 indicating the detection of no abnormalities, and increasing scores with the appearance of synovial cell proliferation, inflammatory cell infiltration, cartilage destruction and haemorrhage.

In no samples was there evidence of significant bone erosion. Samples were thawed on the day of ELISA analysis, and serum or intra-articular lavage fluid TNFα and IL-6 concentrations were determined from a standard curve, using an ELISA as described in Example 1.

Figure 4:
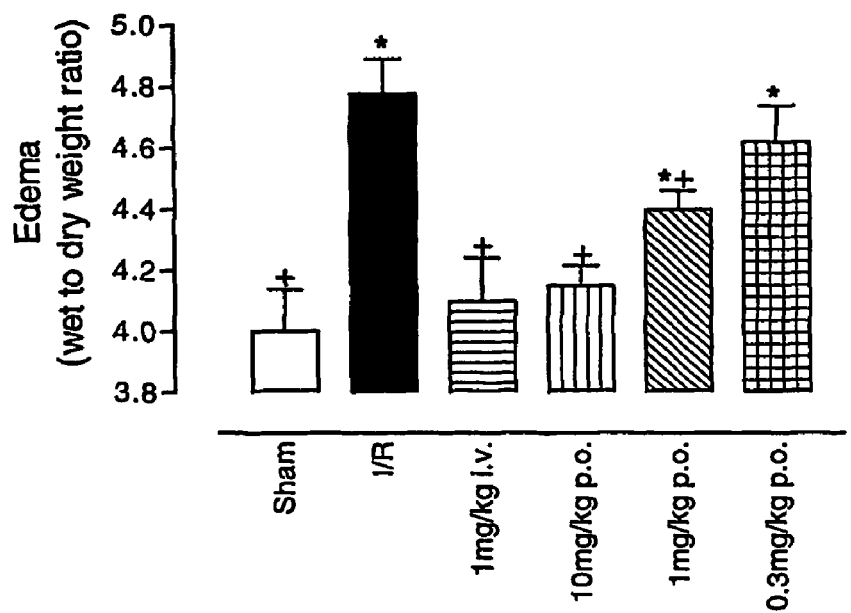
FIG. 4 shows the inhibition of arthritic right knee joint swelling by AcF-[OPdChaWR] given orally on Days-2 to +14.
Figure 5:
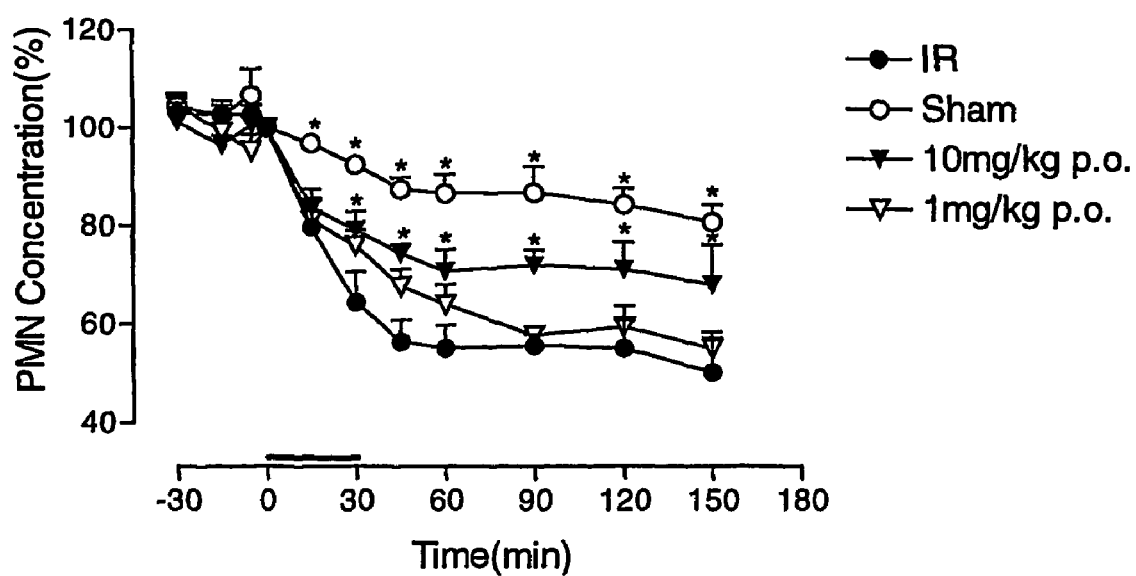
FIG. 5 shows the inhibition of right knee joint TNFα and IL-6 levels in joint lavage. "Untreated" refers to an animal not treated with AcF-[OPdChaWR], but with its right knee challenged with antigen following sensitisation.

FIG. 4 shows the inhibition of arthritic right knee joint swelling by AcF-[OPdChaWR] given orally on Days-2 to +14, while FIG. 5 shows the inhibition of right knee joint TNF-α and IL-6 levels in joint lavage. "Untreated" refers to an animal not treated with AcF-[OPdChaWR], but with its right knee challenged with antigen following sensitisation.

Example 3

The Effect of PMX53 on Induced Osteoarthritis in Dogs

Four healthy dogs were obtained from a group of pound dogs destined for euthanasia. The dogs were acclimatised to the experimental canine ward for 7 days before the experiment commenced. Dogs were housed individually and fed on a mixture of dry dog food, canned dog food and occasional raw bones. They were walked for 10 minutes twice daily throughout the trial. The dogs were of age and sex as follows:

Dog #2 Male cattle dog (approximately 1 year old)

Dog #3 Female cattle dog (1-2 years old)

Dog #4 Female bull terrier cattle dog cross (2 years old)

Dog #5 Female whippet cross (less than 1 year old)

PMX53 was synthesised by the Institute of Molecular Bioscience at the University of Queensland. The drug was dissolved in 30% polyethylene glycol 400 (PEG 400) in normal saline. The solution was made to a concentration of 3 mg/ml. The placebo vehicle was 30% PEG 400 in saline. All treatments were sterilised by filtration and stored at 4° C. The dogs were given the drug or placebo at a dose rate of 1 ml/10 kg body weight. The treatments were assigned to the dogs in a random fashion. The drug containers were marked so that the attendants who scored the gait were unaware of the treatment given to each dog.

The cruciate ligament of the left stifle (knee) joint was transected surgically by an experienced specialist surgeon. The incision in the skin was approximately 2 centimeters long. The dogs were given postoperative pain relief, including epidural analgesia and opioids. At 24 hours after the surgery all dogs were limping. No supplementary analgesic therapy was deemed necessary after day 1. All dogs tolerated the procedure very well.

The drug was given as a subcutaneous injection (0.3 mg/kg) into the loose skin on the dorsum of the neck once daily. The drug and placebo caused mild discomfort when injected, but the dogs were readily distracted with food at the time of injection. Dogs were assessed twice daily for lameness while they were walked. The scoring was done by at least two people.

Figure 6A:
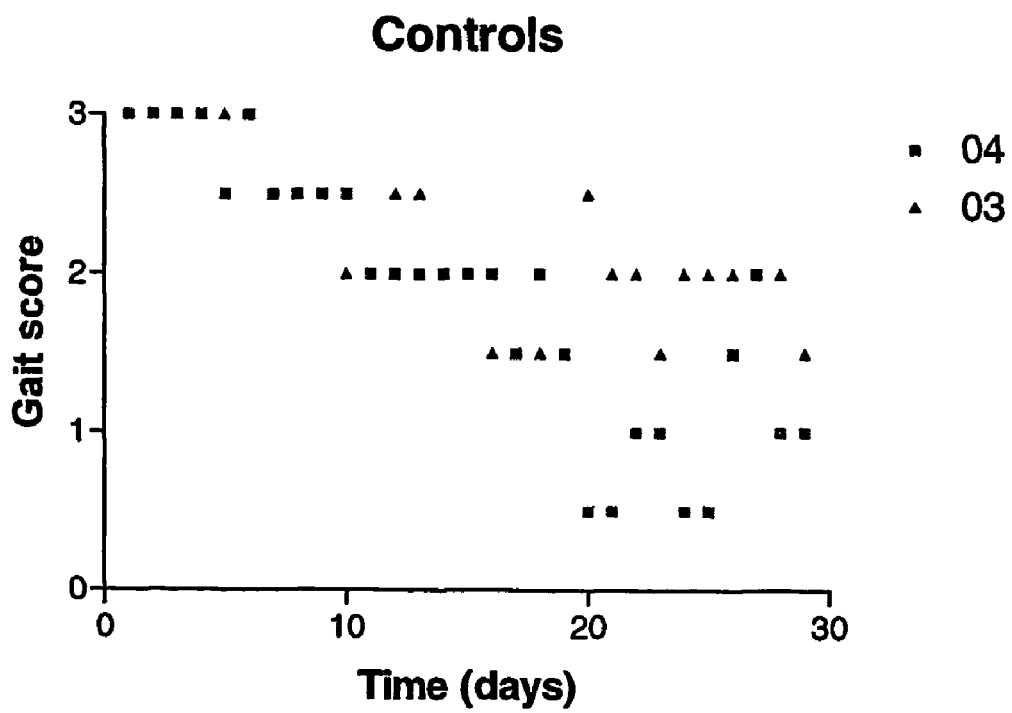
FIG. 6a summarises the gait scores of dogs (n=2) treated with placebo after transection of the cruciate ligament.

The dogs treated with placebo showed an improvement in gait between 10 and 13 days after surgery, as shown in FIG. 6a. This was regarded as a natural recovery from the injury. They never returned to complete soundness.

Figure 6B:
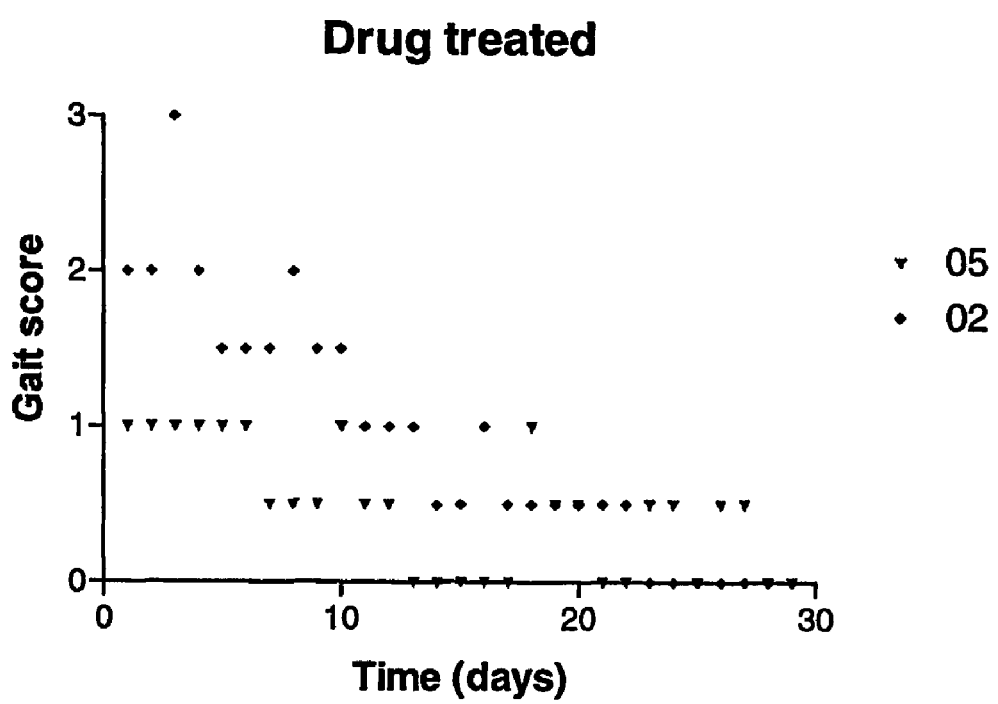
FIG. 6b summarises the gait score of dogs (n=2) treated with PMX53 (0.3 mg/kg subcutaneously once a day) after transection of the cruciate ligament.

In contrast to the controls, drug-treated dogs showed improvement in the degree of lameness after 4-6 days' treatment, ie more rapidly than controls, as illustrated in FIG. 6b.

The dogs maintained the improved gait for the next 3 weeks until the end of the trial. These two dogs were relatively sound at the end of the trial.

The dogs were euthanased at day 28. All dogs had complete disruption of the anterior cruciate ligament in the left knee, and all had thickening of the joint capsule and increased volume of joint fluid in the left knees. There were tags of fibrin adhering to the synovium in all affected joints. There was mild cartilage erosion in dog #2 (drug treated) and dog #4 (placebo). The site of injection showed no abnormalities.

Figure 7:
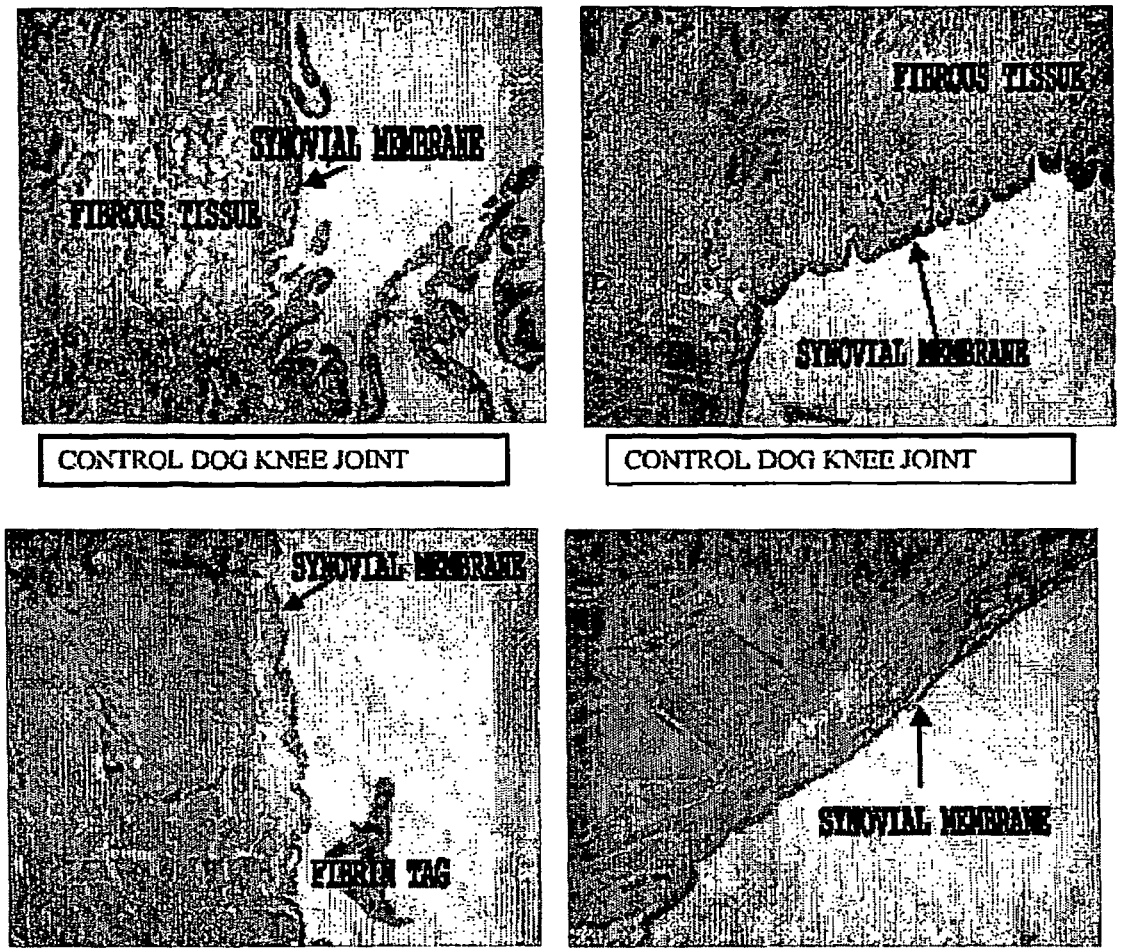
FIG. 7 compares the histological appearance of knee joints from control and PMX-53 (3D53)-treated dogs.

The joints were X-rayed before surgery and after death. No significant bony lesions were detected at either time point. Blood was collected for biochemistry and haematology before surgery and at day 28. No abnormalities were detected in any dog at either time point. The histopathology of the joint showed that there was reduced thickening of the synovial membrane and reduced fibrosis of the drug-treated dogs compared to the arthritic controls. This is illustrated in FIG. 7. The clinical impression was the drug clearly improved the ability of the dogs to walk. The drug-treated dogs walked strongly on the affected leg from approximately one week after surgery and the commencement of treatment. It should be noted that both these dogs had a lower starting score than the two placebo-treated dogs.

The placebo-treated dogs improved slowly, so that by 4 weeks they were noticeably less lame than at the start of the trial. This is consistent with observations from clinical practice; small animals with ruptured cruciate ligaments frequently recover without surgery.

Example 4

Clinical Trial of PMX53 in Arthritic Dogs

A clinical trial of the effect of PMX53 in dogs with osteoarthritis was carried out. Some animals were treated with PMX53 at the Small Animal Clinic at the Veterinary School, University of Queensland, and one of the inventors has also been using PMX53 to treat one of his own dogs. We have been limited by the small amount of drug available, so that the dogs have been given PMX53 orally, or as a low dose subcutaneous injection. A single oral dose of the drug appears to be effective for at least 3-4 days, even in the most severe case. The effects of one injection last for weeks. No side effects have been observed up to 12 months treatment. The individual cases are listed below.

Case #1

A 15 year old blue cattle dog had a history of lameness and morning stiffness which had been present for 4 years, and was diagnosed as osteoarthritis using normal clinical criteria. Contributing causes of the osteoarthritis included a forelimb fracture and the advanced age of the dog. For the first 3 years after lameness developed, the dog was treated once daily with celery seed (3G equivalent of celery seed=1 tablet), and when arthritis was severe twice daily (1 tablet morning and night). There was a noticeable decrease in lameness with this treatment.

PMX53 treatment was commenced in October 2002, when the dog showed marked deterioration in the lameness. The dog was then 14 years and 10 months old. PMX53 was initially administered orally at 1 mg/kg once daily, then 0.3 mg/kg as a subcutaneous injection given once daily for a week. Celery seed was stopped at this point.

The improvement after both oral and subcutaneous treatment was marked. The dog showed no morning stiffness, could run and play, and showed a dramatic improvement in attitude. The dog showed much more interest in food and was considered to have a better quality of life. The range of joint movement was not improved, but there was no joint pain on manipulation.

The frequency of injections was reduced to once a week, but after a few weeks it became evident that injections could be administered as required, ie when the dog started to show lameness. As at October 2003 the animal has received injections for 12 months, and currently the frequency of administration is once every 4 to 6 weeks. There is a very noticeable improvement in the condition within 24 hours of the injection of PMX53 (0.3 mg/kg subcutaneously). There have been no apparent side effects.

Case #2

A Rottweiler bitch of approximately 4 years old had been treated for a variety of orthopaedic conditions. She had undergone bilateral triple wedge osteotomy for hereditary congenital hip dysplasia and repair of a ruptured cruciate ligament in one stifle, and she had an unrepaired ruptured cruciate in another. Hip dysplasia is a congenital malformation of the acetabulum of the hip joint, which leads to osteoarthritis of the joint. These conditions had resulted in the development of degenerative joint disease (osteoarthritis) in many joints. The animal was very lame, and required continuing medication with NSAIDs (meloxicam).

The dog was treated with PMX53, initially at 1 mg/kg orally for 4 weeks, then with injected PMX53 (0.3 mg/kg sc)

once daily. The dog's owner scored the degree of lameness daily. The lameness did not improve, but the owners reported that the dog showed a noticeable improvement in attitude, and had started playing with the other dog in the household. It was considered in this case that the severe structural changes in the joints, resulting from both the hereditary congenital hip dysplasia and the ligament rupture, were causing the lameness, but that PMX53 therapy was reducing the pain and improving the well being of the dog. The PMX53 treatment was discontinued after 6 weeks because of limited availability of the drug.

Case #3

A cattle dog had suffered an autoimmune arthritis as a puppy, which had "burned out" and left the dog with osteoarthritic changes in many joints. The dog was on NSAID therapy (meloxicam) for control of pain, and its condition was deteriorating. The dog was started on PMX53 (1 mg/kg per day orally) in January 2003. The regimen was changed after 1 month to subcutaneous injections as required. This dog has responded very well to therapy, and has had no NSAIDs since it has been on PMX53. The dog currently receives an injection of PMX53 (0.3 mg/kg sc) every one to 2 weeks when the owner notices a deterioration in his condition. There have been no side effects after 9 months of treatment. The owner, who is a veterinarian, rates PMX53 as being superior to any commercially-available treatment for osteoarthritis in dogs.

Case #4

A cocker spaniel was diagnosed with rheumatoid arthritis, which is a condition rarely found in dogs. This presented as a severe polyarthritis which required aggressive corticosteroid therapy (5 mg prednisolone twice daily). In January 2003 the dog was commenced on PMX53 (1 mg/kg daily PO followed by 0.3 mg/kg twice a week). The prednisolone therapy was slowly reduced over 6 months to see if the dog could be maintained on PMX53 alone. PMX53 (0.3 mg/kg SC) once a week did not completely control the clinical signs. When the dog was also given prednisolone (2.5 mg PO once every second day) with PMX53 once a week, excellent results were obtained. In this case of aggressive, active disease treatment with PMX53 has allowed the dose of corticosteroid to be substantially reduced, a very desirable outcome. The dog continues to be treated with PMX53 and the reduced dose of prednisolone (October 2003).

Example 5

Comparison of Drug Efficacy in Rats

One cruciate ligament of each rat is surgically severed to create osteoarthrits in a knee joint. The contralateral knee joint is untreated, and is used as a control. Once the condition is clearly established (approximately 4 weeks), the animals are divided into groups, and one group each is treated with PMX53, meloxicam, chondroitin sulphate or pentosan polysulphate for 28 days. The comparator treatments are commonly used in veterinary practice to treat degenerative joint disease in dogs.

Disease progression and the effects of drug treatment are determined by scoring the animal's gait, measuring joint swelling, and determination of synovial and plasma cytokine TNF-α levels. The rats are euthanased 8 weeks after the commencement of the experiment, and post mortem examination of gross and microscopic pathology of the treated and control knee joints is performed.

Example 6

Multi-Centre Trial in Dogs

A blinded crossover trial to compare PMX53 with NSAID is performed. A total of 40-50 dogs which fulfil the diagnostic criteria for degenerative joint disease is selected by specialist veterinarians. Each dog is initially given either PMX53 or a NSAID (e.g. deracoxib, meloxicam or tepoxalin). The administration is performed in a blinded fashion. Placebo treatment is not used because of the ethical issues of not relieving pain in dogs. The dogs receive the treatment for 28 days, followed by a "washout" period of 7-14 days, depending on return of symptoms, and then receive the second drug for 28 days. Again the administration is "blind".

Clinical response is measured by scoring the degree of lameness, clinical examination of joints to determine joint pain and range of movement, and clinical biochemistry (plasma electrolytes—$Na^+$, $K^+$, $Ca^{2+}$, liver enzymes, pancreatic enzymes, creatinine, blood urea nitrogen and glucose) and haematology (red cell count, PCV, MCV, MCHC, white cell count, differential white cell count.

Example 7

Postoperative Anti-Inflammatory Treatment

In the experiments involving the surgical severing of the cruciate ligament in dogs, described in Example 3, it was noted that dogs treated with PMX53 recovered from surgery more rapidly than placebo-treated dogs. Dogs undergoing routine orthopaedic surgery, for example for repair of ruptured cruciate ligaments, repair of luxated patella and removal of damaged menisci, are frequently given NSAIDs postoperatively to reduce inflammation and reduce pain. A blinded study with PMX53 and a NSAID such as meloxicam is performed to test whether PMX53 is effective in managing postoperative pain and in improving outcomes after surgery. This trial is performed in a specialist orthopaedic veterinary practice in order to have access to suitable dogs which are undergoing routine surgery.

Discussion

Cyclic peptides have several important advantages over acyclic peptides as drug candidates (Fairlie et al., 1995. Fairlie et al. 1998. Tyndall and Fairlie, 2001). The cyclic compounds described in this specification are stable to proteolytic degradation for at least several hours at 37° C. in human blood or plasma, in human or rat gastric juices, or in the presence of digestive enzymes such as pepsin, trypsin and chymotrypsin. In contrast, short linear peptides composed of L-amino acids are rapidly degraded to their component amino acids within a few minutes under these conditions. A second advantage lies in the constrained single conformations adopted by the cyclic and non-peptidic molecules, in contrast to acyclic or linear peptides, which are flexible enough to adopt multiple structures in solution other than the one required for receptor-binding. Thirdly, cyclic compounds such as those described in this invention are usually more lipid-soluble and more pharmacologically bioavailable as drugs than acyclic peptides, which can rarely be administered orally. Fourthly, the plasma half-lives of cyclic molecules are usually longer than those of peptides.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Fairlie, D. P., Wong, A. K.; West, M. W. Curr. Med. Chem., 1998, 5, 29-62.

Fairlie, D. P., Abbenante, G. and March, D. Curr. Med. Chem., 1995 2 672-705.

Gerard, C. and Gerard, N. P. Ann. Rev. Immunol., 1994 12 775-808.

Konteatis, Z. D., Siciliano, S. J., Van Riper, G., Molineaux, C. J., Pandya, S., Fischer, P., Rosen, H., Mumford, R. A., and Springer, M. S. J. Immunol., 1994 153 4200-4204.

Sanderson, S. D., Kirnarsky, L., Sherman, S. A., Vogen, S. M., Prakesh, O., Ember, J. A., Finch, A. M. and Taylor, S. M. J. Med. Chem., 1995 38 3669-3675.

Strachan, A J, Haaima, G, Fairlie, D P and S M Taylor. Inhibition of the reverse passive Arthus reaction and endotoxic shock in rats by a small molecule C5a receptor antagonist. *J Immunol.* 164: 6560-6565, 2000.

Tyndall, J. D. A.; Fairlie, D. P. Curr. Med. Chem. 2001, 8, 893-907.

The invention claimed is:

1. A method of treatment of osteoarthritis, comprising the step of administering an effective amount of an inhibitor of a C5a G protein-coupled receptor to a subject in need of such treatment, in which the inhibitor is a compound which
   (a) is an antagonist of a C5a G protein-coupled receptor,
   (b) has substantially no agonist activity, and
   (c) is a cyclic peptide or peptidomimetic compound of formula I:

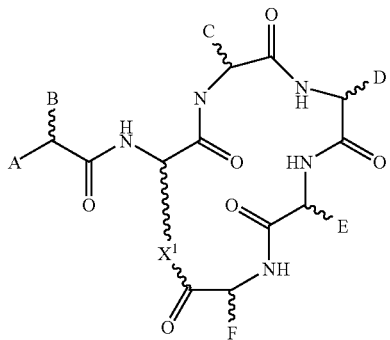

where A is H, alkyl, aryl, $NH_2$, NH-alkyl, N(alkyl)$_2$, NH-aryl, NH-acyl, NH-benzoyl, $NHSO_3$, $NHSO_2$-alkyl, $NHSO_2$-aryl, OH, O-alkyl, or O-aryl;

B is an alkyl, aryl, phenyl, benzyl, naphthyl or indole group, or B is the side chain of L-phenylalanine or L-phenylglycine;

C is the side chain of glycine, alanine, leucine, valine, proline, hydroxyproline, or thioproline;

D is the side chain of D-leucine, D-homoleucine, D-cyclohexylalanine, D-homocyclohexylalanine, D-valine, D-norleucine, D-homo-norleucine, D-phenylalanine, D-tetrahydroisoquinoline, D-glutamine, D-glutamate, or D-tyrosine;

E is the side chain of an amino acid selected from the group consisting of L-phenylalanine, L-tryptophan and L-homotryptophan, or is L-1-napthyl or L-3-benzothienyl alanine;

F is the side chain of L-arginine, L-homoarginine, L-citrulline, or L-canavanine, or a bioisostere thereof; and $X^1$ is —$(CH_2)_n$NH— or $(CH_2)_n$S—, where n is an integer of from 1 to 4; —$(CH_2)_2O$—; —$(CH_2)_3O$—; —$(CH_2)_3$—; —$(CH_2)_4$—; —$CH_2COCHRNH$—; or —$CH_2$—CHCOCHRNH—, where R is the side chain of any common or uncommon amino acid.

2. The method of claim 1, in which n is 2 or 3.

3. The method of claim 1, in which A is an acetamide group, an aminomethyl group, or a substituted or unsubstituted sulphonamide group.

4. The method of claim 2, in which A is a substituted sulphonamide, and the substituent is an alkyl chain of 1 to 6 carbon atoms, or a phenyl or toluoyl group.

5. The method of claim 3, in which the substituent is an alkyl chain of 1 to 4 carbon atoms.

6. The method of claim 1, in which the inhibitor is a compound which has antagonist activity against C5aR, and has no C5a agonist activity.

7. The method of claim 1, in which the inhibitor has potent antagonist activity at sub-micromolar concentrations.

8. The method of claim 1, in which the compound has a receptor affinity $IC_{50}$<25 μM, and an antagonist potency $IC_{50}$<1 μM.

9. The method of claim 1, in which the compound is selected from the group consisting of: compounds 1 to 6, 10 to 15, 17, 19, 20, 22, 25, 26, 28, 30, 31, 33 to 37, 39 to 45, 56 to 58 and 60 to 64, wherein said compounds have chemical structures as follows:

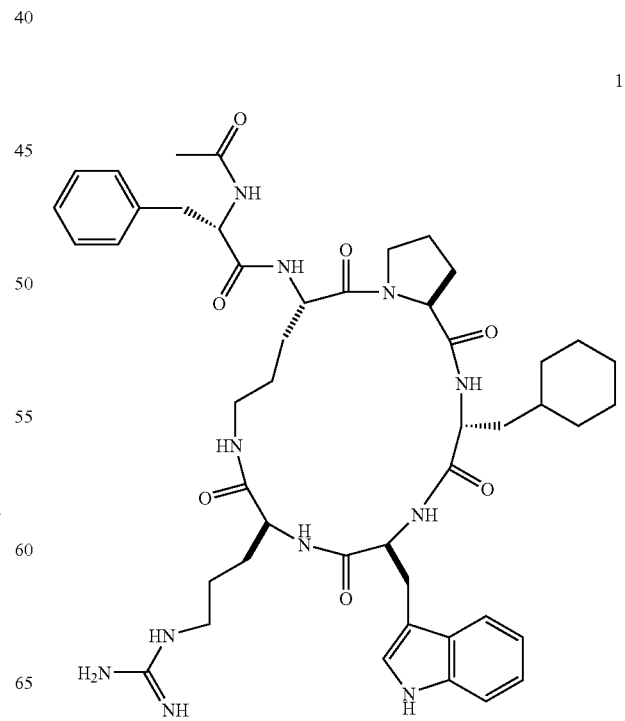

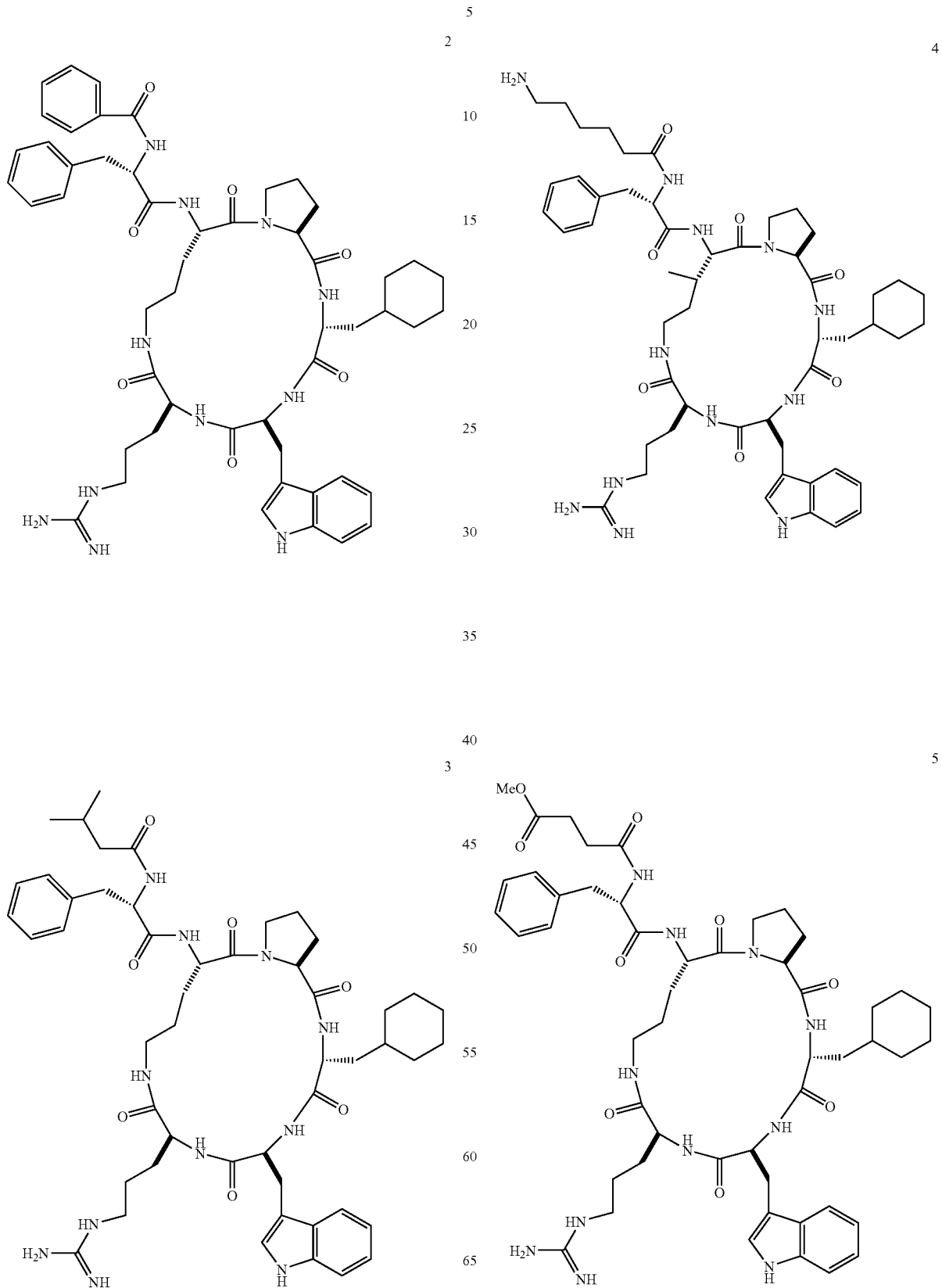

5
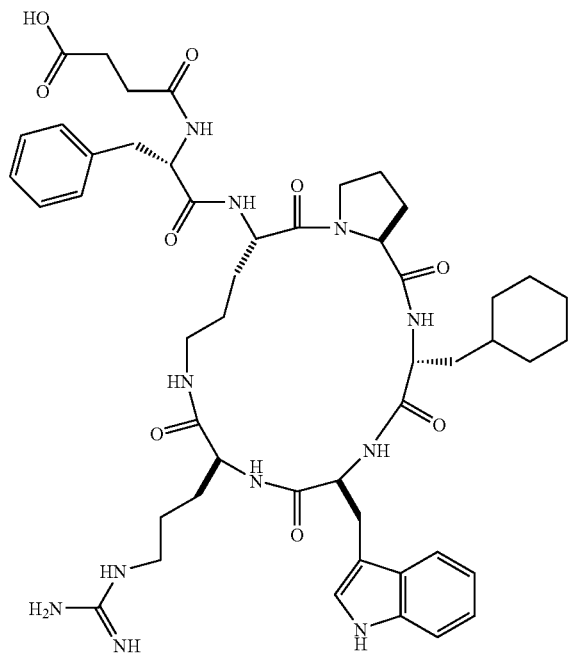
6
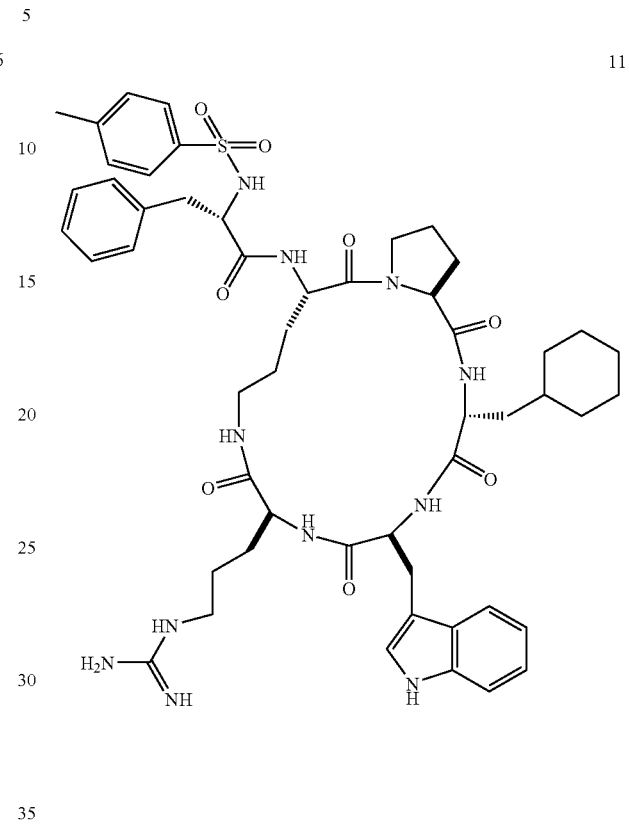
10
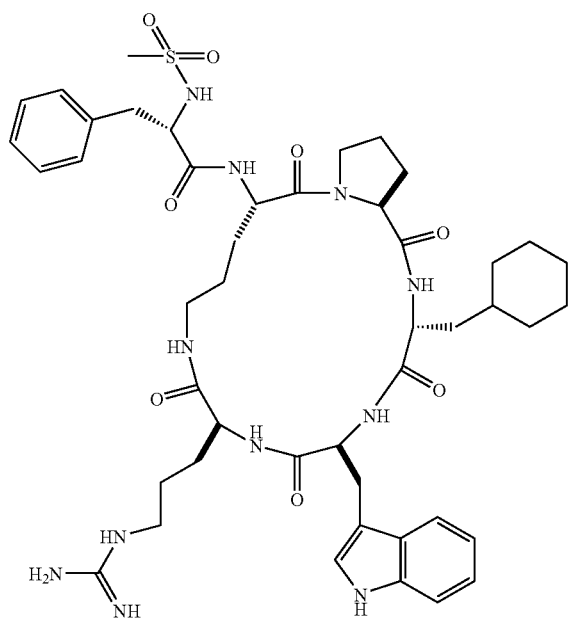
11
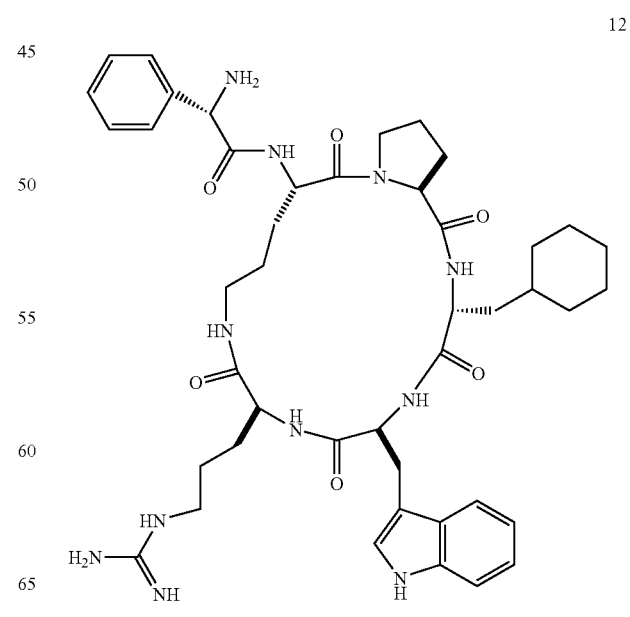
12

13
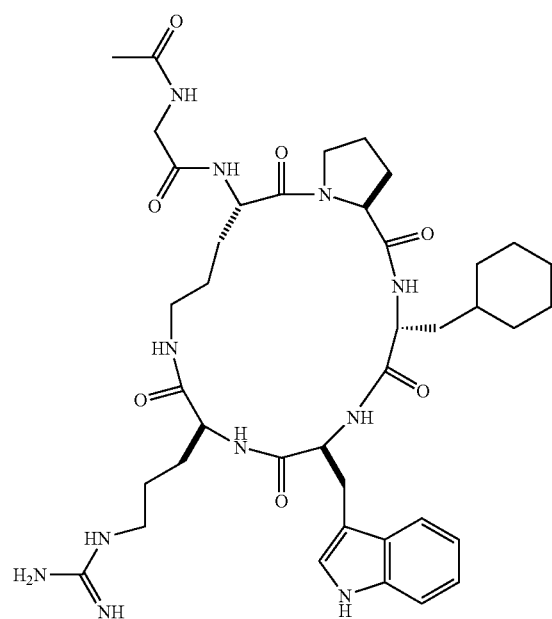
15
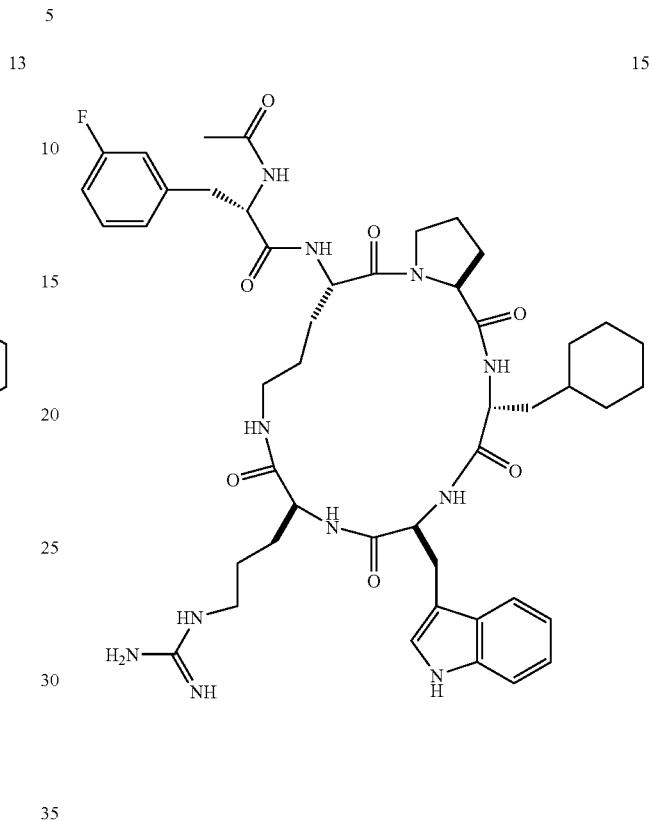
14
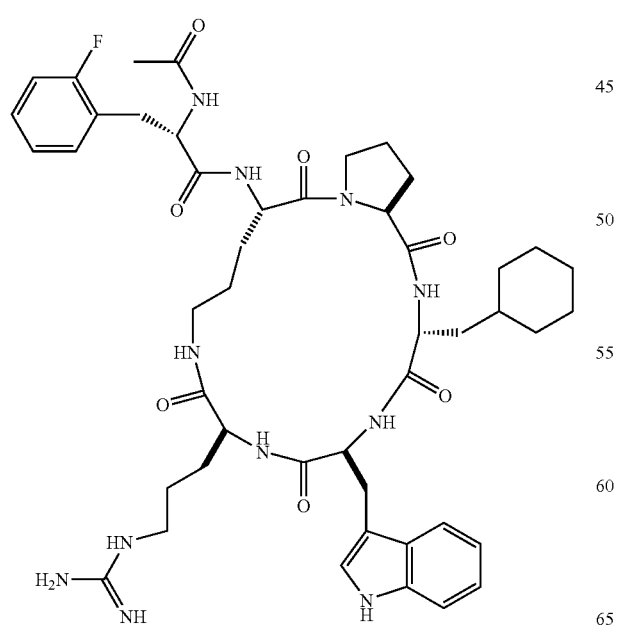
17
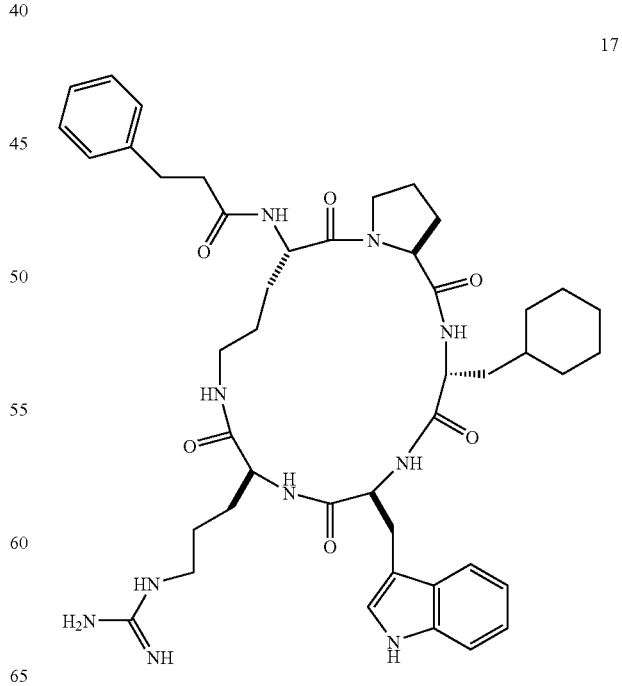

19
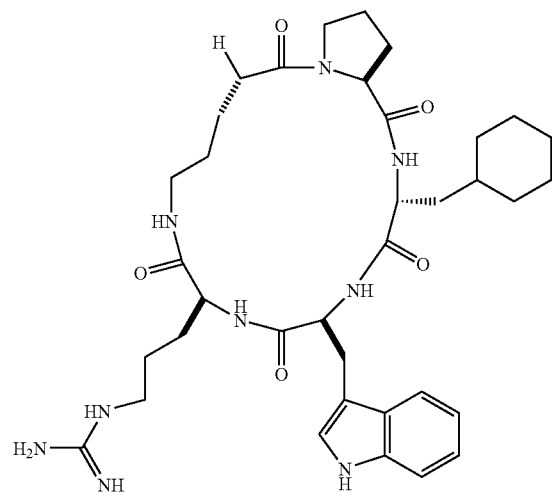
22
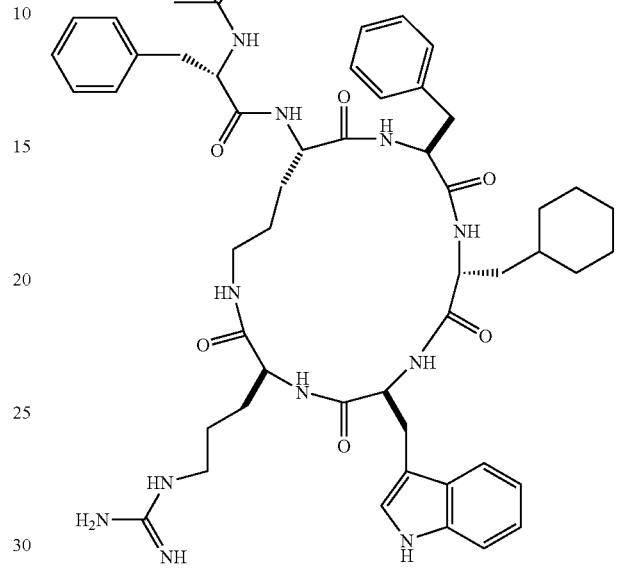
20
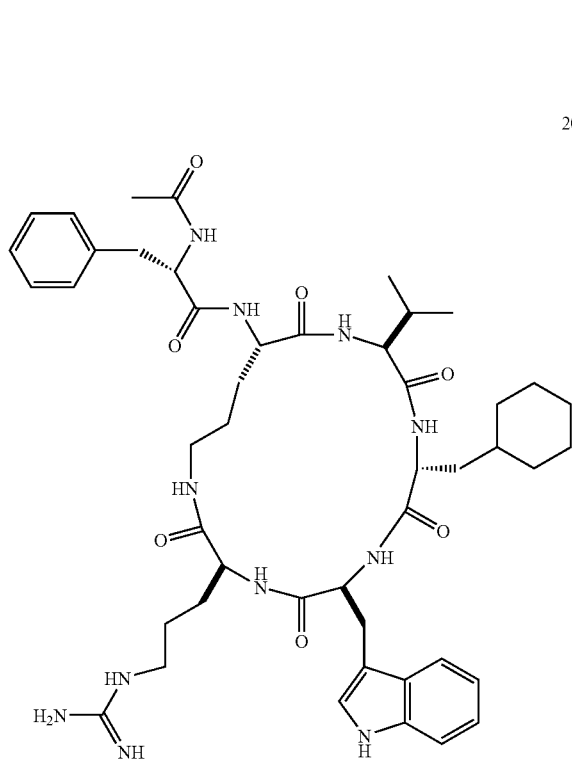
25
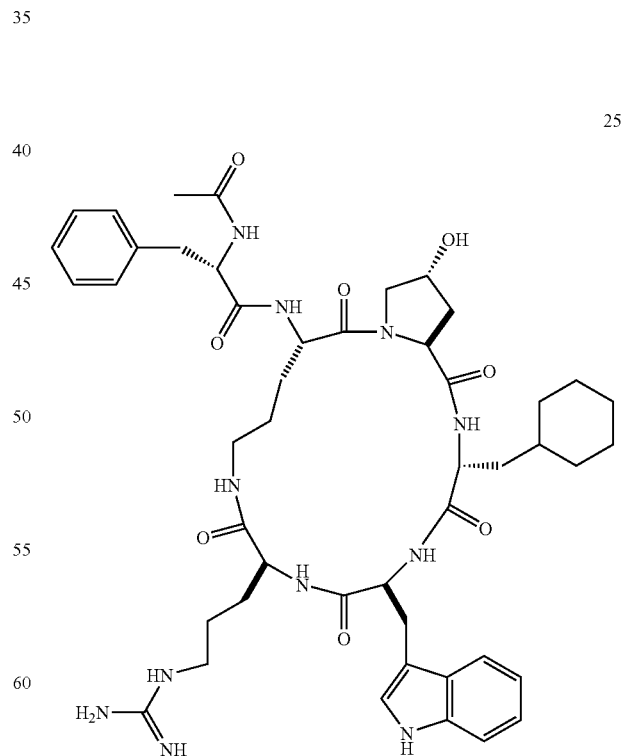

26
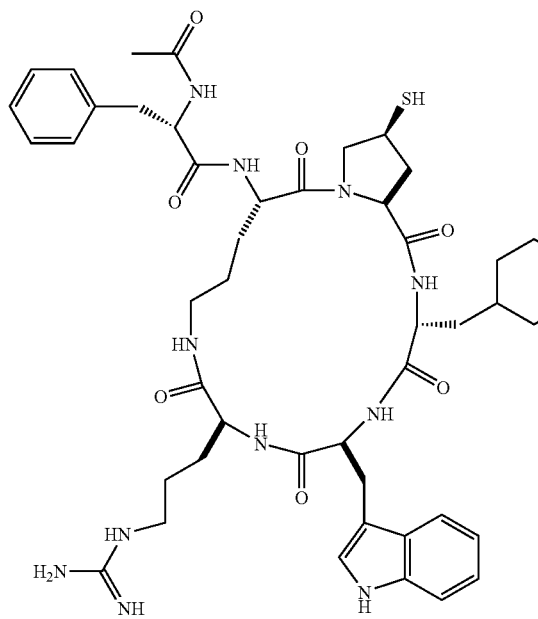
30
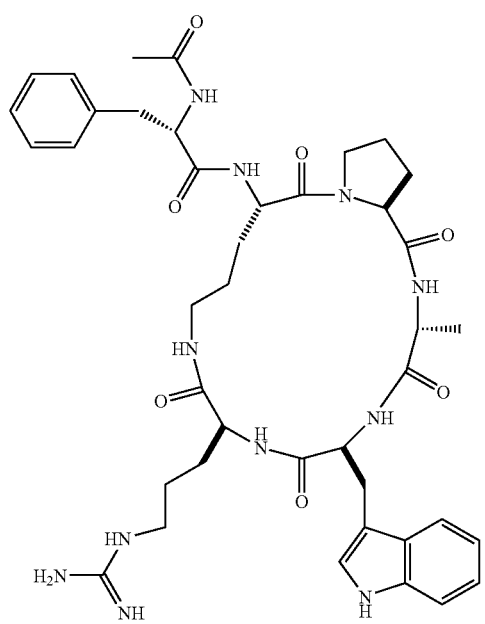
28
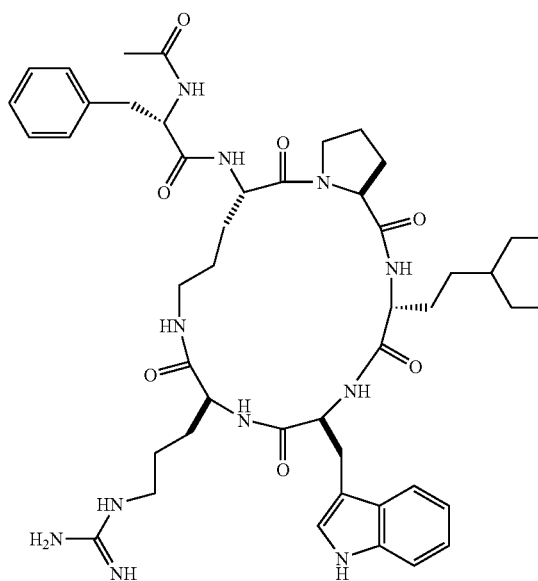
31
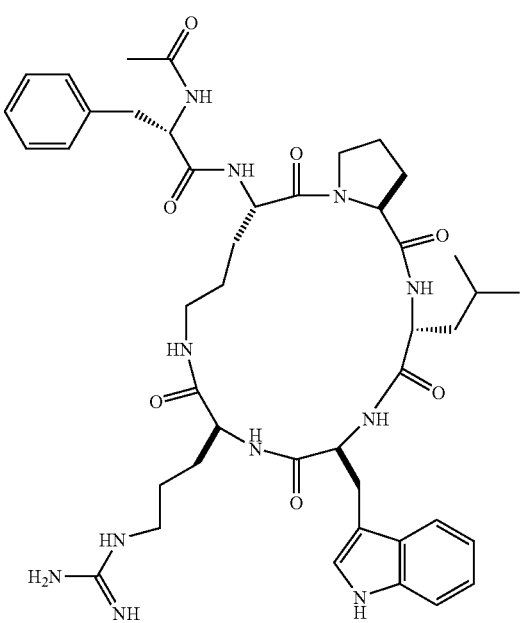

-continued
33
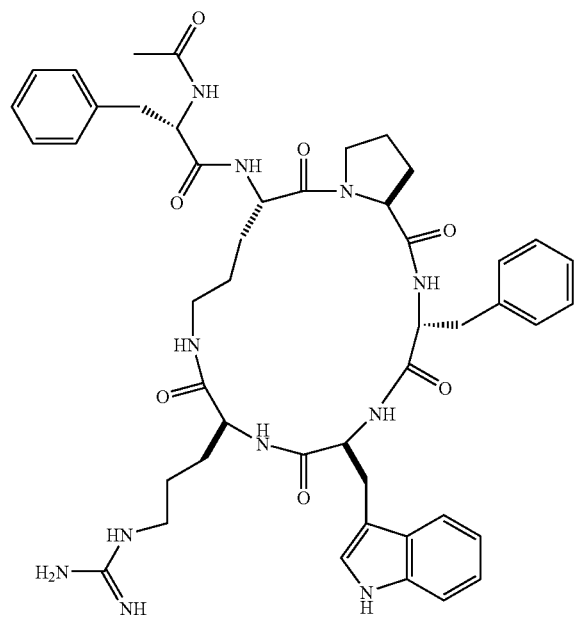
34
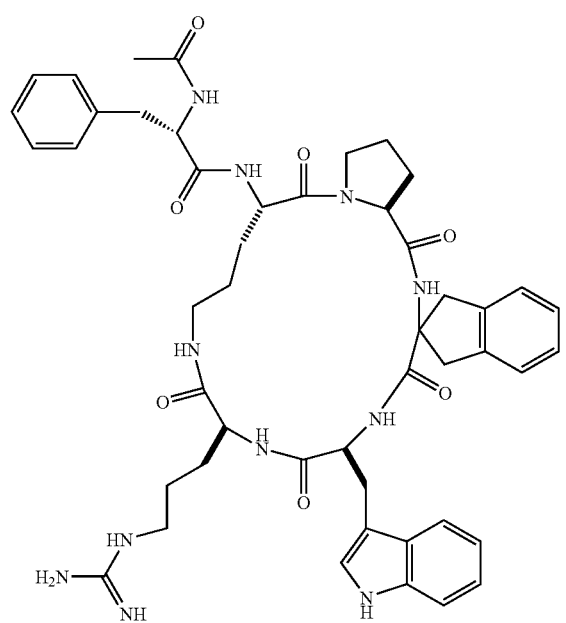
-continued
35
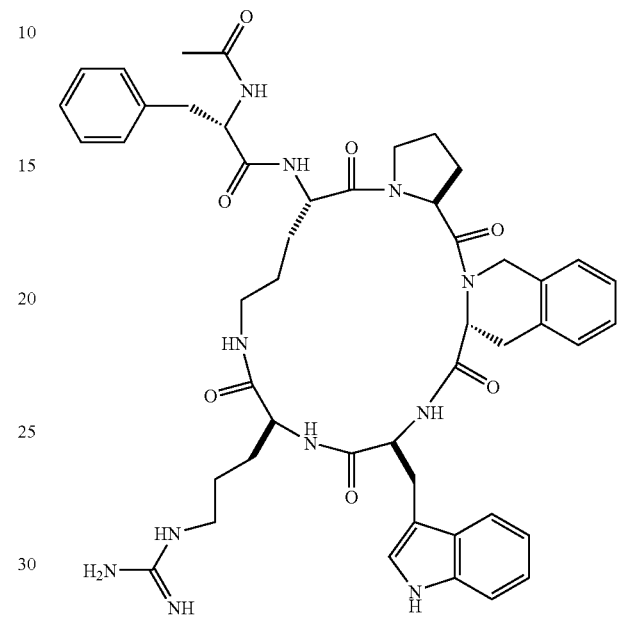
36
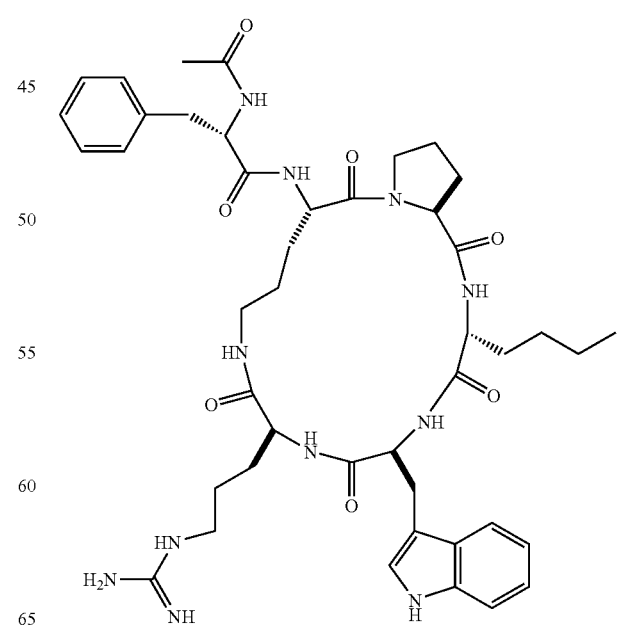

37
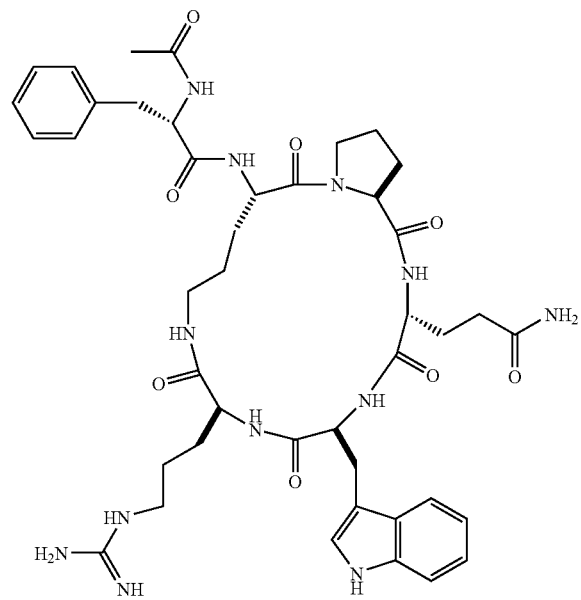
40
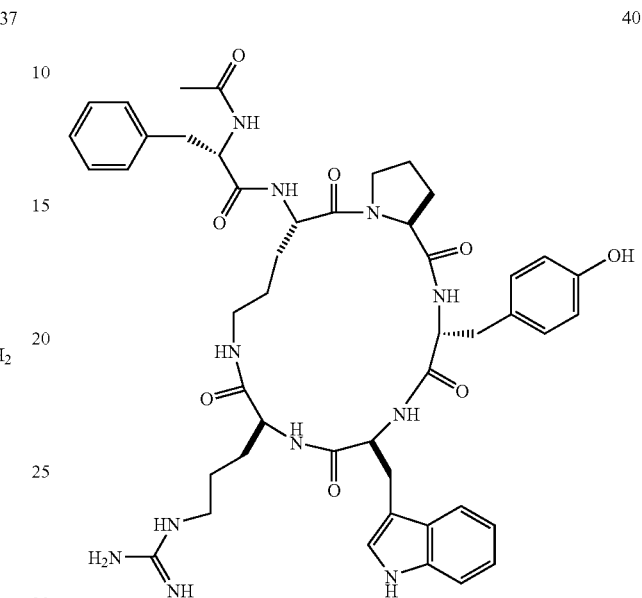
39
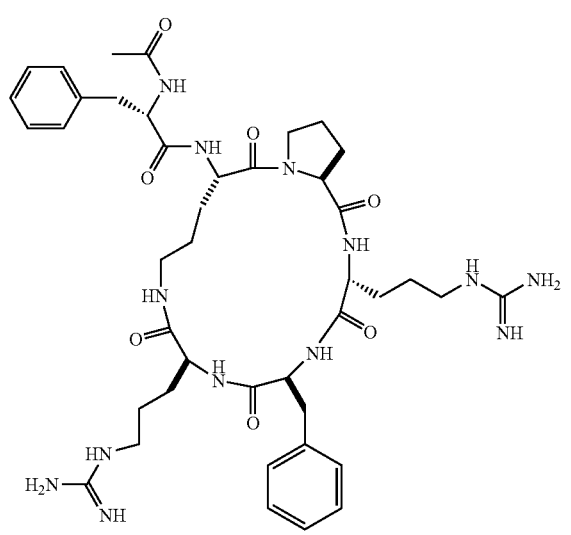
41
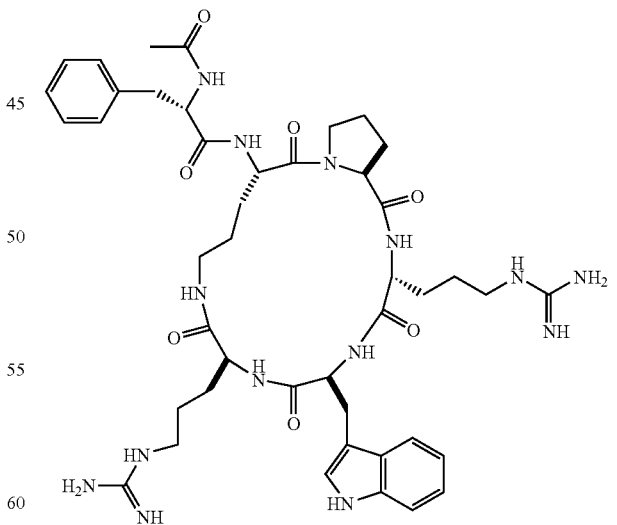

42
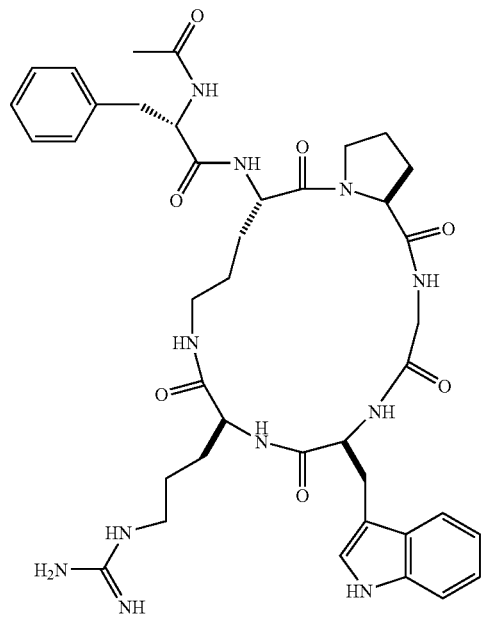
44
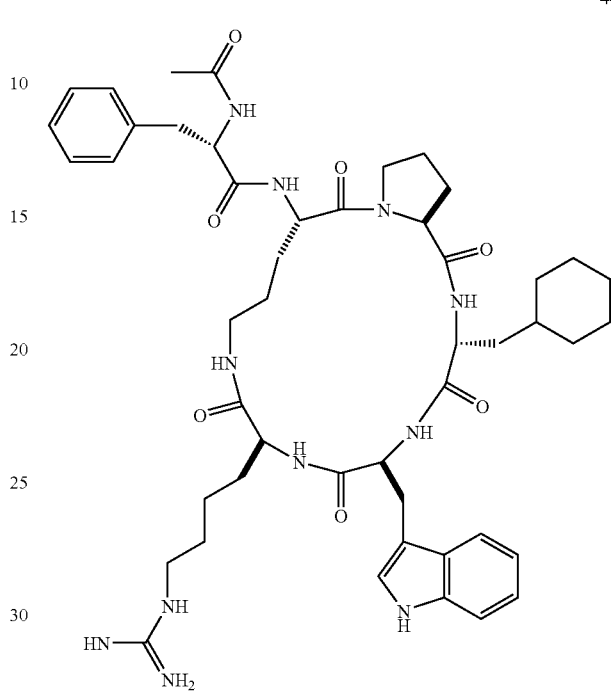
43
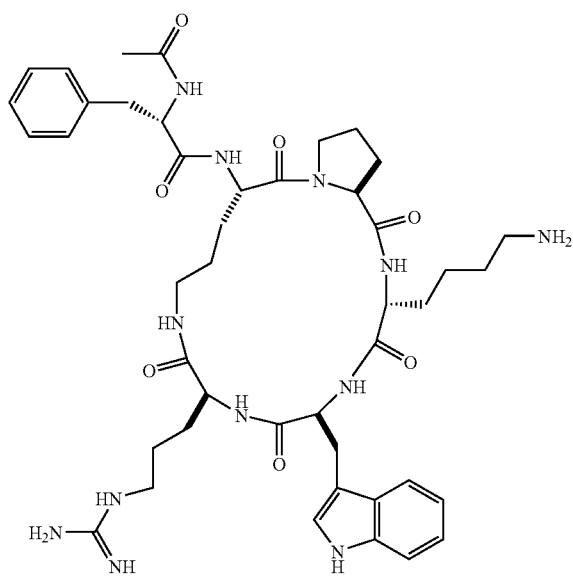
45
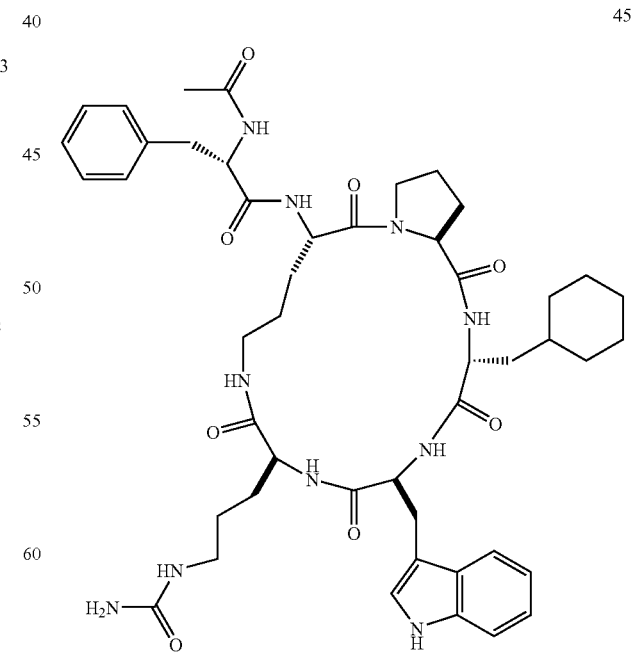

56
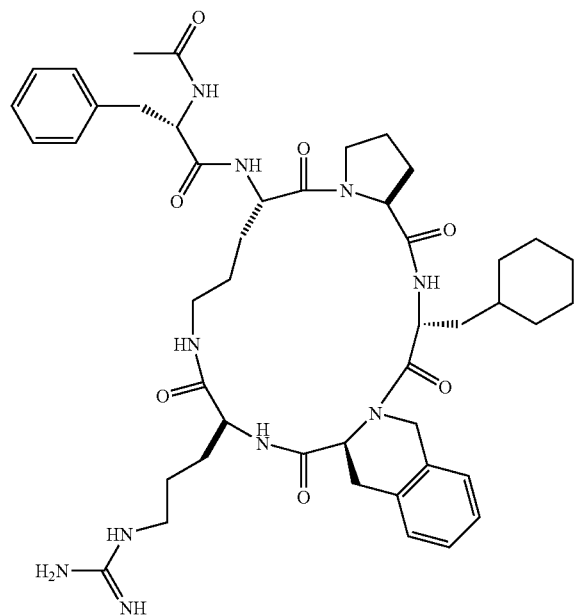
58
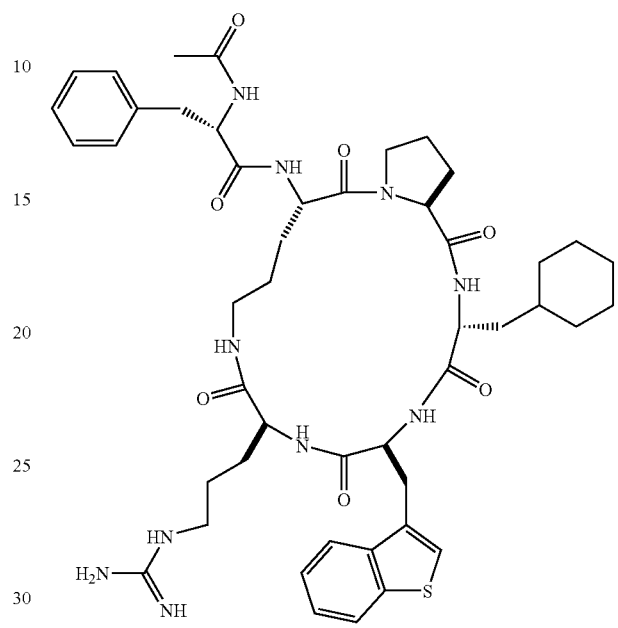
57
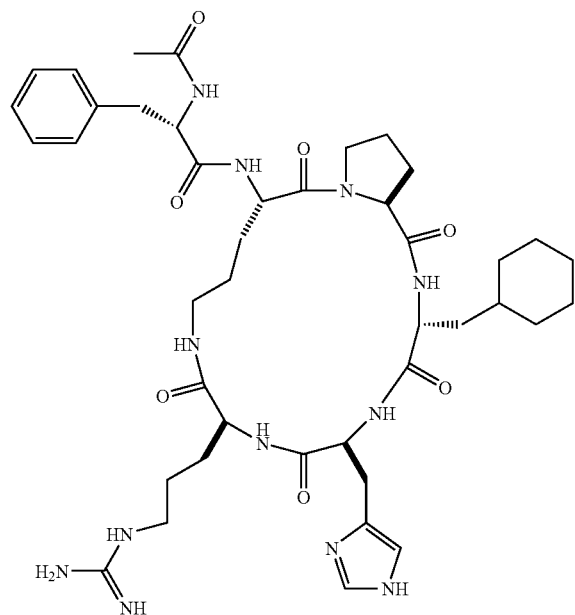
60
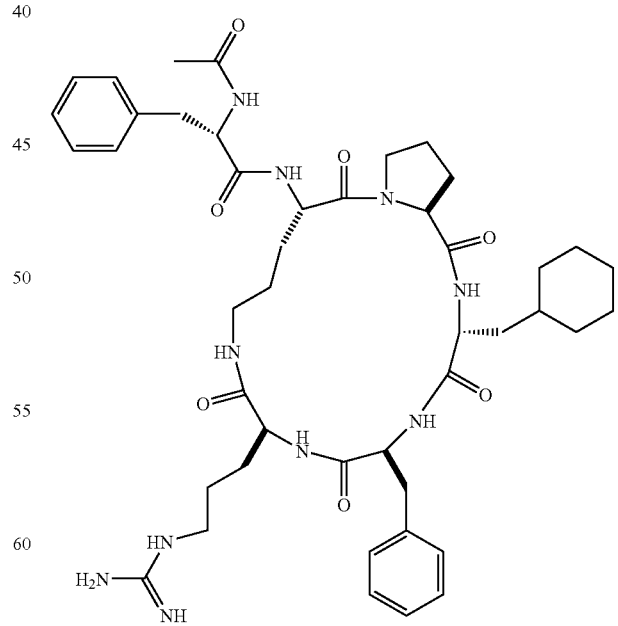

61
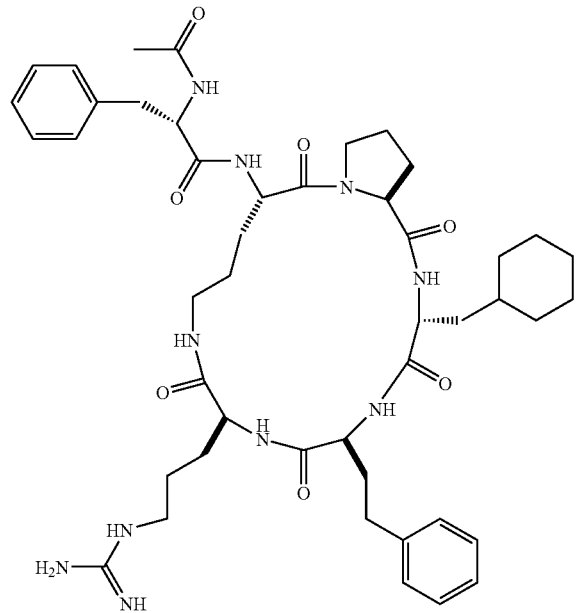
62
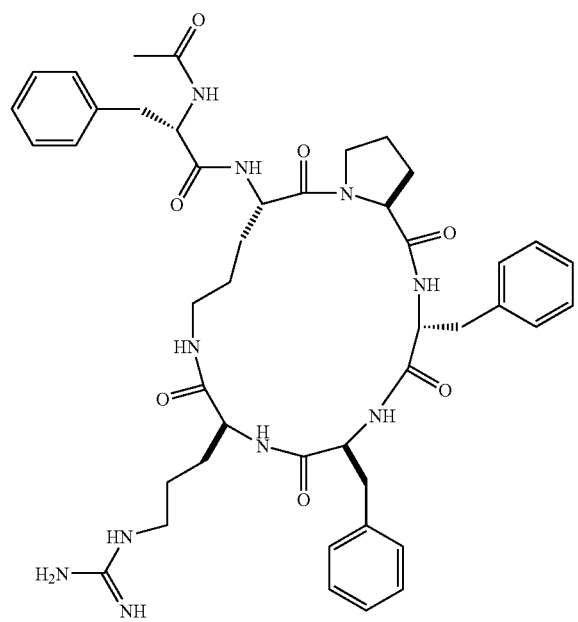
63
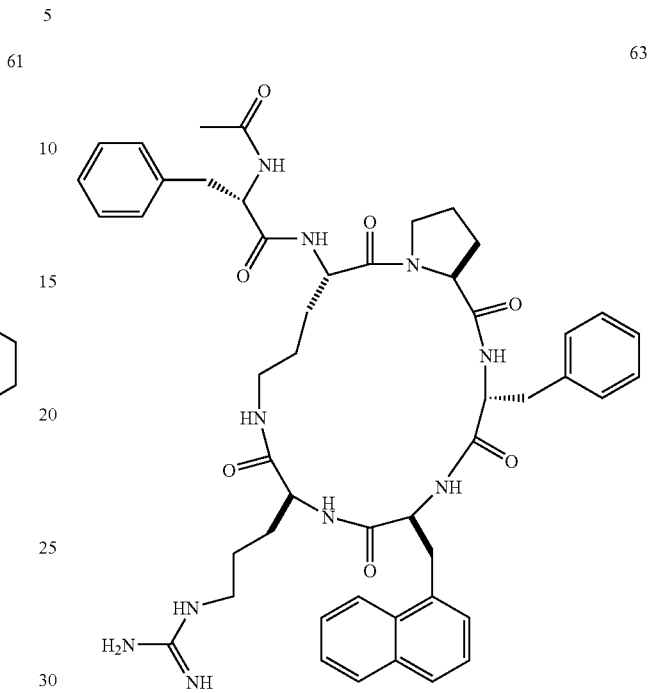
64
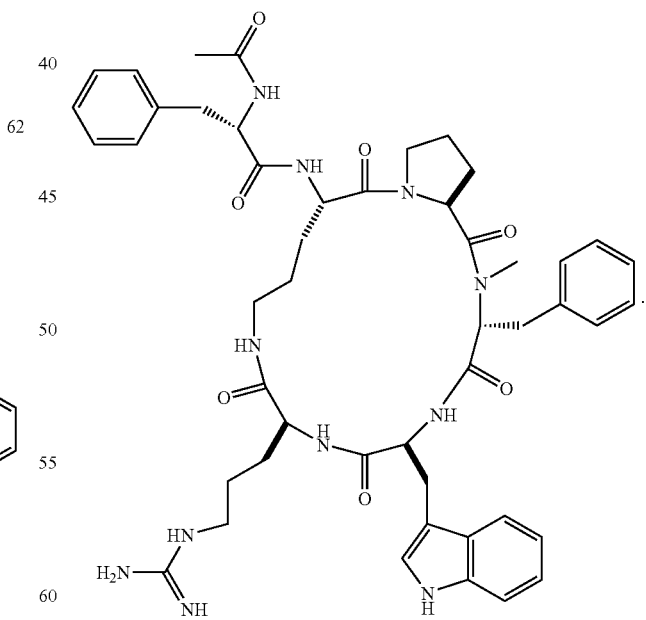
10. The method of claim 9, in which the compound is compound 1 (AcF-[OP-DCha-WR]), compound 33 (AcF-[OP-DPhe-WR]), compound 60 (AcF-[OP-DCha-FR]) or compound 45 (AcF-[OP-DCha-WCit]), wherein said compounds have chemical structures as follows:

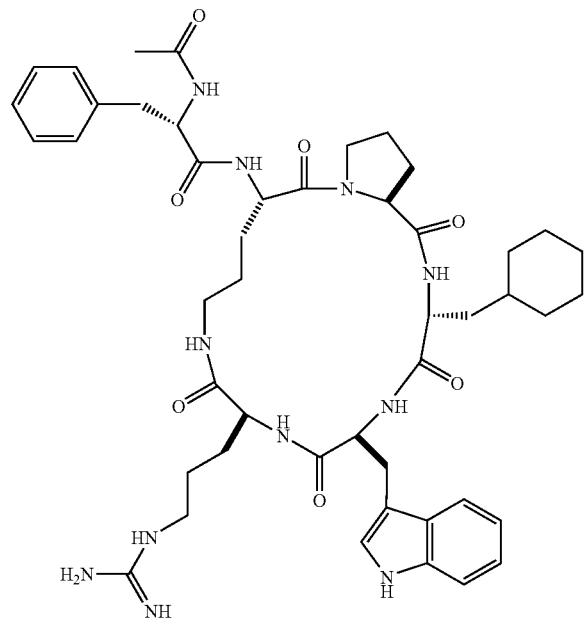

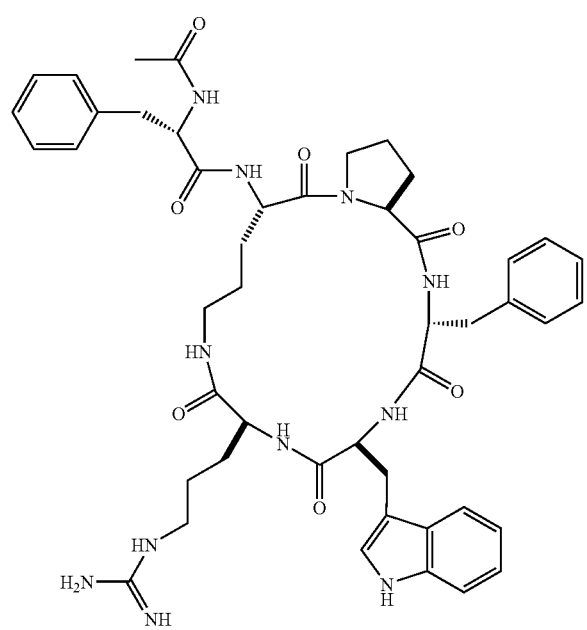

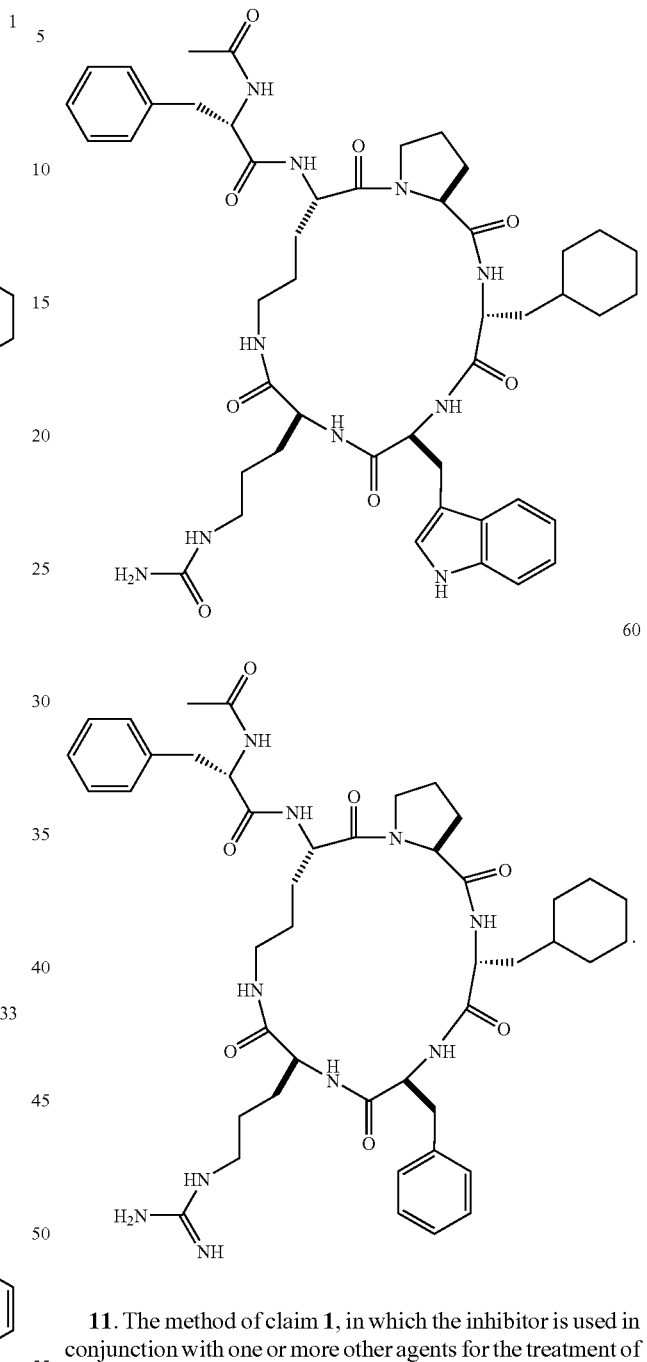

11. The method of claim 1, in which the inhibitor is used in conjunction with one or more other agents for the treatment of osteoarthritis.

12. The method of claim 1, wherein A is NH-acyl; B is the side chain of L-phenylalanine; C is the side chain of L-proline; D is the side chain of D-cyclohexylalanine; E is the side chain of L-tryptophan; F is the side chain of L-arginine; and $X^1$ is —$(CH_2)_n$NH—, where n is 3.

13. A method for treating osteoarthritis in a mammal, said method comprising the step of: administering to a mammal in need thereof, an effective amount of a composition comprising a C5a G protein-coupled receptor antagonist compound that (a) has substantially no agonist activity and (b) is a cyclic peptide or peptidomimetic compound of formula I:

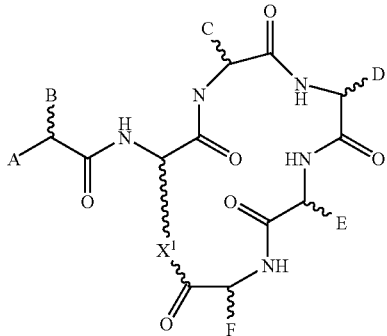

(I)

wherein:
A is H, alkyl, aryl, NH$_2$, NH-alkyl, N(alkyl)$_2$, NH-aryl, NH-acyl, NH-benzoyl, NHSO$_3$, NHSO$_2$-alkyl, NHSO$_2$-aryl, OH, O-alkyl, or O-aryl;
B is an alkyl, aryl, phenyl, benzyl, naphthyl or indole group, or B is the side chain of L-phenylalanine or L-phenylglycine;
C is the side chain of glycine, alanine, leucine, valine, proline, hydroxyproline, or thioproline;
D is the side chain of D-leucine, D-homoleucine, D-cyclohexylalanine, D-homocyclohexylalanine, D-valine, D-norleucine, D-homo-norleucine, D-phenylalanine, D-tetrahydroisoquinoline, D-glutamine, D-glutamate, or D-tyrosine;
E is the side chain of an amino acid selected from the group consisting of L-phenylalanine, L-tryptophan and L-homotryptophan, or is L-1-napthyl or L-3-benzothienyl alanine;
F is the side chain of L-arginine, L-homoarginine, L-citrulline, or L-canavanine, or a bioisostere thereof; and
X$^1$ is —(CH$_2$)$_n$NH— or (CH$_2$)$_n$S—, where n is an integer of from 1 to 4; —(CH$_2$)$_2$O—; —(CH$_2$)$_3$O—; —(CH$_2$)$_3$—; —(CH$_2$)$_4$—; —CH$_2$COCHRNH—; or —CH$_2$—CHCOCHRNH—, where R is the side chain of any common or uncommon amino acid.

14. The method of claim 13, wherein
A is H, alkyl, aryl, NH$_2$, NH-alkyl, N(alkyl)$_2$, NH-aryl, NH-acyl, NH-benzoyl, NHSO$_3$, NHSO$_2$-alkyl, NHSO$_2$-aryl, OH, O-alkyl, or O-aryl;
B is an alkyl, aryl, phenyl, benzyl, naphthyl or indole group, or B is the side chain of L-phenylalanine or L-phenylglycine;
C is the side chain of glycine, alanine, leucine, valine, proline, hydroxyproline, or thioproline;
D is the side chain of D-leucine, D-homoleucine, D-cyclohexylalanine, D-homocyclohexylalanine, D-valine, D-norleucine, D-homo-norleucine, D-phenylalanine, D-tetrahydroisoquinoline, D-glutamine, D-glutamate, or D-tyrosine;
E is the side chain of an amino acid selected from the group consisting of L-phenylalanine, L-tryptophan and L-homotryptophan, or is L-1-napthyl or L-3-benzothienyl alanine;
F is the side chain of L-arginine, L-homoarginine, L-citrulline, or L-canavanine; and
X$^1$ is —(CH$_2$)$_n$NH— or (CH$_2$)$_n$S—, where n is an integer from 1 to 4.

15. The method of claim 14, wherein A is NH-acyl; B is the side chain of L-phenylalanine; C is the side chain of L-proline; D is the side chain of D-cyclohexylalanine; E is the side chain of L-tryptophan; F is the side chain of L-arginine; and X$^1$ is —(CH$_2$)$_n$NH—, where n is 3.

16. A method of treatment of osteoarthritis, said method comprising the step of administering to a subject in need thereof, an effective amount of a pharmaceutically-acceptable composition that comprises a C5a G protein-coupled receptor inhibitor, wherein said inhibitor:
(a) is an antagonist of a C5a G protein-coupled receptor;
(b) has substantially no agonist activity; and
(c) is a cyclic peptide or peptidomimetic compound of formula I:

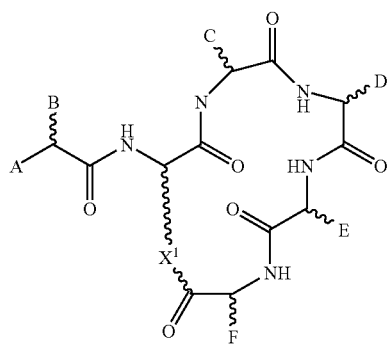

(I)

wherein A is NH-acyl; B is the side chain of L-phenylalanine; C is the side chain of L-proline; D is the side chain of D-cyclohexylalanine; E is the side chain of L-tryptophan; F is the side chain of L-arginine; and X$^1$ is —(CH$_2$)$_n$NH—, where n is 3.

17. A method of treating osteoarthritis in a subject, said method comprising the step of administering to said subject an effective amount of a cyclic peptide or peptidomimetic compound selected from the group consisting of:

1

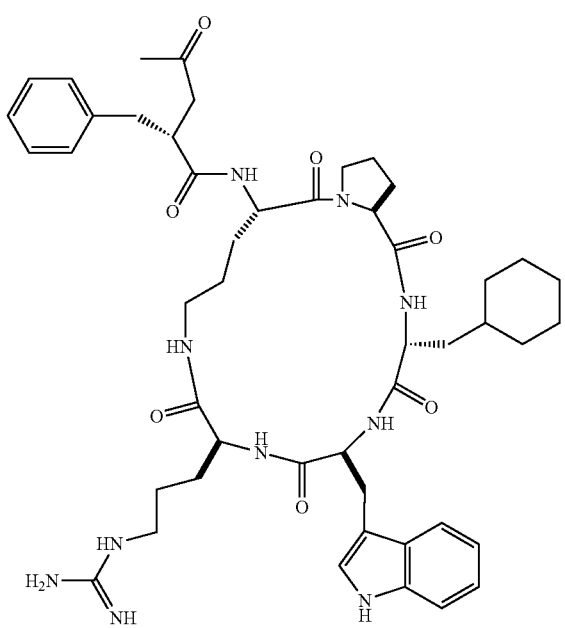

-continued
2
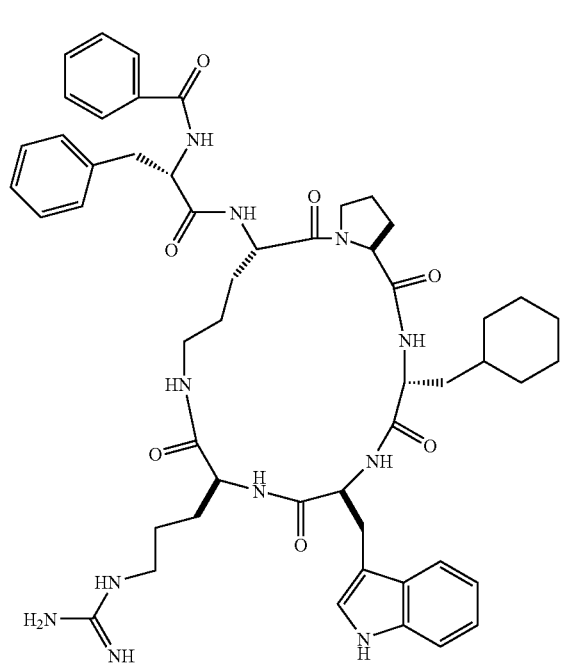
3
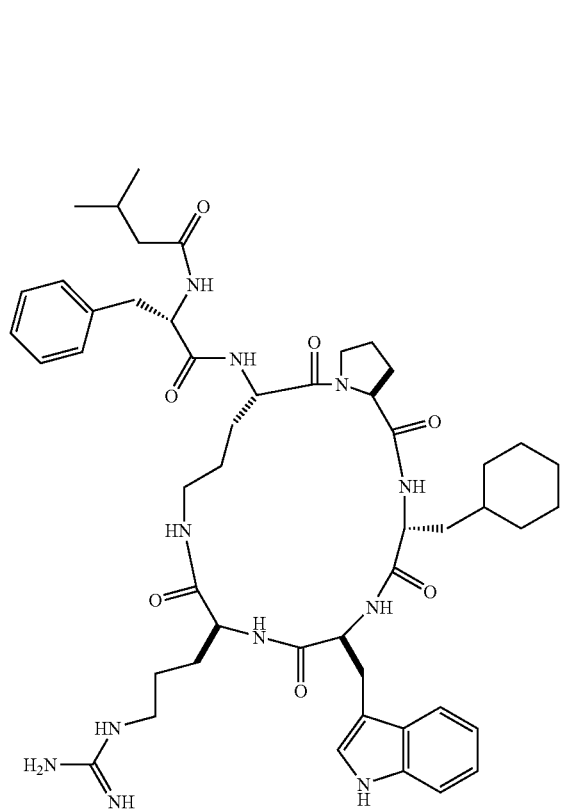
-continued
4
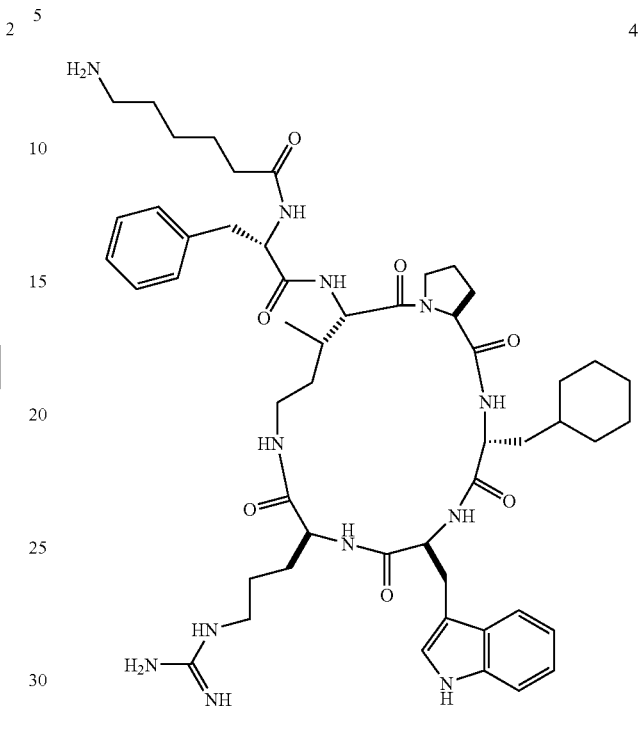
5
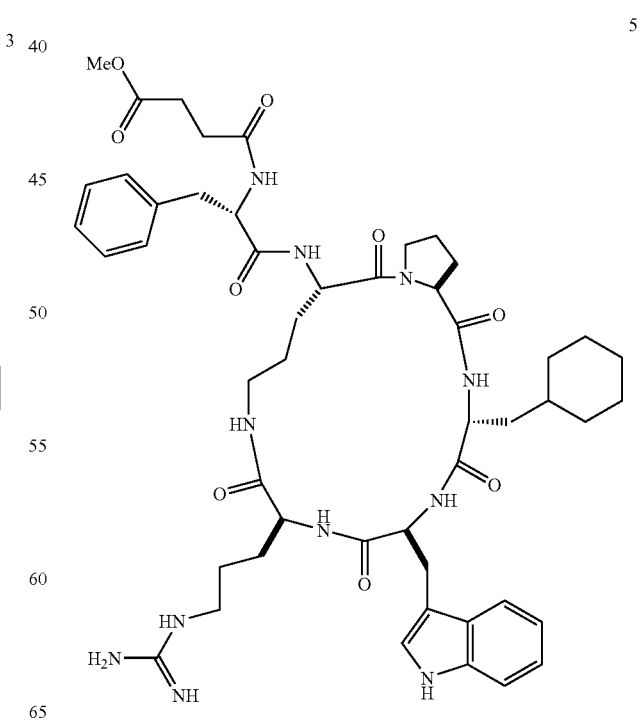

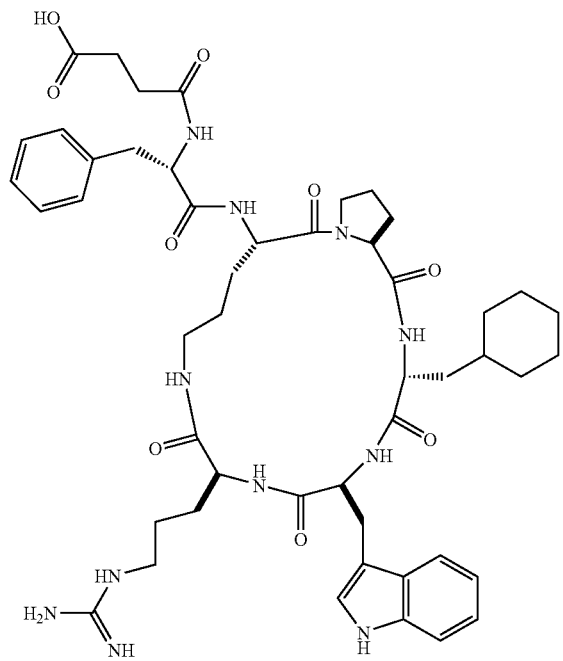
5
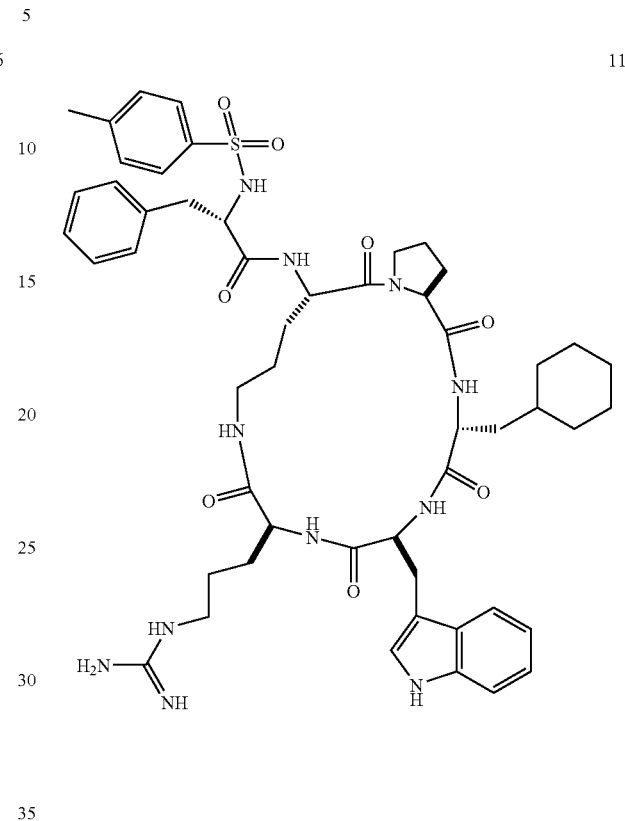
6
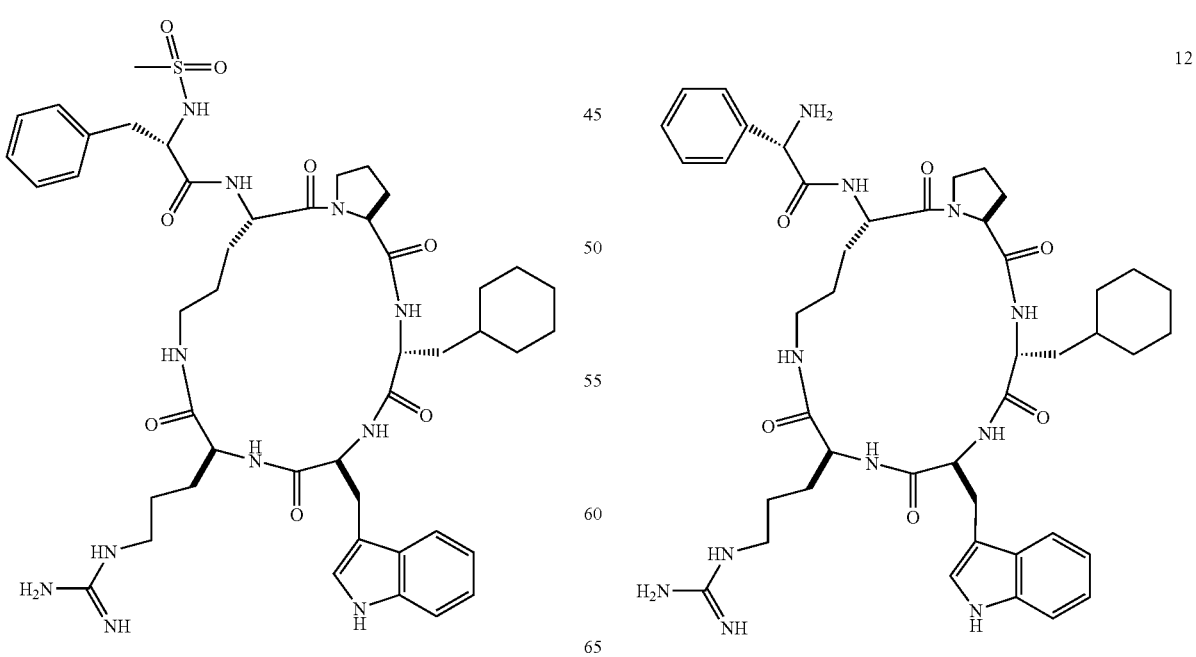
11
12

5
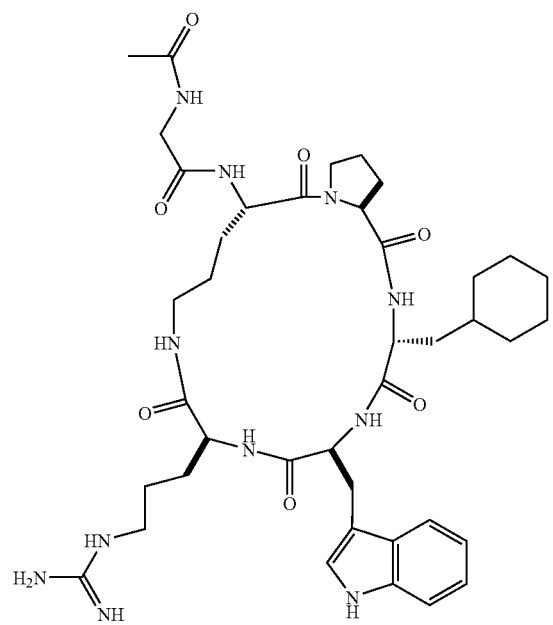
13
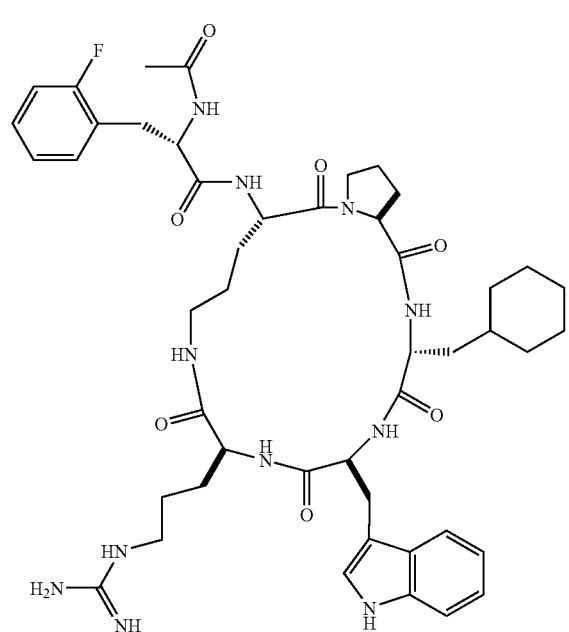
70
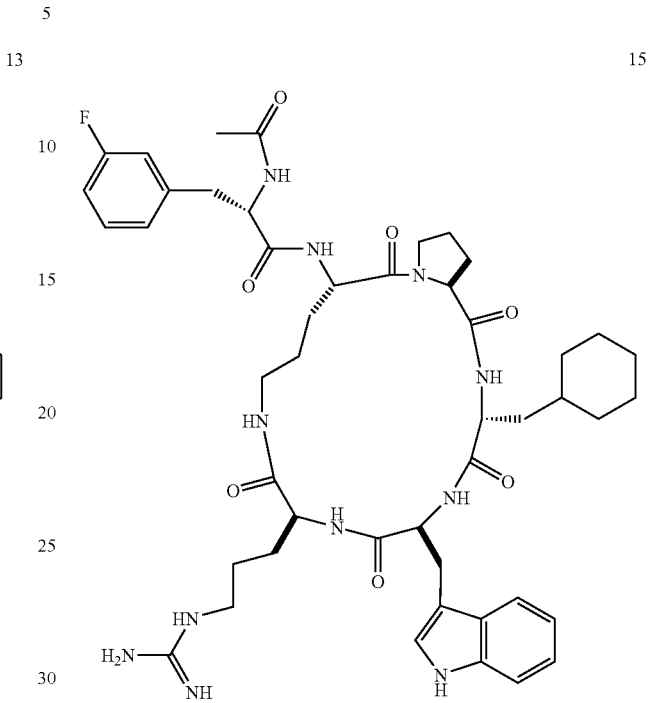
17
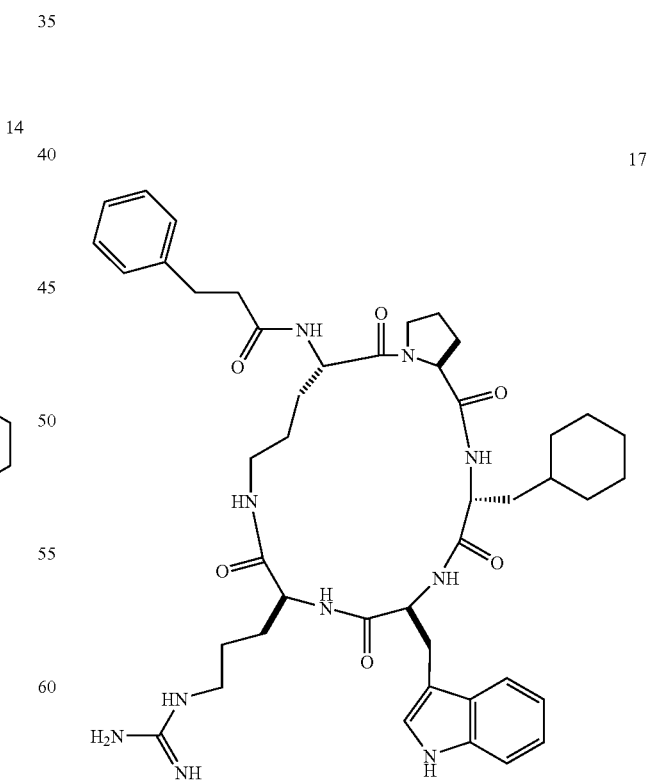

19
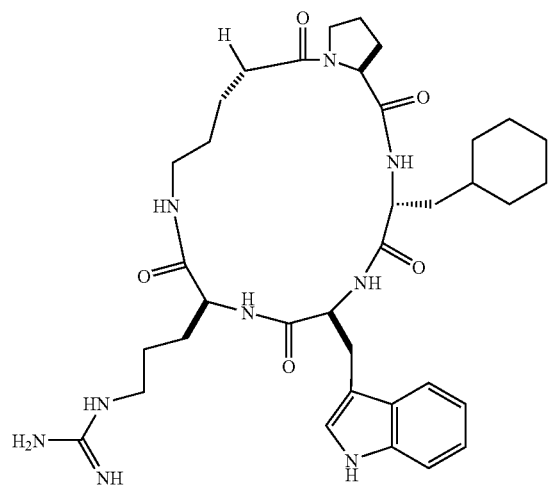
20
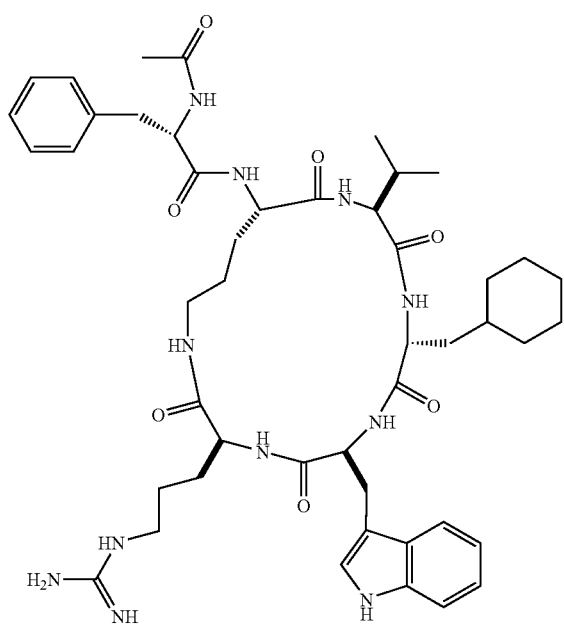
22
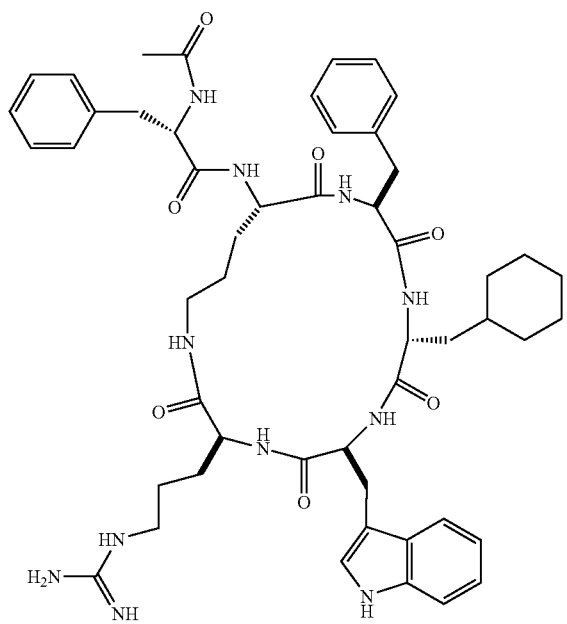
25
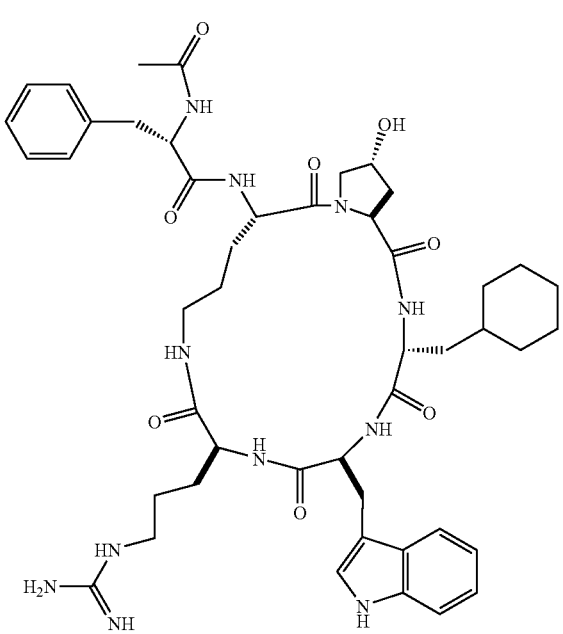

73
-continued
26
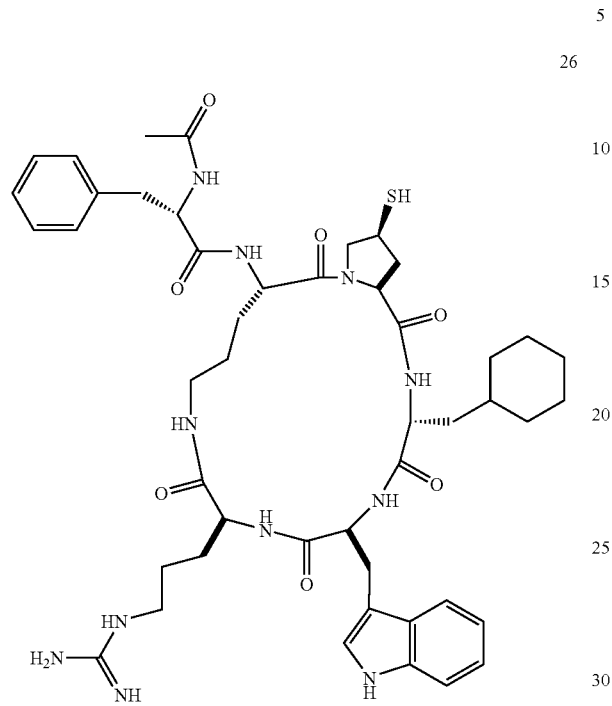
5
74
-continued
30
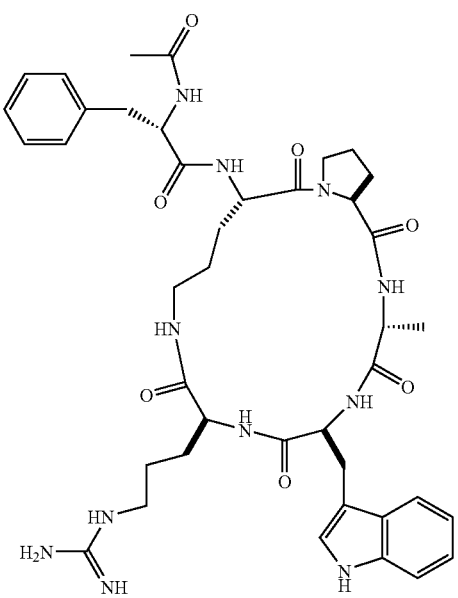
28
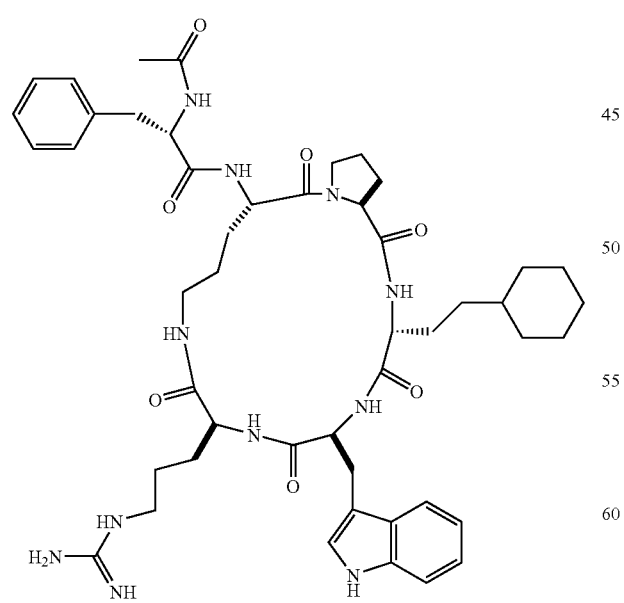
31
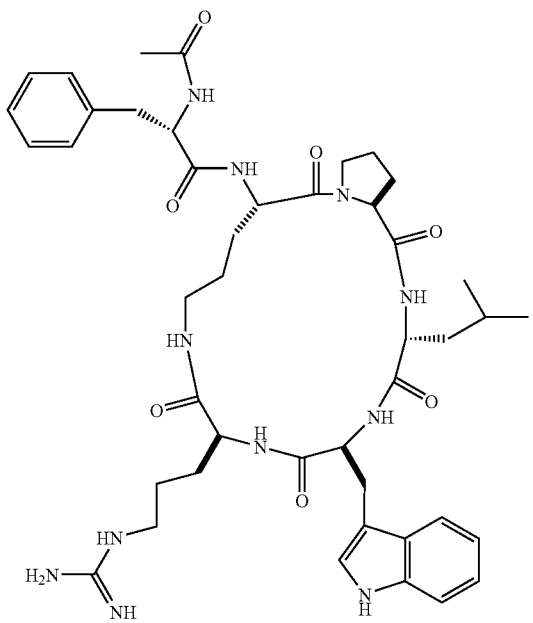

33
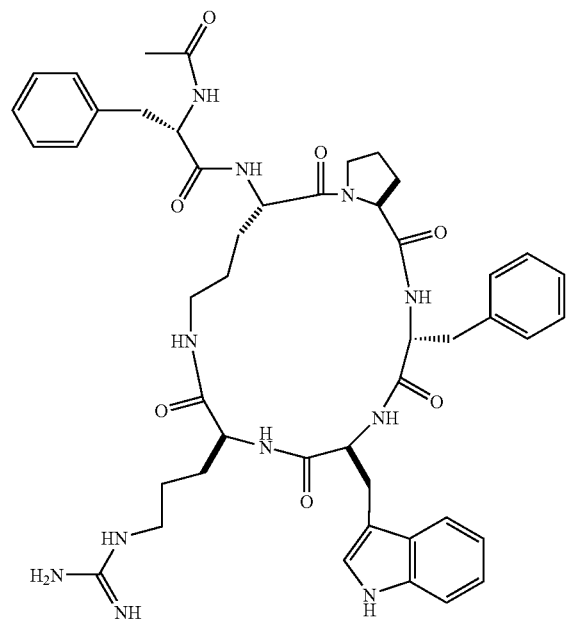
35
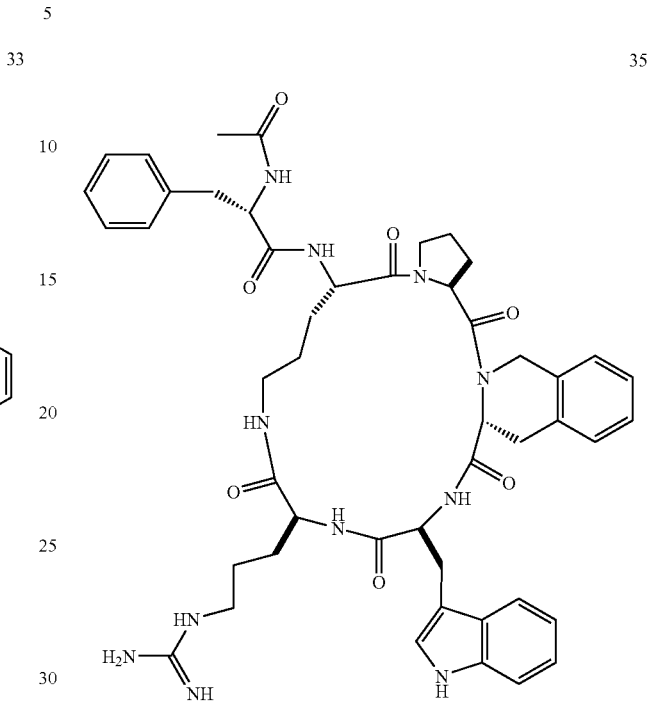
34
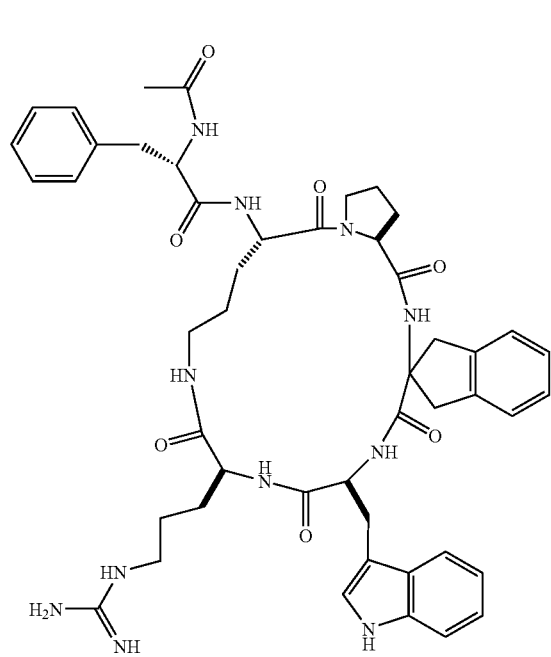
36
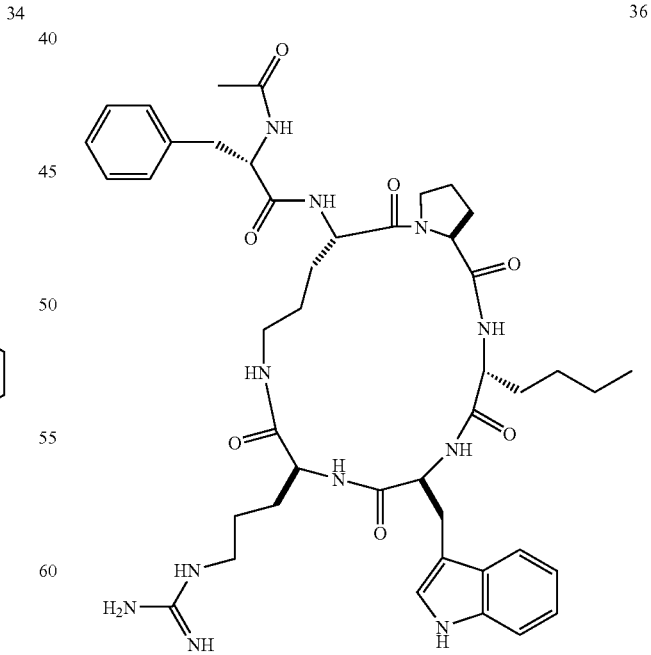

37
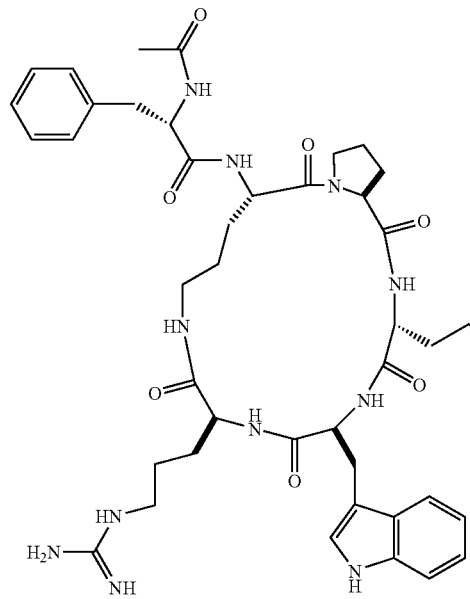
40
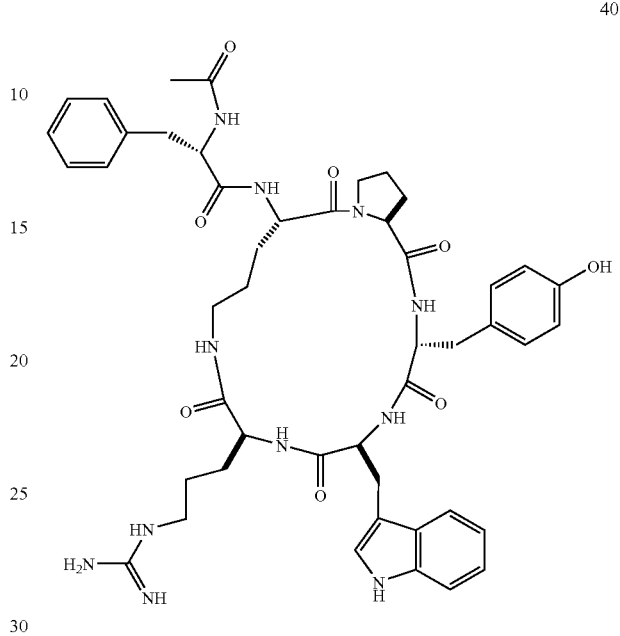
39
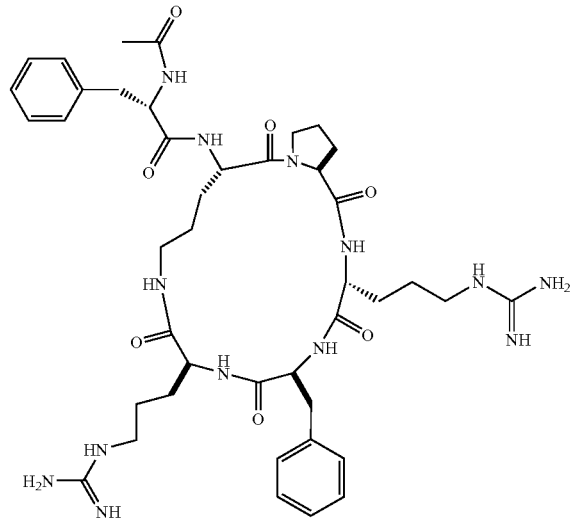
41
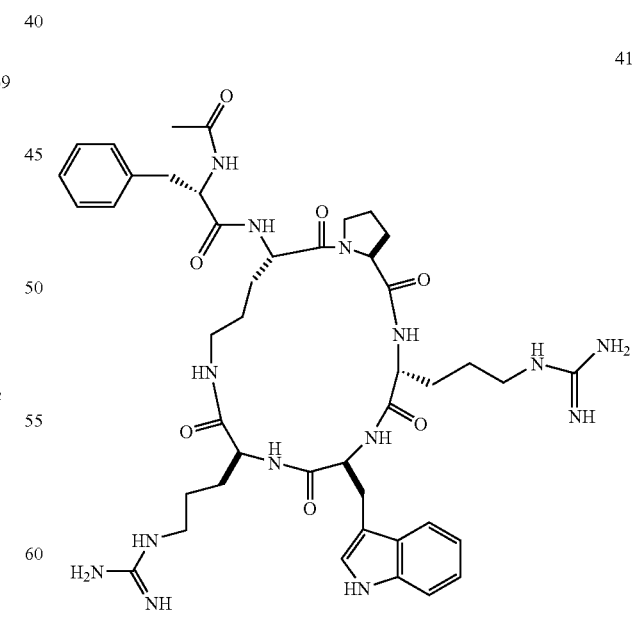

42
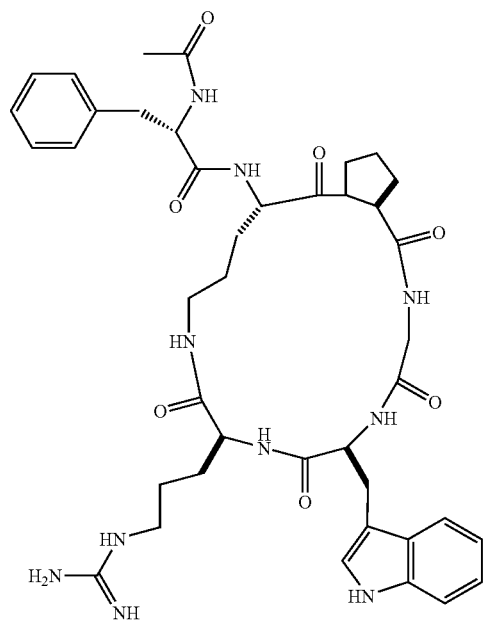
44
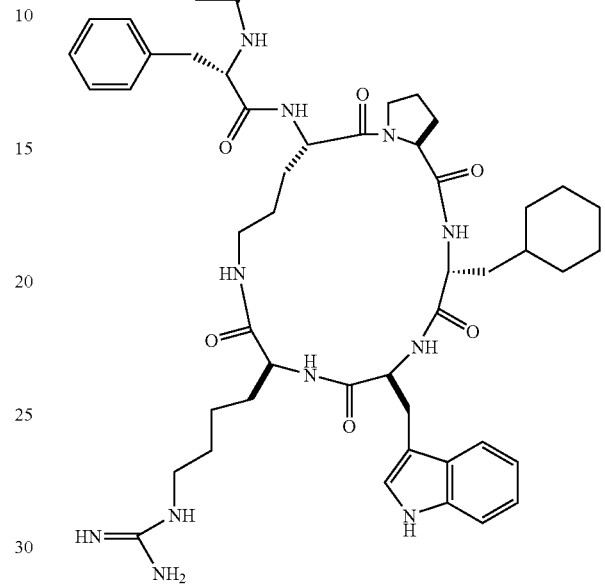
43
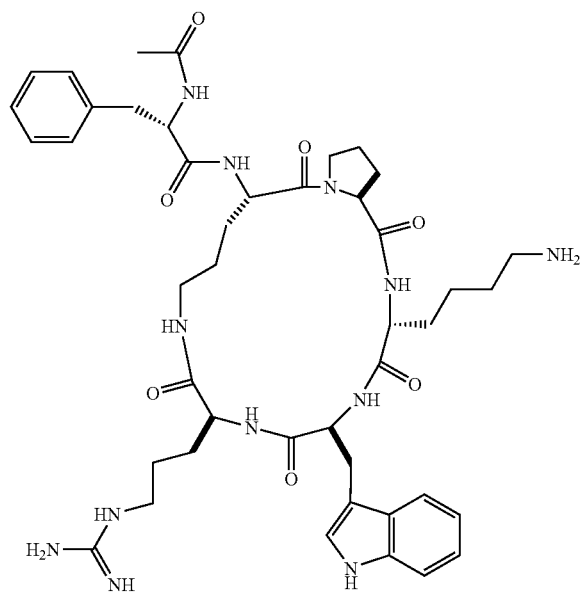
45
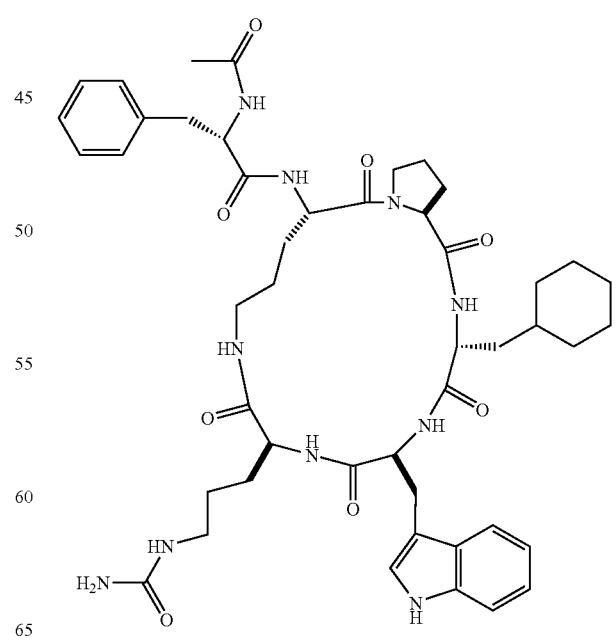

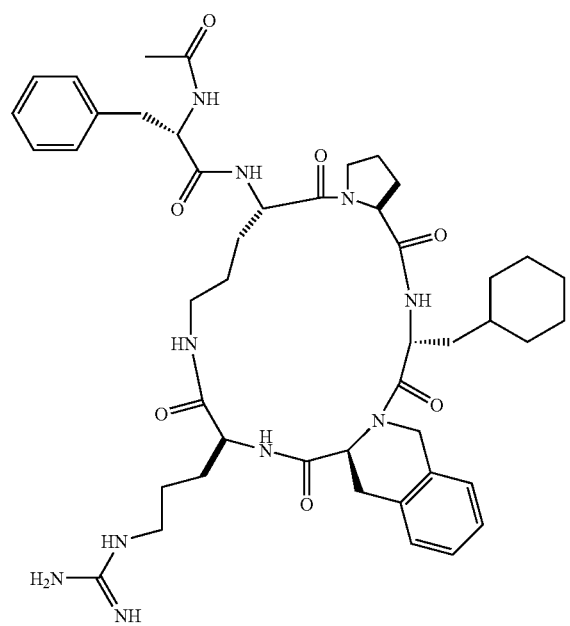
56
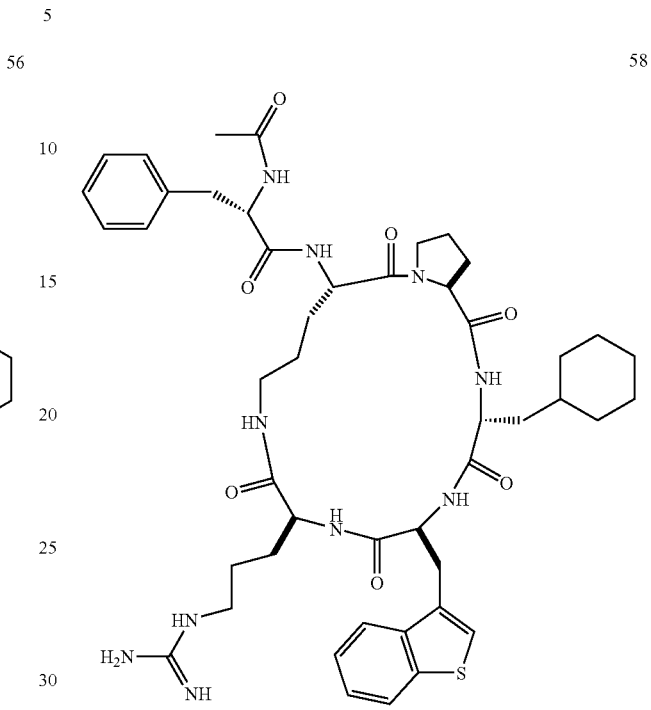
58
57
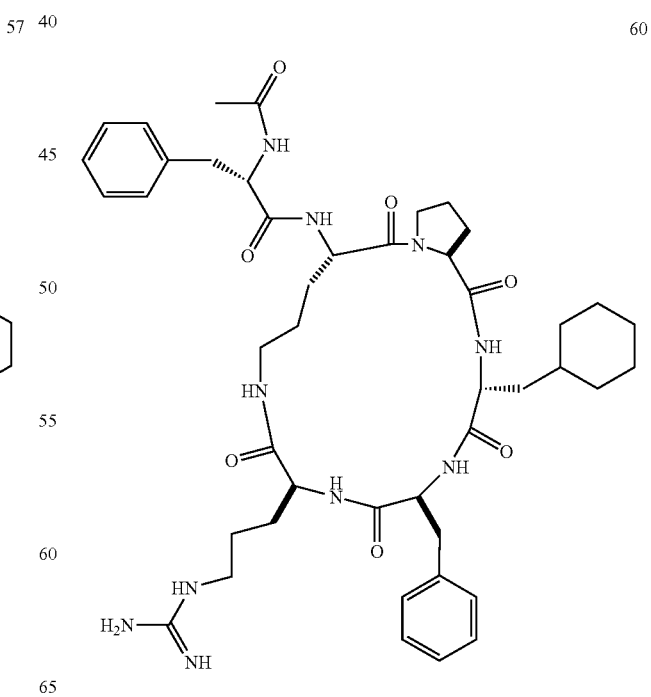
60

61
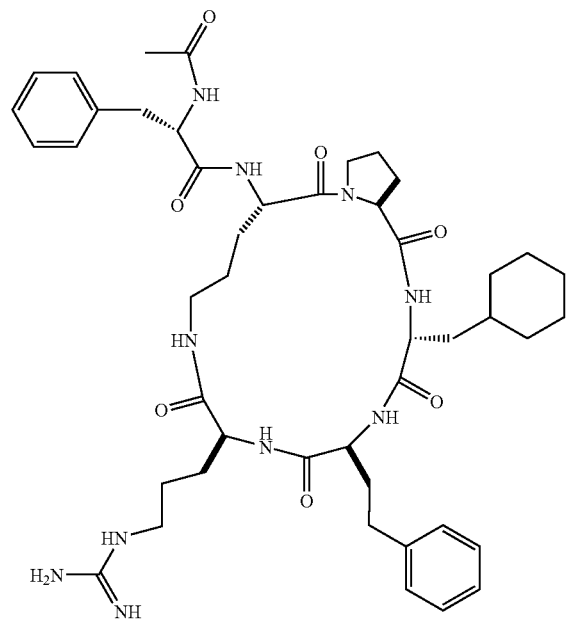
63
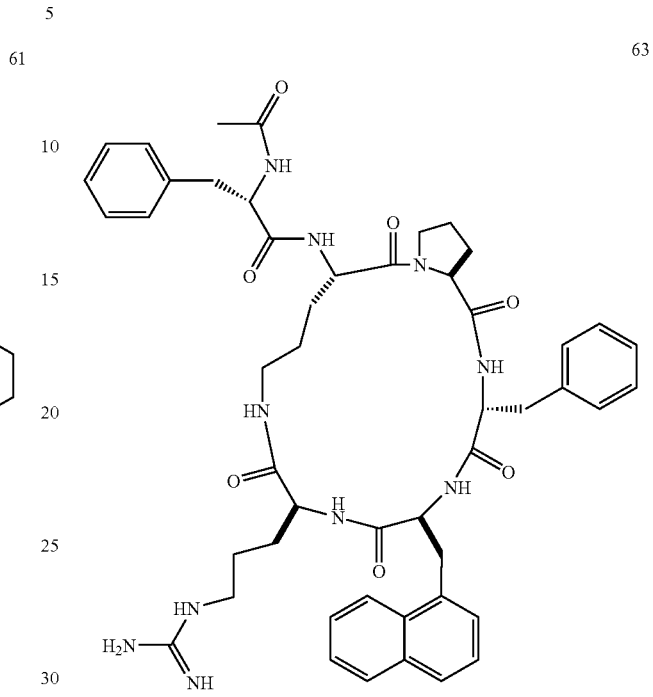
62
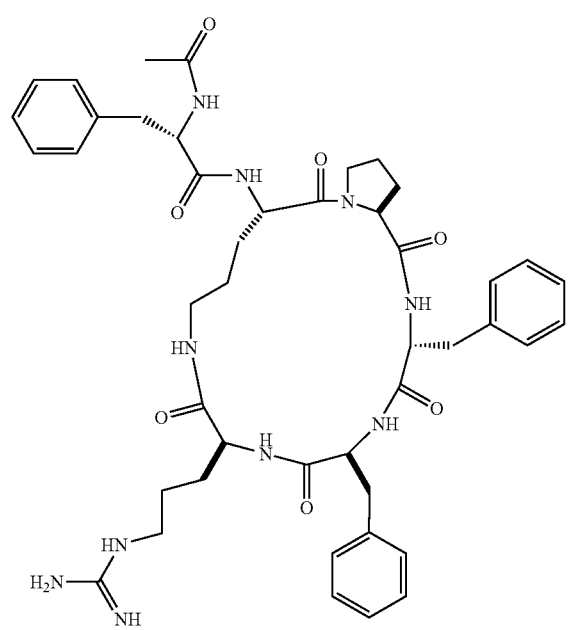
64
wherein said compound is a C5a G protein-coupled receptor antagonist that has substantially no agonist activity.
18. The method of claim 17, wherein said compound is selected from the group consisting of:

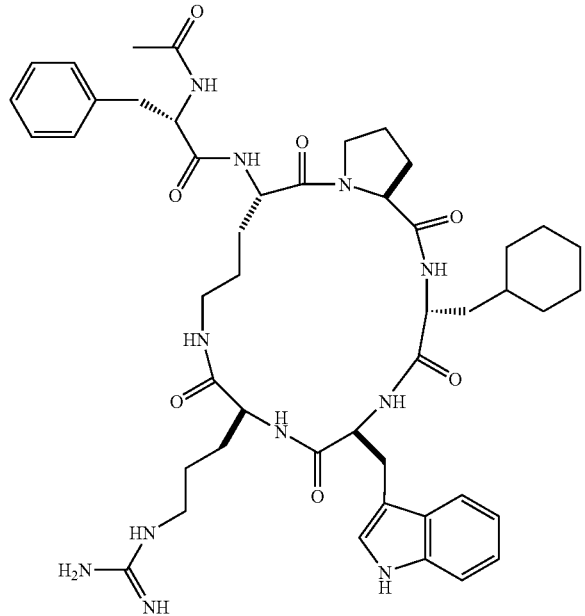
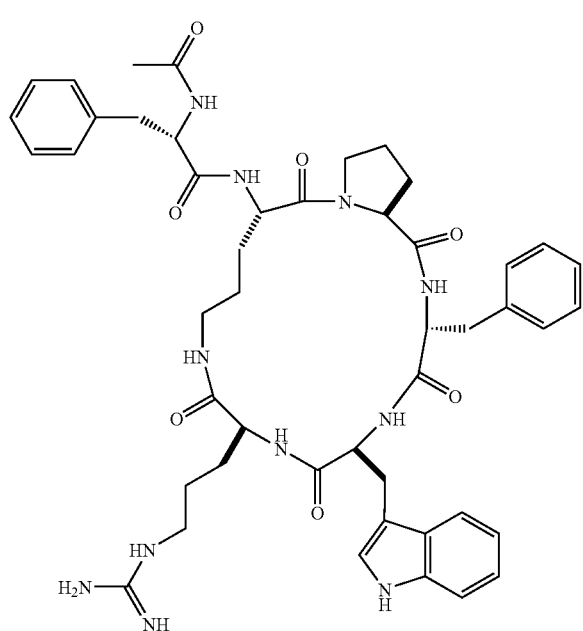
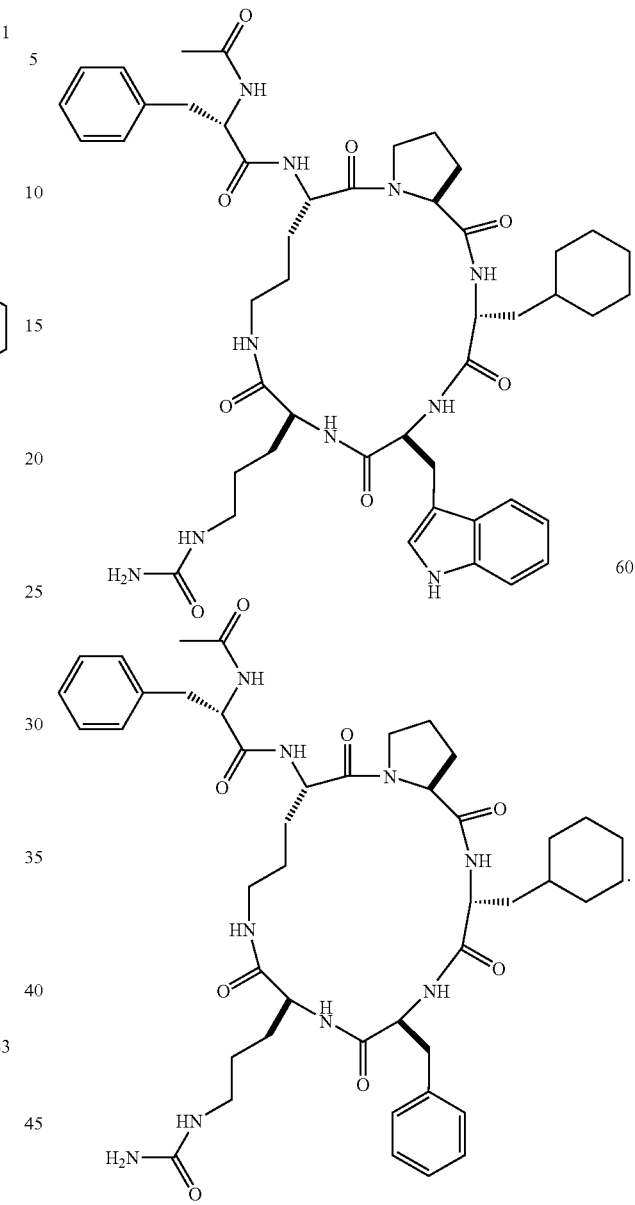
19. A method for treating osteoarthritis in a mammal, said method comprising the step of: administering to a mammal in need thereof, an effective amount of a composition comprising a C5a G protein-coupled receptor antagonist compound that (a) has substantially no agonist activity and (b) is a cyclic peptide or peptidomimetic compound of formula I:
(I)
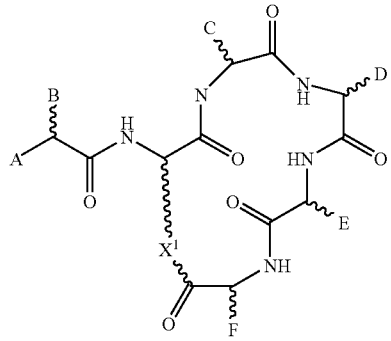

wherein A is NH-acyl; B is the side chain of L-phenylalanine; C is the side chain of L-proline; D is the side chain of D-cyclohexylalanine; E is the side chain of L-tryptophan; F is the side chain of L-arginine; and $X^1$ is —$(CH_2)_n$NH—, where n is 3.

* * * * *